US007256172B1

(12) United States Patent
Cocks et al.

(10) Patent No.: US 7,256,172 B1
(45) Date of Patent: Aug. 14, 2007

(54) METHOD OF TREATMENT AND AGENTS USEFUL FOR SAME

(75) Inventors: Thomas Matthew Cocks, Abbotsford (AU); James David Moffatt, North Fitzroy (AU)

(73) Assignee: The University of Melbourne, Parkville, Victoria (AU)

( * ) Notice: Subject to any disclaimer, the term of this patent is extended or adjusted under 35 U.S.C. 154(b) by 0 days.

(21) Appl. No.: 09/787,356

(22) PCT Filed: Sep. 15, 1999

(86) PCT No.: PCT/AU99/00775

§ 371 (c)(1),
(2), (4) Date: Jun. 25, 2001

(87) PCT Pub. No.: WO00/15243

PCT Pub. Date: Mar. 23, 2000

(30) Foreign Application Priority Data

Sep. 15, 1998 (AU) .................................... PP 5922
Feb. 12, 1999 (AU) .................................... PP 8658

(51) Int. Cl.
*A01N 37/18* (2006.01)
*A61K 38/00* (2006.01)
*A61K 49/00* (2006.01)
*G01N 33/53* (2006.01)
*G01N 33/567* (2006.01)

(52) U.S. Cl. ........................... 514/2; 424/9.1; 435/7.1; 435/7.2; 530/402

(58) Field of Classification Search .................... 514/2; 530/402

See application file for complete search history.

(56) References Cited

U.S. PATENT DOCUMENTS 6,323,219 B1 * 11/2001 Costanzo .................... 514/317

OTHER PUBLICATIONS

Cicala C, et al. British J. Pharmacol. 122:PROC SUPPL pp14P, Oct. 1997.*
"Ligand Cross-Reactivity Within the Protease-Activated Receptor Family" Brian D. Blackhart, et al, The Journal of Biological Chemistry, 1996, vol. 271, No. 28, Issue of Jul. 12, pp. 16466-16471, 1996.

"Characterization of a Functional Thrombin Receptor", Issues and Opportunities by Shaun R. Coughlin, et al, J. Clin. Invest., The American Society for Clinical Investigation, Inc., vol. 89, Feb. 1992, 351-355.
"Endothelium-Dependent Hyperpolarization: A Role in the Control of Vascular Tone", by Christopher J. Garland, et al., TiPS—Jan. 1995, vol. 16, pp. 23-30.
"Protease Activated Receptor 3 is a Second Thrombin Receptor in Humans" by Hiroaki Ishihara, et al., Nature, vol. 386, Apr. 3, 1997, pp. 502-506.
"Interactions of Mast Cell Tryptase With Thrombin Receptors and PAR-2", by Marina Molino, et al, The Journal of Biological Chemistry, vol. 272, No. 7, Issue of Feb. 14, pp. 4043-4049, 1997.
"In Vivo Protein Transduction: Delivery of a Biologically Active Protein into the Mouse" by Steven R. Schwarze, et al., Science, vol. 285, Sep. 3, 1999; pp. 1659-1572.
"Molecular Cloning of a Functional Thrombin Receptor Reveals a Novel Proteolytic Mechanism of Receptor Activation" by Thien-Khai H. Vu, et al., Cell, vol. 64, 1057-1068, Mar. 22, 1991.
Akers, I.A. et al., "Human lung fibroblasts express PAR-2 which mediate the mitogenic effects of mast cell tryptase" Faseb J., vol. 12, No. 4, p. A434, (1998).
Joliot A. et al., "Cell biology" vol. 4, $2^{nd}$ edition, pp. 111-119, Academic Press Inc. (1998).
Vives et al., "A truncated HIV-1 Tat protein basic domain rapidly translocates through the plasma membrane and accumulates in the cell nucleus" Journal of Biological Chemistry, American Society of Biological Chemists, Baltimore, MD, US, vol. 272, No. 25, pp. 16010-16017, (1997).

* cited by examiner

*Primary Examiner*—Robert S. Landsman
(74) *Attorney, Agent, or Firm*—Knobbe, Martens, Olson & Bear, LLP

(57) ABSTRACT

The present invention relates generally to a method of inducing, stimulating or otherwise facilitating bronchoprotection in humans and animals by modulating bronchial constriction and/or inflammation. The present invention is predicated in part on the identification of receptors in airway epithelium which mediate inhibition of bronchoconstriction and/or inflammation following their activation. More particularly, the present invention identifies that activation of protease activated receptors (PARs) results in relaxation of airway epithelium. Activation of airway epithelium PARs inhibits bronchoconstriction and/or inflammation and thereby mediates bronchoprotection of the airways. The present invention further provides a method for the prophylaxis and treatment of disease conditions in airways such as asthma and bronchitis and further provides methods for the diagnosis and screening of agents useful in the prophylaxis and treatment of airway disease conditions.

16 Claims, 48 Drawing Sheets

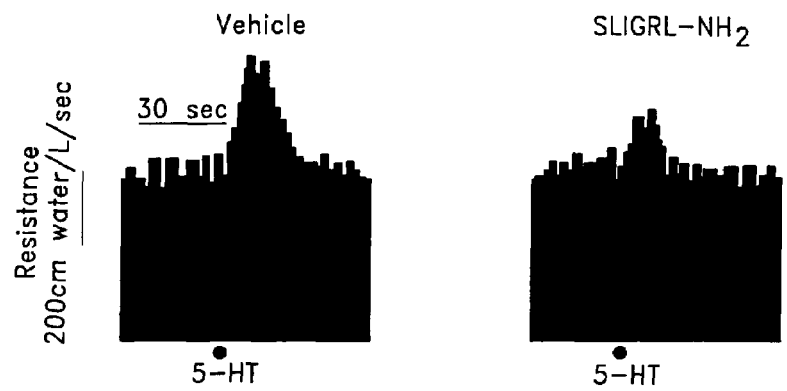
FIG. 29A
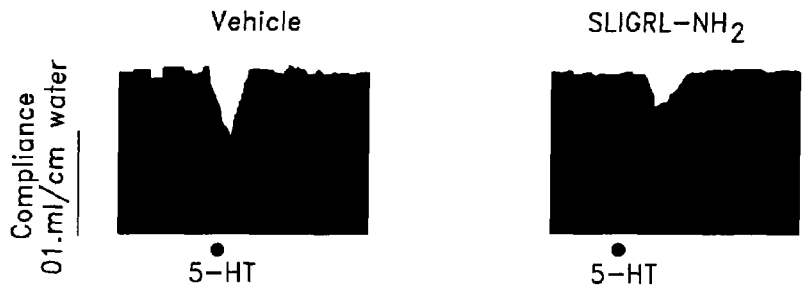
FIG. 29B
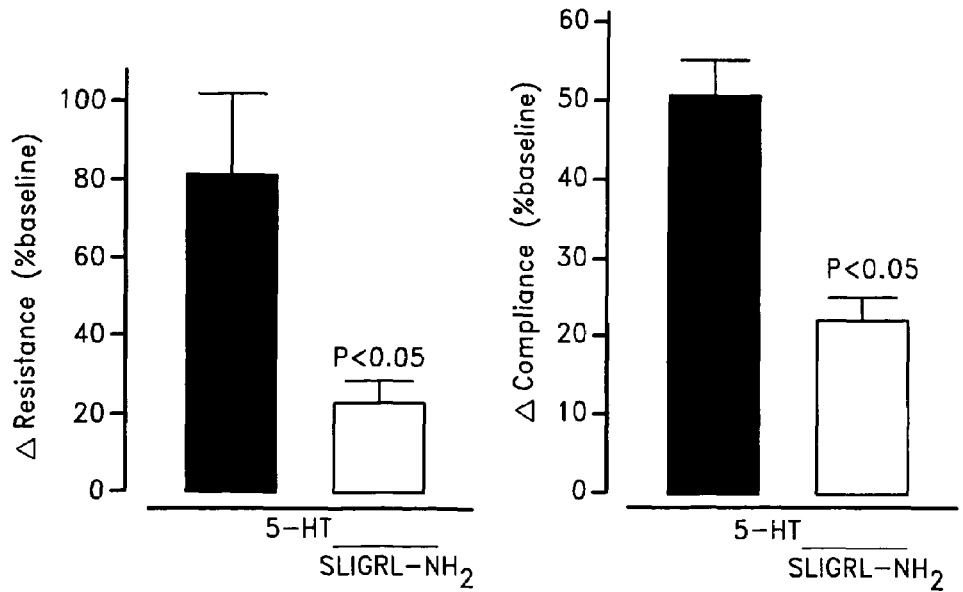
FIG. 29C
FIG. 29D

SEQUENCE LISTING

```
<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: The peptide TRAP from human protease-activated
      receptor 1(PAR-1)

<400> SEQUENCE: 1

Ser Phe Leu Leu Arg Asn
1               5

<210> SEQ ID NO 2
<211> LENGTH: 6
<212> TYPE: PRT
<213> ORGANISM: Artificial Sequence
<220> FEATURE:
<223> OTHER INFORMATION: The peptide PAR2-AP from human
      protease-activated receptor-2 (PAR-2)

<400> SEQUENCE: 2

Ser Leu Ile Gly Arg Leu
1               5

<210> SEQ ID NO 3
<211> LENGTH: 6
<212> TYPE: PRT
<213> ORGANISM: Artificial Sequence
<220> FEATURE:
<223> OTHER INFORMATION: The human protease-activated receptor-2 (PAR-2)
      tethered ligand sequece

<400> SEQUENCE: 3

Ser Leu Ile Gly Lys Val
1               5

<210> SEQ ID NO 4
<211> LENGTH: 6
<212> TYPE: PRT
<213> ORGANISM: Artificial Sequence
<220> FEATURE:
<223> OTHER INFORMATION: Scrambled peptide sequence

<400> SEQUENCE: 4

Leu Ser Ile Gly Arg Leu
1               5

<210> SEQ ID NO 5
<211> LENGTH: 7
<212> TYPE: PRT
```

```
<213> ORGANISM: Artificial Sequence
<220> FEATURE:
<223> OTHER INFORMATION: The carboxyl-terminal of mouse
      protease-activated receptor 2 (PAR-2)

<400> SEQUENCE: 5

Cys Ser Val Lys Thr Ser Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: The protease-activated receptor 4 (PAR-4)
      activating peptide

<400> SEQUENCE: 6

Gly Tyr Pro Gly Lys Phe
1               5

<210> SEQ ID NO 7
<211> LENGTH: 7
<212> TYPE: PRT
<213> ORGANISM: Artificial Sequence
<220> FEATURE:
<223> OTHER INFORMATION: The human protease-activated receptor-2 (PAR-2)
      tethered ligand sequence

<400> SEQUENCE: 7

Ser Leu Ile Gly Lys Val Asp
1               5

<210> SEQ ID NO 8
<211> LENGTH: 6
<212> TYPE: PRT
<213> ORGANISM: Artificial Sequence
<220> FEATURE:
<223> OTHER INFORMATION: The protease-activated receptor-4 (PAR-4)
      activating peptide

<400> SEQUENCE: 8

Gly Tyr Pro Gly Gln Tyr
1               5

<210> SEQ ID NO 9
<211> LENGTH: 6
<212> TYPE: PRT
<213> ORGANISM: Artificial Sequence
<220> FEATURE:
<223> OTHER INFORMATION: Tethered ligand sequence for Xenopus
      protease-activated receptor-1 (PAR-1)

<400> SEQUENCE: 9

Thr Phe Arg Ile Phe Asp
1               5

<210> SEQ ID NO 10
<211> LENGTH: 6
<212> TYPE: PRT
<213> ORGANISM: Artificial Sequence
<220> FEATURE:
<223> OTHER INFORMATION: Tethered ligand sequence for mouse and rat
      protease-activated receptor-1 (PAR-1)

<400> SEQUENCE: 10

Ser Phe Phe Leu Arg Asn
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Tethered ligand sequence for human
      protease-activated receptor-3 (PAR-3)

<400> SEQUENCE: 11

Thr Phe Arg Gly Ala Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Tethered ligand sequence for mouse
      protease-activated receptor-3 (PAR-3)

<400> SEQUENCE: 12

Ser Phe Asn Gly Gly Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Tethered ligand sequence for human
      protease-activated receptor-4 (PAR-4)

<400> SEQUENCE: 13

Gly Tyr Pro Gly Gln Val
1               5
```

METHOD OF TREATMENT AND AGENTS USEFUL FOR SAME

BACKGROUND OF THE INVENTION

1. Field of the Invention

The present invention relates generally to a method of inducing, stimulating or otherwise facilitating bronchoprotection in humans and animals by modulating bronchial constriction and/or inflammation. The present invention is predicated in part on the identification of receptors in airway epithelium which mediate inhibition of bronchoconstriction and/or inflammation following their activation. More particularly, the present invention identifies that activation of protease activated receptors (PARs) results in relaxation of airway epithelium. Activation of airway epithelium PARs inhibits bronchoconstriction and/or inflammation and thereby mediates bronchoprotection of the airways. The present invention further provides a method for the prophylaxis and treatment of disease conditions in airways such as asthma and bronchitis and further provides methods for the diagnosis and screening of agents useful in the prophylaxis and treatment of airway disease conditions.

2. Description of the Related Art

Many receptors for biologically-active effector molecules are large proteins embedded in biological membranes. They serve as transducers of information mediated by effectors such as hormones and cytokines, and are also important in the mechanism of action of pharmaceutical agents. For example, receptors located within the outer regions of the cellular membrane act to transduce such information into the cell, which may then respond in a number of different ways via specific secondary messenger systems. Therefore, these types of receptors have specific extracellular and intracellular domains which allow information, such as hormonal signals, to be appropriately detected and processed by cells.

Protease-activated receptors (PARs) are a relatively new subtype of a superfamily of membrane receptors which have seven membrane-spanning regions and are coupled to intracellular second messenger mechanisms via G proteins. The three known members, respectively designated PAR1, PAR2 and PAR3, have been cloned, and shown to be expressed in vascularised tissues comprising endothelial and smooth muscle cells (PAR1 and PAR2) and platelets (PAR1 and PAR3). A fourth receptor, designated PAR4, has also recently been demonstrated on platelets of PAR3 deficient mice and has been cloned (Kahn et al, 1998); the human homologue has also been cloned (Xu et al, 1998).

PARs are activated in a unique manner, which is illustrated in FIG. 1. As the name indicates, limited proteolysis by specific proteases (proteinases) removes part of the extracellular N-terminal region of the receptor, so that the newly-shortened N-terminal acts as a ligand for an as yet undefined binding region on the remainder of the receptor in order to signal the cell to respond. Thus, PARs have their own inbuilt or "tethered" ligands, and the specific protease activity reveals that these latent, intrinsic ligands act as ligands in their own right rather than as exogenous effectors.

PAR1 (Vu et al, 1991; Coughlin et al, 1992) and PAR3 (Ishihara et al, 1996) are activated primarily by the blood-borne protease, thrombin, which is believed to be involved in thrombosis, inflammation and mitogenic growth (De Catering & Sicari, 1993; Dennington & Berndt 1994; Fager, 1995). For example, thrombin causes smooth muscle in the airways to proliferate, which may cause the airway to thicken and become obstructed. PAR1 is also located on vascular endothelial cells, where, like many other receptor types, stimulation leads to release of nitric oxide (NO) and other factors which then cause the muscle in the wall of the vessels to relax (Muramatsu et al, 1991; Tesfamariam et al, 1993; Tesfamariam, 1994; Hwa et al, 1996; Saifeddine et al, 1996). Under normal circumstances, the enzymatic activity of thrombin is strongly suppressed by a number of endogenous inhibitors.

PAR2 differs from both PAR1 and PAR3 receptors in that it is activated not by thrombin, but by trypsin and trypsin-like enzymes, such as mast cell-derived tryptase (Molino et al, 1997). Trypsin is usually confined to the upper gastrointestinal tract after its generation by activation of its pancreatic precursor, trypsinogen. Trypsinogen is induced in vascular endothelial cells by tissue plasminogen activator [TPA] (Koshikawa et al, 1997). Tryptase is released in large concentrations from mast cells (Caughey, 1994). Mast cells are believed to have a central role in the pathogenic manifestations of asthma. Tryptase stimulates mucus release and can inactivate some peptides such as vasoactive intestinal peptide (VIP) that relax airway smooth muscle in experimental animals. This suggests that the PARs play a role in the aetiology of airway disease by inducing contraction of smooth muscle cells.

In addition to tryptase, tryptase-like enzymes are released by clara cells (Yasuoka et al, 1997), which are common in the epithelium lining the small bronchi of most mammals, including humans, the trachea of the mouse, and by lymphocytes which enter the inflamed airway in large numbers. Trypsin has been localised to normal airway epithelium (Koshikawa et al, 1997). In addition, tryptase-like enzymes are thought to be involved in a number of inflammatory responses and diseases, such as atherosclerosis (Atkinson et al, 1994; Kovanen et al, 1995) and varicosis (Yamada et al, 1996). Furthermore and importantly, as well as directly activating mast cell degranulation via IgE-antigen recognition, the antigens of some dust mites and pollens are proteases with trypsin-like activity (Caughey, 1997). Therefore, allergens which are central to, and the causal agents of, many airway diseases have the potential to directly and indirectly activate PAR2.

PAR1 and PAR2, but not PAR3 (Isihara et al, 1997) can also be activated by short synthetic peptide sequences corresponding to those of the tethered ligands. For PAR1, this tethered ligand is SFLLRN—$NH_2$ (SEQ ID NO:1), which is also known as TRAP (thrombin receptor-activating peptide)). The tethered ligand sequence for mouse PAR2 is SLIGRL—$NH_2$ (SEQ ID NO:2), and is referred to herein as PAR2 activating peptide (PAR2-AP). Therefore, these peptides can be used to mimic enzyme mediated PAR activation and to study the effects of PAR activation.

The genes for PAR1, PAR2 and PAR3 have been cloned (Vu et al, 1991; Nystedt et al, 1994; Bohm et al, 1996a; Saifeddine et al, 1996 and Ishihara et al, 1997). PAR2 mRNA has been shown to be highly expressed in vascularised or endothelialised tissues such as the stomach, intestine, pancreas, kidney and liver. In the gut, PAR2 mRNA is located mainly in epithelial cells (Bohm et al, 1996b). In blood vessels, functional PAR2 has been localised nearly exclusively to endothelial cells, where, like PAR1, it mediates endothelium-dependent vasodilation (Hwa et al, 1996; Saifeddine et al, 1996). It has been proposed that PAR2 acts as a trypsin sensor in the pancreas (Bohm et al, 1996a) and is involved in a possible cytoprotective mechanism for gut epithelia exposed to trypsin (Bohm et al, 1996b). Apart from these proposed activities, little is known of other physiological roles for these receptors.

Following activation, PARs are inactivated by rapid internalization, which also provides the signals for rapid generation of new receptors from intracellular pools and de novo protein synthesis (Hoxie et al, 1993; Bohm et al, 1996b). This provides a powerful self-replenishing system to maintain adequate tissue levels of receptors.

Like PAR1, PAR2 mediates relaxation of arteries via the release of nitric oxide (NO; Moncada et at, 1991) and of endothelium-derived hyperpolarising factor (EDHF: Garland et al, 1995), although the EDHF-dependent mechanism for PAR1 is different from that for PAR2. The mechanisms of receptor recycling also regulate the way in which endothelial cells recover their ability to respond to further protease challenge, at least within two to three hours after the first challenge. For PAR1, this recovery process involves rapid recycling of receptors (30 min–150 min) without the tethered ligand sequence, but no new N-terminal receptors are produced. For PAR2, however, fully intact new receptors are rapidly synthesized from stable mRNA, and are inserted into the plasma membrane (Bohm et al, 1996a).

Only PAR1 has been identified in the human vasculature (Nelken, 1992), where expression was reported to be isolated to endothelial cells in atheroma-free arteries. In vessels affected by atherosclerosis, PAR1 mRNA was found in endothelial, smooth muscle and mesenchymal-appearing cells. Studies on human endothelial cell PAR function have been limited to the measurement of calcium fluxes in transfected cell lines (Marl, 1995) and umbilical vein endothelial cells (Ngaiza et al, 1991; Kruse et al, 1995). An atypical PAR has also been identified in human coronary arteries (Hamilton et al, 1998).

The incidence and prevalence of airway diseases such as asthma and bronchitis, which are characterized by airflow obstruction, inflammation and pathological changes in airway tissue are increasing globally (Barnes et al, 1996a). However, it is unknown why some people develop these types of airway diseases, while other people exposed to the same environmental factors do not. One possibility is that the airway defenses of patients who develop the disease are less efficient than those of non-afflicted subjects.

Asthmatic patients suffer from episodic airflow limitation caused by bronchospasm, oedema and thickening of the airway walls. In addition, one of the hallmarks of asthma is that the bronchi are hypersensitive to specific and non-specific stimuli, causing them to contract too much and too sensitively, thereby narrowing the airways and making breathing difficult (Barnes, 1996b; Barnes et al, 1996c). The most widely-used treatment for asthma is administration of drugs that cause the bronchial muscles to relax and the airways to dilate, thus restoring the ability to breath. The most commonly used drugs for this purpose are the so-called beta-2 agonists. These drugs stimulate another subtype of the seven transmembrane, G protein-coupled receptor superfamily, the beta-2 adrenoceptors, which are located on the muscle and mediate relaxation via well-defined biochemical mechanisms. While beta-2 agonists are effective in most patients, it has recently been discovered that some asthmatics respond poorly to beta-2 agonists, and the agonists may mediate down-regulation of patient responses during chronic treatment due to genetic mutations in the beta-2 adrenoceptor sequence. Additionally, concerns have been raised about the possibility that regular use of beta 2-adrenoceptor agonists may increase the risk of death from asthma.

SUMMARY OF THE INVENTION

Accordingly, one aspect of the present invention provides an isolated molecule comprising PAR activity wherein said molecule is isolatable from airway epithelium and upon activation, stimulates, induces or otherwise facilitates inhibition of bronchoconstriction and/or inflammation in humans and animals.

Reference herein to animals includes apart from humans, primates, livestock animals (e.g. sheep, cows, horses, pigs, goats), laboratory test animals (e.g. mice, rats, rabbits, guinea pigs), companion animals (e.g. cats, dogs) and captive wild animals (e.g. foxes, deer, kangaroos).

Although the present invention extends to any PAR expressed in airway epithelium, it is particularly directed to PAR1 and PAR2 and is most particularly directed to PAR2. Accordingly, reference hereinafter to "PAR2" includes other PARs which behave in a functionally similar manner.

Another aspect of the present invention is directed to an isolated molecule comprising PAR2 activity wherein said molecule is isolatable from airway epithelium and upon activation, stimulates, induces or otherwise facilitates inhibition of bronchoconstriction and/or inflammation in humans and animals.

Preferably, the PAR2 is in isolated form meaning that it is has undergone at least one purification step away from contaminating material. However, PAR2 may also be part of a membrane formulation or preparation. PAR2 may also be prepared in recombinant form or be chemically synthesized.

The recombinant form of PAR2 may be as a single polypeptide or a modular molecule comprising various parts of PAR2 or its homologues.

According to this aspect of the present invention there is provided a polypeptide in recombinant form which is homologous to a PAR2 in airway epithelium, said polypeptide comprising an N-terminal portion, transmembrane portion, an intracellular portion and a ligand binding portion wherein upon proteolytic cleavage of the N-terminal portion, the remaining extracellular portion folds onto or otherwise interacts with the ligand binding portion to activate the recombinant polypeptide.

Each portion of the above polypeptide may be derived from airway epithelium PAR2 or it may be in modular form meaning that the portions are derived from different molecules. For example, the extracellular portion may be from PAR2, the transmembrane portion may be from another receptor and the intracellular portion may be any G-protein interacting region.

Yet another aspect of the present invention provides a recombinant, synthetic or purified, naturally occurring molecule comprising PAR2 activity wherein said molecule is isolatable from airway epithelium and, upon activation by a PAR2 activating peptide, stimulates, induces or otherwise facilitates inhibition of S bronchoconstriction and/or inflammation in humans and animals.

BRIEF DESCRIPTION OF THE DRAWINGS

FIG. 5A shows chart recordings of changes in isometric force in two rings contracted to 60%–70% $F_{max}$ with carbachol (–logM) after which PAR2-AP was added (–logM). FIG. 5B shows group data from six experiments described in (A). Responses are expressed as percentages of the contraction to carbachol and values are mean±SEM. Positive values represent contractions.

FIGS. 29A–29D are graphical representations demonstrating that the PAR2 activating peptide SLIGRL—NH$_2$ (SEQ ID NO:2) causes inhibition of bronchoconstriction in vivo. Original chart recordings (a, b) and grouped data (c, d) showing the effect of a 30 sec exposure to an aerosol of a 0.1 mg/ml solution of SLIGRL—NH$_2$ (SEQ ID NO:2) on 5-HT (3 nmol/kg i.v)-induced changes in airway resistance ($R_L$; a, c) and dynamic compliance ($C_{dyn}$; b, d) in the anaesthetised rat. Not shown is the complete inhibition of bronchoconstriction to 5—HT lasting at least 45 min occurred when SLIGRL—NH$_2$ (SEQ ID NO:2) was used at 1 mg/ml. Values are mean±s.e. from n=3 experiments.

DETAILED DESCRIPTION OF THE PREFERRED EMBODIMENT

Figure 1:
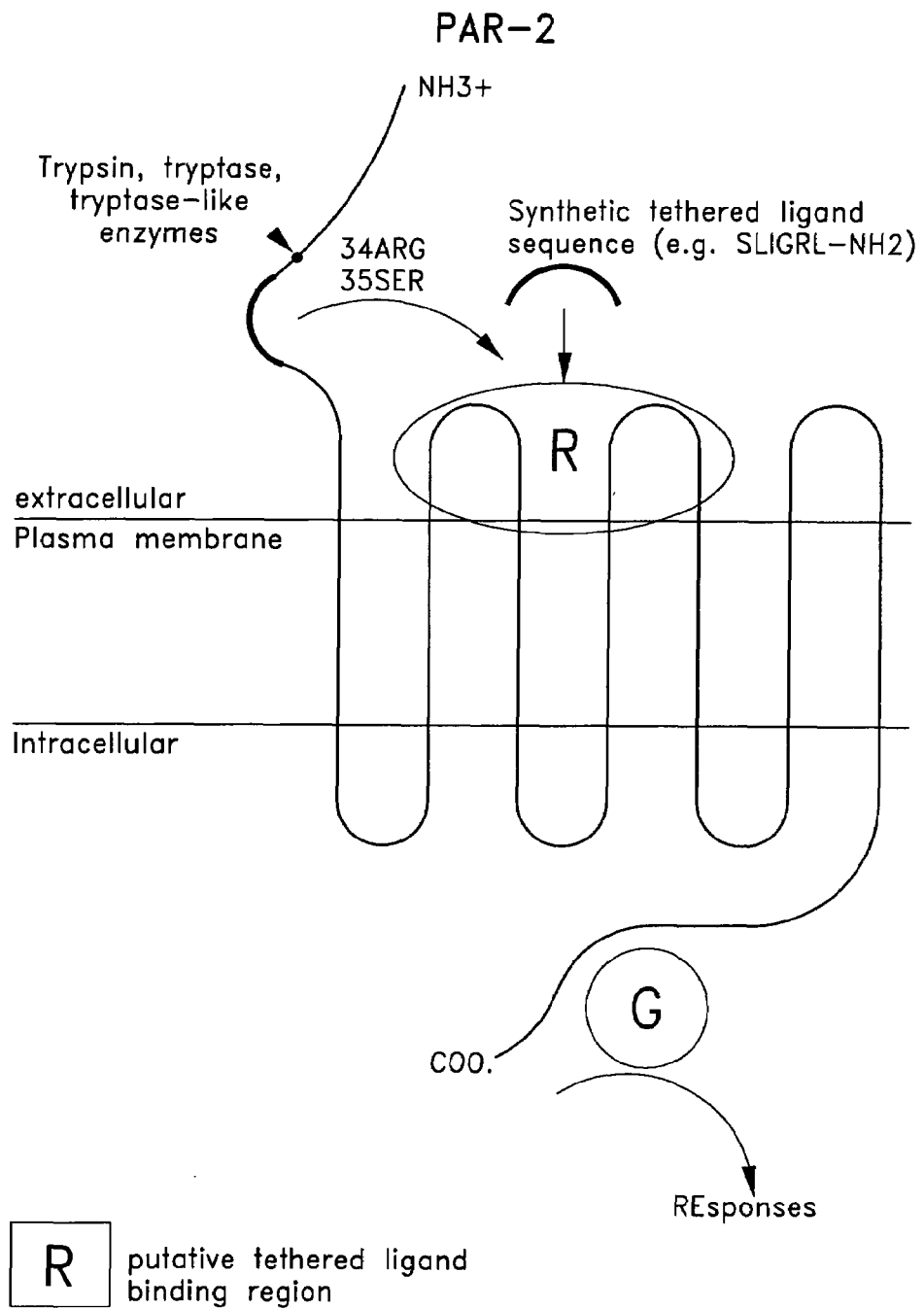
FIG. 1 is a schematic representation of the PAR2 receptor. The black loops depict the membrane-spanning regions in a theoretical cell. The receptor is activated by trypsin (or by other trypsin-like proteases, eg tryptase) by cleavage of the arginine$_{34}$-serine$_{35}$ peptide bond amino-terminally to the arginine$_{34}$ in the extracellular N-terminal domain. The next approximately six amino acids of the new N-terminal (called the tethered ligand sequence, solid box) now 'flip' on to another, undefined region of the remaining receptor to initiate intracellular G protein (G) coupling and signalling, shown here as "responses". The putative tethered ligand binding region ("R") of the receptor can also be directly activated by exogenous addition of a synthetic peptide identical or homologues to the tethered ligand sequence SLIGRL—NH$_2$ (SEQ ID NO:2) (single letter amino acid code) designating the mouse PAR2 activating sequence. The similar but genetically distinct PAR1, or thrombin receptor, is enzymically activated by thrombin by cleaving a arginine$^{41}$-serine$^{42}$-bond and the synthetic tethered ligand sequence SFLLRN—NH2 (SEQ ID NO:1) designating the human PAR2 activating sequence.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Bibliographic details of the publications referred to by author in this specification are collected at the end of the description.

The subject specification contains amino acid sequence information prepared using the programme PatentIn Version 2.0, presented herein after the bibliography. Each amino acid sequence is identified in the sequence listing by the numeric indicator <210> followed by the sequence identifier (e.g. <210>1, <210>2, etc). The length, type of sequence (e.g. protein (PRT), etc) and source organism for each amino arid sequence are indicated by information provided in the numeric indicator fields <211>, <212> and <213>, respectively. Amino acid sequences referred to in the specification are defined by the information provided in numeric indicator field <400> followed by the sequence identifier (e.g. <400>1, <400>2, etc).

Airway disease like asthma and bronchitis are predicted to continue their dramatic rate of increase in developed societies, and therefore, new therapies, procedures and methods of diagnosis, and methods of screening for prophylactic or therapeutic agents are urgently needed.

In work leading up to the present invention, the inventors identified that activation of PARs located immunohistochemically on airway epithelium, caused dilation of bronchi and bronchioles. This physiologically relevant protective response in airways was mediated mainly by a cyclooxygenase product (e.g. $PGE_2$) released from the epithelium. In addition, after receptor desensitization due to internalization and degradation, functional PARs are rapidly replenished to the cell surface by protein trafficking and de novo synthesis. In accordance with the present invention, epithelial PARs, and in particular PAR2 are regarded as potential targets for the development of new therapies for inflammatory diseases like asthma and bronchitis.

The inventors have now surprisingly found that PAR2 in the epithelial layer has an anti-inflammatory role in the airways, and that PAR2 epithelial and smooth muscle: cells are differentially regulated.

The inventors have shown that epithelial PARs and in particular PAR2, initiate important autocrine and paracrine protective tissue responses in the airways which include regulation of smooth muscle contractility, inflammatory cell migration and function, neural activity and tissue remodeling, and therefore enable new therapies for airway inflammatory diseases like asthma and bronchitis.

The present invention is predicated in part on the identification of airway epithelial PARs which modulate bronchodilation and inflammation. More particularly, the inventors have identified PARs in airway epithelium which, upon activation, simulate, induce or otherwise facilitate inhibition of bronchoconstriction and/or inflammation in humans and animals.

The identification of PAR2 in airway epithelium provides a mechanism for treating airway disease conditions which result in bronchoconstriction and/or inflammation of airway tissue.

In a preferred embodiment, the condition to be treated is a broncho-constrictive disease such as but not limited to asthma, bronchitis including brochiolitis obliterans, rhinitis, hay-fever, alveolitis of diverse aetiologies, ciliary dyskinesin sarcoidosis and pulmonary inflammatory diseases. Diseases involving PAR are summarized in Table 1 below:

TABLE 1

Diseases involving PAR (A) Diseases of the lung and airways, including but not limited to:
Alveolitis of diverse aetiologies
Asthma
Bronchitis
Bronchiolitis, including bronchiolitis obliterans
Ciliary dyskinesis
Pulmonary fibrosis of diverse aetiologies
Pulmonary hypertension and its sequelae
Sarcoidosis
Proposed galenical forms: aerosols of solutions, suspensions or dry powders, including micronised preparations; nasal sprays; liposomal formulations, including cationic liposomes for gene vector transfer.

(B) Diseases of the gatrointestinal tract, including but not limited to:
Crohn's disease
Gastric and gastrointestinal ulceration, including ulceration triggered by NSAID therapy
Inflammatory bowel disease
Intestinal adhesion induced by surgery, injury or other mechanisms
Ulcerative colitis
Hirschsprung's disease
Irritable Bowel Syndrome
Proposed galenical forms: oral formulations, including encapsulated, enteric-coated and sustained release matrix formulations; suppositories; enemas; implantable gels or slow release matrixes.

(C) Disease of the eye, including but not limited to:
Conjunctival inflammation
Corneal neovascularisation
Corneal ulceration
Glaucoma
Proposed galenical forms: drops and gels, including slow release implantable matrices; additions to contact lenses as coatings or integral matrix component.

(D) Disease of the genitourinary tract, including but not limited to:
Ciliary dyskinesis
Cystitis
Disorders of the fallopian tubes, including infertility
Incontinence
Pelvic inflammatory disease
Regulation of the contractility of the uterus in pregnancy
Urethral inflammation (E) Disease of the auditory canal and middle ear, including but not limited to:
ciliary dyskinesis
Eustachian canal obstruction
Otitis media
Proposed galenical forms: drops and gels, including slow release implantable matrices; additions to grommets and stents as coatings or integral matrix component.

(F) Diseases of the vasculature and lymphatics, including but not limited to:
atherosclerosis
ischaemia
lymphoedema
modulation of angiogenesis
systemic, pulmonary and portal hypertension
re-anastomosis
thrombis
vascular reperfusion injury Proposed galenical forms: injectables; drops; gels including slow release implantable matrices; wrappings; additions to surgical devices including stents, grommets, valves, electrodes, catheters, synthetic vessels, as coatings or integral matrix component.

According to this aspect of the present invention, there is contemplated a method for the prophylaxis or treatment of an airway disease condition in a human or animal said method comprising administering to said human or animal an effective amount of an agent capable of activating an airway epithelium PAR for a time and under conditions sufficient for activation of said PAR to occur wherein the activated PAR stimulates, induces or otherwise facilitates inhibition of bronchoconstriction and/or inflammation.

Preferably, the PAR is PAR2.

According to this preferred embodiment, there is provided a method for the prophylaxis or treatment of an airway disease condition in a human or animal said method comprising administering to said human or animal an effective amount of an agent capable of activating an airway epithelium PAR2 for a time and under conditions sufficient for activation of said PAR2 which then stimulates, induces or otherwise facilitates inhibition of bronchoconstriction and/or inflammation.

The agent may be a nucleotide sequence, low molecular weight compound, or a derivative, part, fragment, analogue, mimetic, mimotope or chemical equivalent of all or a portion of PAR2. In particular, the agent may be a peptide having similar biological activity to SFLLRN—$NH_2$ (SEQ ID NO:1) and/or SLIGRL—$NH_2$ (SEQ ID NO:2) and/or SLIGKV—$NH_2$ (SEQ ID NO:3) (see Blackhart et al, 1996). Gene therapy may also be employed such as using cationic liposomes for gene vector transfer.

The compositions may be administered orally, intranasally, via aerosol, via inhalation, parenterally, intramuscularly, intreperitoneally, intravenously, rectally or subcutaneously amongst other routes. Administration may also be facilitated by fusing the agent to a membrane penetrating molecule such as penetration or the TAT protein from HIV-1 (see Schwarze et al, 1999). Gene transfer vectors may also be employed.

Accordingly, another aspect of the present invention is directed to a composition useful for facilitating bronchoprotection said composition comprising an activator of PARs in airway epithelium and one or more pharmaceutically acceptable carriers and/or diluents.

The activator of this aspect of the present invention may be referred to as an "active ingredient" or "agent". The activator may also be considered as an "agonist" of PAR activation.

Compositions suitable for injectable use include sterile aqueous solutions (where water soluble) and sterile powders for the extemporaneous preparation of sterile injectable solutions. They are generally stable under the conditions of manufacture and storage and must be preserved against the contaminating action of microorganisms such as bacteria and fungi. The carrier can be a solvent or dispersion medium containing, for example, water, ethanol, polyoil (for example, glycerol, propylene glycol and liquid polyethylene glycol, and the like), suitable mixtures thereof and vegetable oils. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride.

Sterile injectable solutions are prepared by incorporating the active compounds in the required amount in the appropriate solvent with various of the other ingredients enumerated above, as required, followed by, for example, filter sterilization or sterilization by other appropriate means. In the case of sterile powders for the preparation of sterile injectable solutions, a preferred method of preparation includes vacuum drying and freeze-drying which yield a powder of the active ingredient plus any additional desired ingredient from a previously sterile-filtered solution.

When the active ingredient is suitably protected, it may be orally administered, for example, with an inert diluent or with an assimilable edible carrier, or it may be enclosed in hard or soft shell gelatin capsule, or it may be compressed into tablets.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; and a lubricant such as magnesium stearate. Any material used in preparing any dosage unit form should be pharmaceutically pure and substantially non-toxic in the amounts employed. In addition, the active compounds) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

Effective amounts of the subject agent will vary depending on the condition to be treated by may range from 0.001 ng/kg body weight to 100 mg/kg body weight. The agent may be administered every minute or hourly, daily, weekly or monthly. The agent may be used prophylactically or in the treatment of a disease condition.

Methods and pharmaceutical carriers for preparation of pharmaceutical compositions are well known in the art, as set out in textbooks such as Remington's Pharmaceutical Sciences, 17th Edition, Mack Publishing Company, Easton, Pa., USA.

Another aspect of the present invention relates to a method of diagnosis of a condition mediated by bronchial contraction, comprising the step of activating a PAR as described above and measuring cellular response(s). The types of response(s) induced can be used as an indicator of pre-disposition to one or more of the conditions described above, thereby enabling diagnosis.

This method also enables the screening of putative therapeutic or prophylactic agents for one or more of these conditions. Accordingly, another aspect of the present invention provides a method of screening putative agents for the treatment or prophylaxis of a direct or indirect condition mediated by changes in smooth muscle cell contractility, comprising the step of exposing a PAR to the putative agent and measuring the ability of the agent to activate the PAR. Preferably, the PAR is PAR 1 or PAR2 or a PAR-like receptor.

The present invention further extends to antibodies to PAR2 and in particular to extracellular portions of PAR2. Such antibodies may be monoclonal or polyclonal. The antibodies of the present invention are particularly useful as therapeutic (e.g. as agonists) or as diagnostic agents.

PAR2 of the present invention may be used, for example, as an antigen to screen for naturally occurring antibodies to PAR2 in humans or animals. Alternatively, specific antibodies to PAR2 may be used to screen for PAR2 or an antigenic derivative or relative in a sample. This may provide an indication of whether PAR2 is immunologically normal and, if not, this may indicate a propensity to develop airway disease. Techniques for such assays are well known in the art and include, for example, sandwich assays and ELISA.

Accordingly, the present invention provides a method for detecting the presence of a PAR2 or an antigenic fragment thereof in a biological sample, said method comprising contacting said biological sample with an antibody to said PAR2 for a time and under conditions sufficient for a complex to form between said PAR2 and an antibody and then detecting said complex.

A biological sample according to this aspect is one which potentially contains PAR2 containing cells such as flem, respiratory mucus or biopsy tissue. In this context, a biological sample includes tissue and tissue extract. The presence of PAR2 in a biological sample may be determined using a wide range of immunoassay techniques such as those described in U.S. Pat. Nos. 4,016,043, 4,424,279 and 4,018, 653. This includes both single-site and two-site, or "sandwich", assays of the non-competitive types, as well as in the traditional competitive binding assays. Sandwich assays are among the most useful and commonly used assays and are favoured for use in the present invention. A number of variations of the sandwich assay techniques exist, and all are intended to be encompassed by the present invention.

Reference herein to "PAR" and more particularly "PAR2" includes all derivatives, mutants, parts, fragments, portions, homologues, mimetics, mimotopes, analogues or chemical equivalents of all or part of PAR2.

Analogues and mimetics include molecules which contain non-naturally occurring amino acids as well as molecules which do not contain amino acids but nevertheless behave functionally the same as PAR2. Natural product screening is one useful strategy for identifying analogues and mimetics. Natural product screening involves screening environments such as bacteria, plants, animals, rainforests, riverbeds, seabeds, aquatic environments, coral and antarctic or arctic environments for naturally occurring molecules which mimic, agonise or antagonise the subject of the present invention. Analogues of the subject PAR2 contemplated herein include modifications to side chains, incorporation of unnatural amino acids and/or their derivatives during peptide synthesis and the use of crosslinkers and other methods which impose conformational constraints on the peptide molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,5-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, malefic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N- bromosuccinimide or alkylation of the indole ring with 2-hydroxy-5-nitrobenzyl bromide or sulphenyl halides. Tyrosine residues on the other hand, may be altered by nitration with tetra nitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 2.

TABLE 2

| Non-conventional amino acid | Code |
| --- | --- |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |

TABLE 2-continued

| Non-conventional amino acid | Code |
|---|---|
| D-α-methyllysine | Dmlys |
| D-α-methylmethionine | Dmmet |
| D-α-methylornithine | Dmorn |
| D-α-methylphenylaianine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | DnmIeu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methynorvaline | Mnva |
| L-α-methylphenylalanine | Mphe |
| L-a-methylserine | Mser |
| L-α-methyltryptophan | Mtrp |
| L-α-methylvaline | Mval |
| N-(N-(2,2-diphenylethyl) carbamyimethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisoleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methyinorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylaianine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylaianine | Nmanap |
| N-methylpenicillamine | Nmpen |
| N-(ρ-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylaianine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-a-methyltyrosine | Mtyr |
| L-N-methylhomophenylaianine | Nmhphe |
| N-(N-(3,3-diphenylpropyl) carbamylmethyl)glycine | Nnbhe |

Crosslinkers can be used, for example, to stabilise 3D conformations, using homobifunctional crosslinkers such as the bifunctional imido esters having $(CH_2)n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleïmido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

All these types of modifications may be important to stabilise PAR2 or a PAR2 modulating agent. This may be important if these molecules are used, for example, in the manufacture of a therapeutic or diagnostic composition.

The present invention further contemplates chemical equivalents of the subject polypeptides. Chemical equivalents may not necessarily be derived from the subject PAR2 itself but may share certain conformational or functional similarities. Alternatively, chemical equivalents may be specifically designed to mimic certain physiochemical properties of the polypeptides. Chemical equivalents may be chemically synthesised or may be detected following, for example, natural product screening.

Reference herein to the PAR2 of the present invention should be read as including reference to all forms of the PAR2 including, by way of example, isoforms, monomeric, dimeric and multimeric forms and peptide fragments PAR2 as well as other PARs.

The invention will now be described in detail by way of reference only, to the following non-limiting Examples and Figures, in which:

Although the present invention is particularly directed to inhibition of bronchoconstriction and/or inflammation, the subject invention extends to PARs such as PAR2 orchestrating a wide range of bronchoprotective responses. In particular, the present invention extends to the development of technology stemming from the recognition that endogenous activators (e.g. trypsin) and PARs (e.g. PAR2) are co-localised in the epithelium and act as 2.1 amplifier of a PAR (e.g. PAR2) protective mechanism. (Reference to "inflammation" includes reference to oedema.

Abbreviations used herein are as follows:

| | |
|---|---|
| Ach | acetylcholine |
| ATP | adenosine 5'-triphosphate |
| 5 $F_{max}$/$KPSS_{max}$ | maximum force of contraction (grams) |
| FITC | fluorescein isothiocyanate |
| Hb0 | oxyhaemoglobin |
| IBMX | isobutyl methylxanthine |
| Indo | indomethacin |
| KPSS | potassium-containing physiological salt solution |
| L-NOARG | $N^G$-Nitro-L-arginine |
| NO | nitric oxide |
| PACAP | Pituitary adenylyl cyclase activating peptide |
| PAR | Protease activated Receptor |
| PAR2-AP | PAR2 Activating Peptide |
| SK | $Ca^{2+}$-activated $K^+$ channel |
| To | optimal tissue stretch to give maximum active force |
| TRAP | Thrombin Receptor-Activating Peptide, SFLLRN-NH$_2$ (SEQ ID NO:1) |
| VIP | vasoactive intestinal peptide |

EXAMPLE I

Materials and Methods

Chemicals

Acetylcholine chloride, bovine serum albumin, bradykinin triacetate, carbachol, cycloheximide, haemoglobin (bovine plasma), histamine dihydrochloride indomethacin, (−)-isoprenaline, $N^G$-nitro-I-arginine, substance P (acetate salt) and α-thrombin (bovine serum) were obtained from Sigma (MO, U.S.A.). Actinomycin D, apamin, aspirin, brefeldin A, carbaprostacyclin, isobutylmethyl xanthine (IBMX), prostaglandin ethanolamide, 9,11-dideoxy-9α 11α-methanoepoxy-prostaglandin F2α (U46619), prazosin hydrochloride and nifedipine were from Sapphire Bioscience (N.S.W., Australia). Trypsin (bovine pancreas) was from Worthington Biochem (NJ, U.S.A.) and SLIGRL—NH$_2$(SEQ ID NO:2), SLIGKV—NH$_2$ (SEQ ID NO:3) and SFLLRN—NH$_2$ (SEQ ID NO:1) were obtained from Auspep (Vic, Australia).

Stock solutions of haemoglobin (1 mM) were dissolved in 0.9% w/v NaCl and then reduced with sodium dithionite ($Na_2S_2O_4$). Excess $Na_2S_2O_4$ was removed by passing the solution through a Sephadex PD10 size exclusion column.

Stock solutions of brefeldin A (1 mM), carbaprostacyclin (1 mM), prostaglandin $E_2$ (1 mM), nifedipine (10 mM) and U46619 (1 mM) were in absolute ethanol, while those for indomethacin (100 mM) and $N^G$-nitro-L-arginine (100 mM) were in $Na_2CO_3$ and $NaHCO_3$, respectively. All subsequent dilutions of these drugs were in distilled water, as were solutions of all other drugs.

In Vitro Studies

The right and left main bronchi and their first order branches of specific pathogenfree (SPF) Balb/c mice (15–20 g; either sex), Hartley tricolour guinea-pigs (300–400 g; male) and Sprague-Dawley rats (200–350 g; either sex), all killed by either cervical dislocation or overdosed (i.p.) with sodium pentobarbitone, were cleared of surrounding connective tissue, nerves and blood vessels under a dissecting microscope and placed in cold, carbogenated (95% v/v $O_2$,5% v/v $CO_2$) Krebs solution (Kemp and Cocks, 1997). Human airway preparations (0.5–1 mm in external diameter) were dissected from lungs of cancer patients undergoing thoracotomy at The Royal Melbourne Hospital, Melbourne, Australia. The epithelium was removed from some bronchi either by mechanical abrasion of the luminal surface (guinea-pig) or by brief, gentle intraliminal flushing of the airways with Krebs containing 0.1% v/v Triton-X100 (mouse and rat). In each case, removal of the epithelium was verified histologically in 8 µm formalin-fixed, paraffin sections stained with haemotoxylin and eosin. Ring segments (approximately 2 mm long) of bronchi and bronchioles were mounted in Krebs (37° C.) on stainless steel wires (40 µm) in dual channel (5 ml) Mulvany-Halpern myographs (JP Trading, Aarhus, Denmark) to record changes in isometric force (Kemp and Cocks, 1997). After equilibration at a passive force between 0.2 g and 0.3 g, tissues were contracted to their maximum levels of active force (Fm.),) with acetylcholine (30 µM), thoroughly washed with Krebs and allowed to return to baseline. Various drugs or their vehicles were then added and 30 min later all tissues were contracted to approximately 40% $F_{max}$ with titrated concentrations of carbachol (10–500 nM). The L-type voltage-operated $Ca^{2+}$ channel inhibitor, nifedipine (0.3 µM) was added to all mouse and rat tissues after obtaining $F_{max}$ to control characteristic phasic contractile activity with carbachol. When a stable level of active force to carbachol was obtained, tissues were exposed to cumulatively increasing concentrations of the PAR1 and PAR2-activating enzymes, thrombin (bovine serum, Sigma, Mo., USA) and trypsin (bovine pancreas, 3× crystallised, Worthington Biochem, N.J., USA) respectively, and their synthetic tethered ligand peptide sequences, SFLLRN—NH$_2$ (SEQ ID NO:1) and SLIGRL—NH$_2$ (SEQ ID NO:2) (each >95% purity; Auspep, Parkville, Australia).

To assess the effect of enzyme-mediated receptor desensitisation on responses to the synthetic peptides, mouse bronchi were allowed to recover to their initial level of active force to carbachol following cumulative concentration-responses curves to trypsin (0.001–0.3 U/ml) or thrombin (0.001–0.3 U/ml) but with enzymes still present in the myograph chamber. When the force again reached a steady level, they were tested for desensitisation with maximum concentrations of trypsin and thrombin (0.3 U/ml). If no response occurred the tissues were then exposed to cumulative concentrations of either SLIGRL—NH$_2$ (SEQ ID NO:2) or SFLLRN—NH$_2$ (SEQ ID NO:1) (0.1–30 µM).

The time course and mechanism of PAR2 resensitisation were determined in mouse bronchi either left untreated (time control) after acetylcholine washout or treated with trypsin (0.3 U/ml at 2 min intervals) over a period of 20 to 30 min. Tissues were then contracted with carbachol to approximately 40% $F_{max}$ and exposed to trypsin (0.3 U/ml) at 0, 15, 45, 80 or 120 min after washout. Time controls to trypsin in non-desensitised tissues were not different at any of the times examined. The protein trafficking inhibitor, brefeldin A (10 µM) and the protein translation blocker, cycloheximide (70 µM), were then used to explore the mechanism underlying PAR2 resensitisation following desensitisation with trypsin. In these experiments, trypsin-desensitised tissues were either left untreated (control) or treated with brefeldin A or cycloheximide before re-exposure to trypsin (0.3 U/ml) at 45 min.

In Vivo Studies

Male Sprague-Dawley rats (8 weeks) were anaesthetised (xylazine 10 mg/kg, ketamine 100 mg/kg and 50 mg/kg each 30 min thereafter, i.p.) and cannulae were placed in the trachea, carotid artery and jugular vein. Spontaneous breathing was stopped by an intravenous injection of pancuronium bromide (0.4 mg/kg and 0.2 mg/kg each 30 min thereafter) and rats were ventilated (tidal volume 8 ml/kg at 90 breaths/min, SAR-830 ventilator, CWE Inc., Ardmore, USA). Breath-to-breath measurement of airway resistance (RD and dynamic compliance ($C_{dyn}$) were calculated from flow and transpulmonary pressure recordings (PMS800, Mumed, London, UK). Flow was measured over the tracheal cannula (Fleisch pneumotachograph, Lausanne, Switzerland) and transpulmonary pressure was measured with a differential pressure transducer, one end being connected to the outlet of the tracheal cannula, the other to an air-filled cannula inserted in the oesophagus. A rectal probe was used to monitor body temperature. Serotonin (5-HT; 0.3 mg/kg i.v.) was administered as a bolus dose at 5 min intervals until reproducible changes in $R_L$ and $C_{dyn}$ were obtained. Prior to each 5-HT challenge, lungs were hyperinflated once (by delivering twice the tidal volume) to prevent and reverse atelecasis. SLIGRL—NH$_2$ (SEQ ID NO:2), the scrambled peptide LSIGRL—NH$_2$ (SEQ ID NO:4) (both 0.1 mg/ml) and their vehicle controls (saline) were then delivered for 30 sec as aerosols generated by an ultrasonic nebuliser (AeroSonic 5000, DeVilbiss, Somerset, USA) in series with a second ventilator and the response to 5-HT determined 5 min later.

Data Analysis

All cumulative responses (relaxations and contractions) were normalised as percentages of the initial level of active force to carbachol. Results are presented as mean±s.e mean and pEC$_{50}$ (sensitivity) values were calculated by fitting concentration-response curves to a four parameter logistic function (Kemp and Cocks, 1997) using Graphpad Prism (version 2.0). Statistical comparison of mean pEC$_{50}$ and maximum response ($R_{max}$) values were compared by two-tailed unpaired Student's t-tests or one way analysis of variance (ANOVA) with Tukey-Kramer's t-tests for multiple comparisons. P<0.05 was accepted as significant. Unless specified, all averaged data are from n>5 experiments.

Immunohistochemistry Mouse

Fresh frozen, paraformaldehyde-fixed sections (14 µm) of mouse bronchus were incubated with a rabbit antiserum directed against the carboxyl-terminal of mouse PAR2 (CS-VKTSY (SEQ ID NO:5)) at a dilution of 1:500 for 48 h, washed with phosphate-buffered saline (PBS) and then incubated with a biotinylated donkey anti-rabbit antiserum (Amersham) for 2 h, washed again with PBS and then labelled with FITC-conjugated streptavidin (Amersham) all at room temperature. After a final wash in PBS, the sections were mounted in buffered glycerol and viewed under a Biorad MRC1000 confocal scanning laser system installed on an Olympus IMT2 microscope with a krypton/argon taster. Visualisation of FITC was achieved using a 488 nm excitation filter and a 522/535 nm emission filter. Images of 768×612 pixels were then processed using Adobe Photoshop software. No staining was observed when the antiserum was preabsorbed with the immunising peptide sequence (10 µM at 4° C. for 24 h).

Human

Paraffin sections (3 µm) were dewaxed and exposed to the rabbit anti-PAR2 antiserum as described above. After 24 h exposure, a monoclonal mouse antibody directed against human trypsin (ogen) (Chemicon, MAB1482) was also applied. After a further 24 h exposure to both probes, binding of the rabbit antiPAR antiserum was localised as described above, while trypsin(ogen) was localised using a donkey anti-mouse antiserum conjugated to rhodamine. The expression of PAR2 and trypsin(ogen) was examined under epifluorescence using a Ziess Axioskop microscope equipped with separate filters for FITC and rhodamine fluorescence. Photographs were taken on Kodak Ectachome T160 film and subsequently scanned on a Macintosh computer using a slide scanner (Nikon). The separate images of FITC (green) or rhodamine (red) fluoresence were overlayed with Adobe Photoshop software, using obvious reference points to correctly align the images.

EXAMPLE 2

Activation of PAR in Bronchi of the Guinea-Pig and Mouse

Guinea-pigs of either sex (250–300 g) were killed in initial experiments by CO$_2$ asphyxia, and in later experiments by a blow to the head. Where a blow to the head was used, great care was taken to ensure that the airways did not aspirate blood. Mice (Balb/c, male and female, 20–25 g) were killed by cervical dislocation and exsanguination. In both cases, the left and right bronchi were exposed and carefully dissected free from surrounding connective tissue using a dissecting microscope, excised and placed in cold, physiological bicarbonate-buffered Krebs solution of the following composition (in mM): (Na$^+$ 144, K 5.9, Ca$^{2+}$ 2.5, Mg$^{2+}$ 1.2, Cl$^-$ 128.7, HCO$_3^-$ 25, H$_2$PO$_4^-$ 1.2, SO$^{2-}$ 1.2 and glucose 11 (Stork and Cocks, 1994a). This solution was continuously gassed with a mixture of 95% v/v O$_2$, 5% v/v CO$_2$ to maintain pH at 7.4 and adequate pO$_2$ of the solution. An approximately 3 mm long ring was cut from each bronchus. In order to maximize sensitivity, some guinea-pig airways were cut as bronchial spirals, which brings several segments of smooth muscle into series.

For the guinea-pig, the preparations; were suspended vertically on two stainless steel wire hooks in organ baths containing warm (37° C.), gassed Krebs solution. One wire was attached to a micrometer-driven support leg, the other to a forced displacement transducer to record changes in force.

Mouse bronchus preparations were carefully mounted horizontally on fine (40 μm) stainless steel wires attached to the jaws of a Mulvany-Halpem myograph. After 60 min at 37° C., all rings were stretched to 0.5 g passive force, which had been determined in preliminary experiments to be optimal, and allowed to recover from that stretch for a further 30 min. Maximum contraction ($F_{max}$) in each tissue was then determined with exogenously applied acetylcholine (ACh; 30 μM) followed by washout. A further 30 min equilibration time was allowed before the tissues were actively contracted to between 20% and 60% of their individual Fm." values with titrated concentrations of carbachol (10–100 nM). When these contractions maintained steady plateaus, cumulative half-log concentrations or units of enzyme activity of trypsin, thrombin, SLIGRL—$NH_2$ (SEQ ID NO:2)(PAR2-AP), SFLLRN—$NH_2$ (SEQ ID NO:1) (TRAP) prostaglandin E2 ($PGE_2$) and isoprenaline were added. In some cases, tissues were treated with a range of drugs prior to contraction to approximately 50% $F_{max}$. These included the cyclooxygenase inhibitors indomethacin and aspirin, the nitric oxide (NO) synthase inhibitor N'-nitro-L-(L-NOARG), the NO scavenger oxyhaemoglobin (Hb0), and the L-voltage-operated Cat' channel inhibitor nifedipine.

The luminal surface of some rings of bronchi were mechanically abraded with a tapered wooden stick to remove the epithelium. The integrity of the epithelium and underlying smooth muscle, as well as the effectiveness of epithelium removal, were confirmed histologically using 15 μm cryostat sections of the bronchi stained with haemotoxylinleosin.

Whilst it was possible to surgically abrade the epithelium in the guinea pig to test the role of the cells in the PAR2-mediated relaxation response, as described below, many of the animals had large amounts of mucus present in the airways during dissection. Guinea-pigs are not pathogen-free, and an abnormally high amount of mucus can be a sign of airway infection. In view of the inventors' hypothesis that PAR2 might be an intrinsic protective mechanism which may be compromised during airway infection, experiments were therefore designed using specific pathogen-free Balb/c mice. If PAR2 was shown to mediate bronchorelaxation responses in this species, it would then be possible to test whether PAR2 and PAR1 were involved in the pathogenesis of asthma.

Figure 2:
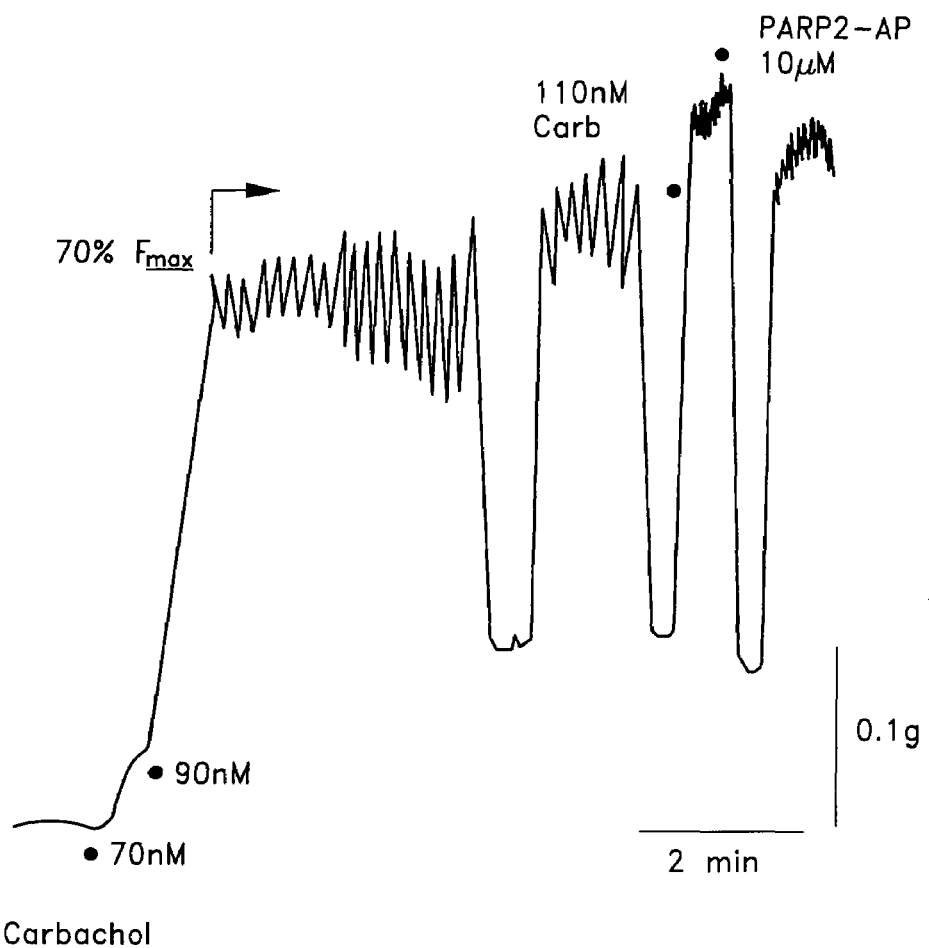
FIG. 2 is a chart recording showing changes in isometric force in a ring of mouse bronchus contracted to approximately 70% maximal force ($F_{max}$) with carbachol. The characteristic spontaneous fluctuations in active force fell markedly, then recovered at two points. After the second fall and recovery, extra carbachol was added to increase the level of active force above 70% $F_{max}$. A high, single concentration of the PAR2 activating peptide, PAR2-AP, (SLIGRL—NH$_2$) (SEQ ID NO:2) then induced a large relaxation.
Figure 3A:
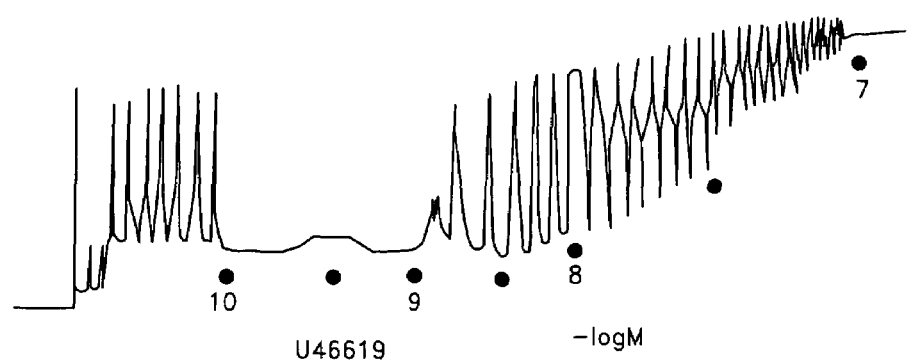
FIGS. 3A–3D show the effect of increasing concentrations of nifedipine (–logM) on spontaneous and contractile agonist-induced phasic contractile activity in isolated ring segments of human large coronary artery. The figures show four rings of coronary artery stretched, twice (arrows) to 5 g resting force, then contracted with cumulatively increasing concentrations of the thromboxane A$_2$ mimetic, U46619 (logM).
Figure 3B:
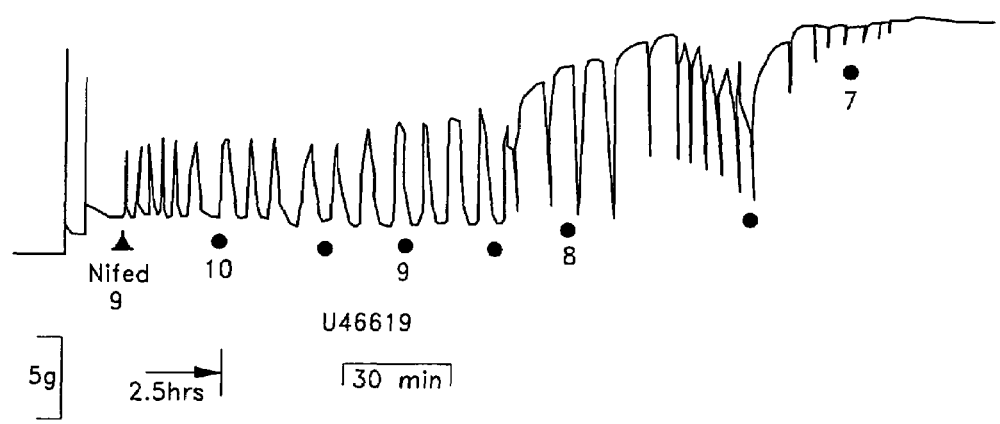
Figure 3C:
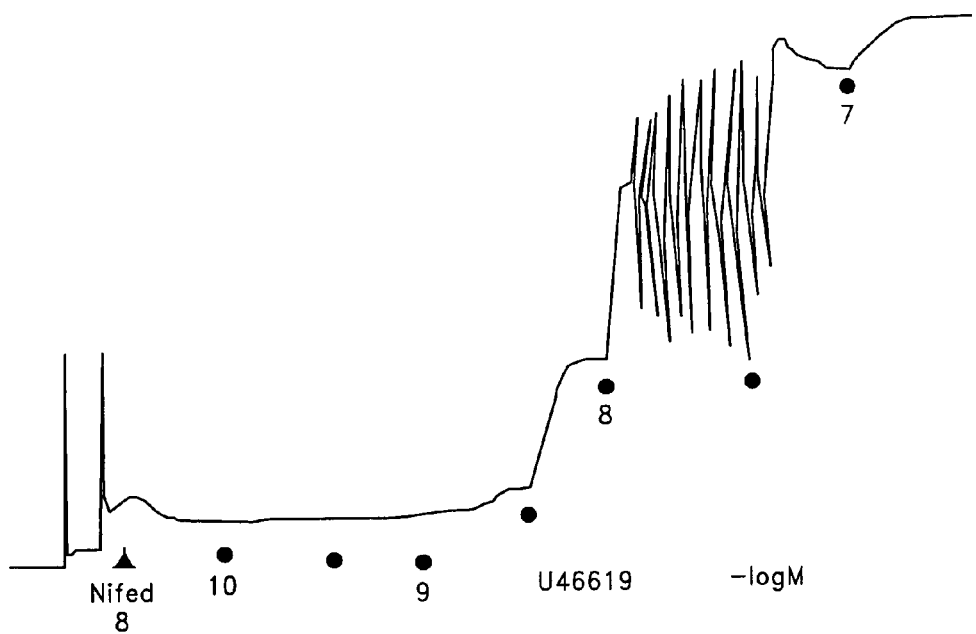
Figure 3D:
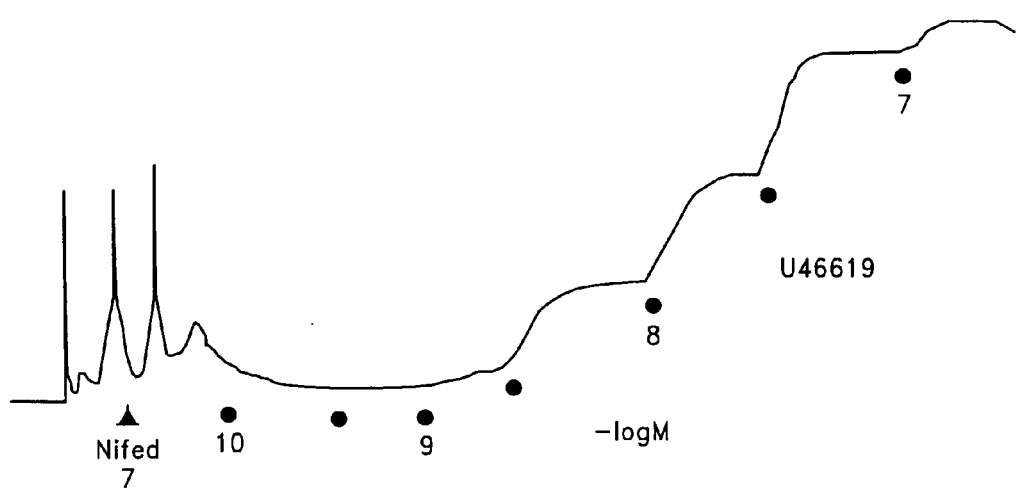
Figure 4:
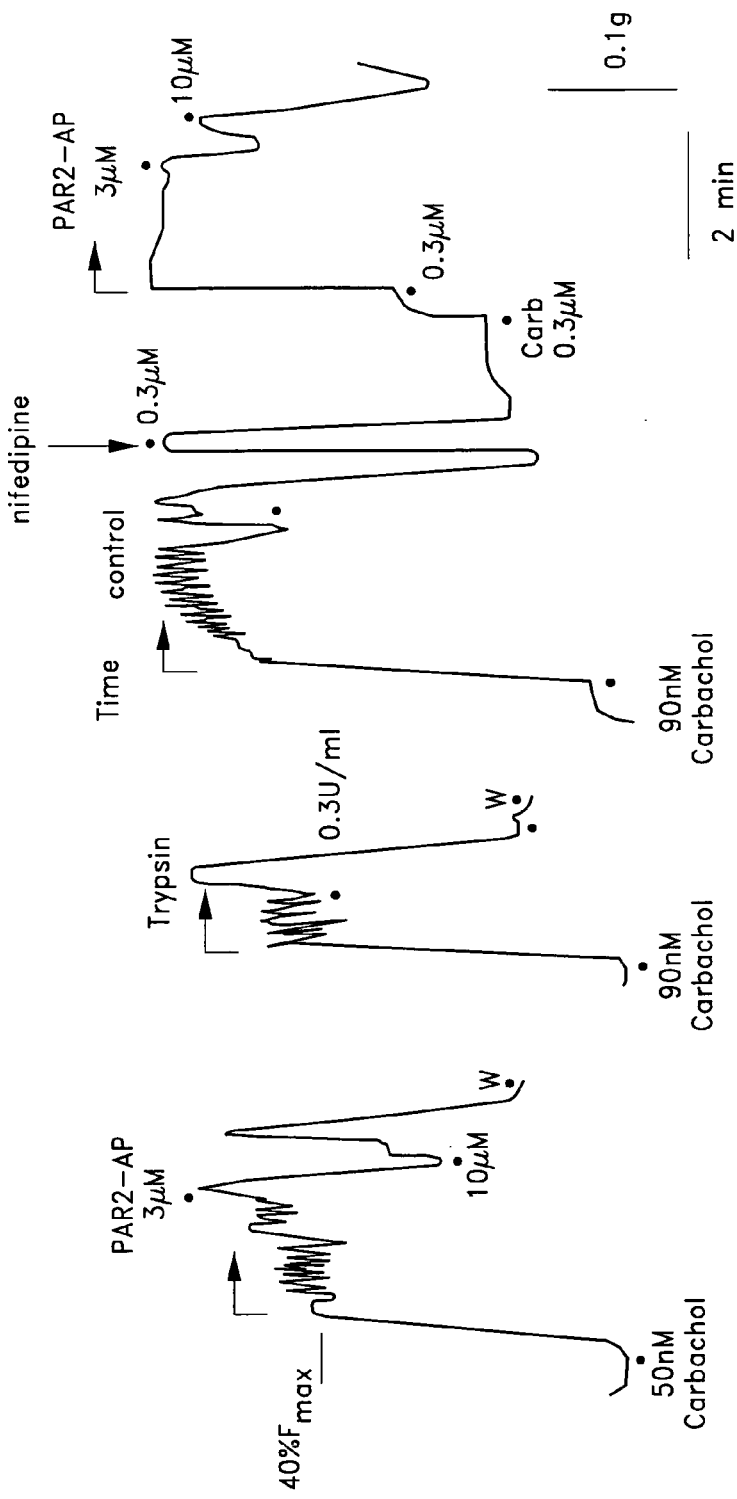
FIG. 4 is a chart recording showing changes in isometric force in a ring of mouse bronchus contracted to 40%–50% $F_{max}$ with carbachol, and the effects of the PAR2 activating peptide, PAR2-AP (SLIGRL—NH$_2$) (SEQ ID NO:2) and trypsin in the absence and presence of nifedipine (0.3 µM).

When bronchial smooth muscle relaxation or contraction mediated by PAR2 and PAR1 in the mouse was investigated, it was found that most preparations developed spontaneous, phasic contractions to carbachol, a cholinergic agonist similar to methacholine, which were superimposed on the tonic 20%–60% $F_{max}$ responses. These contractions were rhythmical, and often of large amplitude. Furthermore, they were maintained far variable times before suddenly returning to near-basal levels of active force, as shown in FIG. 2. This instability, combined with the spontaneous activity, resulted in difficulty in assessing relaxations. It was also difficult to place the contraction to carbachol at a predetermined percentage of $F_{max}$ since it tended to be all-or-nothing until the near-maximum of the curve was reached. However, with maximum concentrations of the relaxing agents, and with appropriate time controls, fast onset and rapid near-maximum relaxations to PAR2-AP were routinely obtained, as shown in FIG. 4.

EXAMPLE 3

Effect of Nifedipine

The effect of the L-type voltage-operated $Ca^{2+}$ channel inhibitor, nifedipine, on the bioassay system for bronchodilators in the mouse was also examined. Results for the human coronary arteries are shown in FIG. 3. Nifedipine (10 nM; see panel D) blocks both the spontaneous contractions and those which develop in response to U46619. Such treatment allows more accurate and valid measurement of relaxations at pre-set levels of now stable active force (Stork and Cocks, 1994a). Nifedipine (0.3 μM) also abolished the phasic contractions of the bronchi to carbachol, and resulted in the maintenance of stable levels of tonic, active force at any predetermined level. These results are shown in FIG. 4. Development of similar spontaneous activity to that shown in FIG. 3 was observed. However, even with such activity present, relaxation in response to both PAR2-AP and trypsin appeared to have occurred since active force remained constant for the time taken to obtain the relaxation to each agonist (see "TIME CONTROL" panel). Nifedipine markedly inhibited the contraction to carbachol, so that higher concentrations were required to restore force to control levels. Under these conditions, however, phasic activity was absent and unequivocal concentration dependent relaxations to PAR2-AP were readily demonstrated. Under these conditions, PAR2-AP routinely caused well defined, concentration-dependent relaxation.

EXAMPLE 4

Effect of Denudation of the Epithelium

Figure 5A:
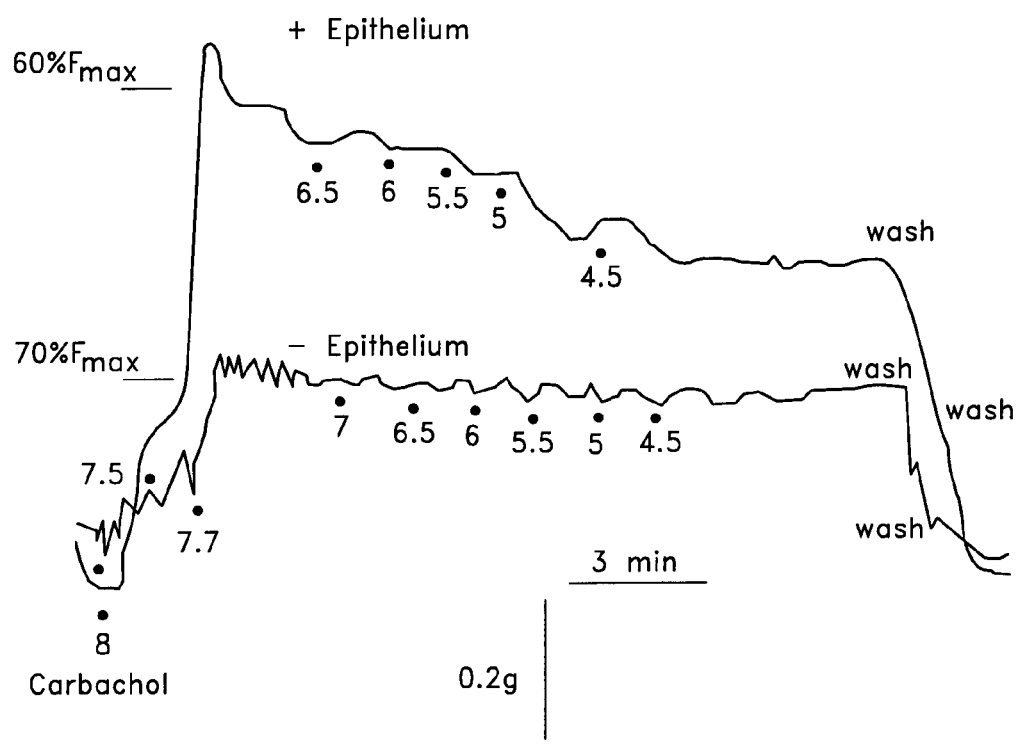
FIGS. 5A and 5B shows the effect of removal of the epithelium on relaxation to the PAR2 activating peptide, PAR2-AP (SLIGRL—NH$_2$) (SEQ ID NO:2) in rings of the guinea-pig isolated bronchus.
Figure 5B:
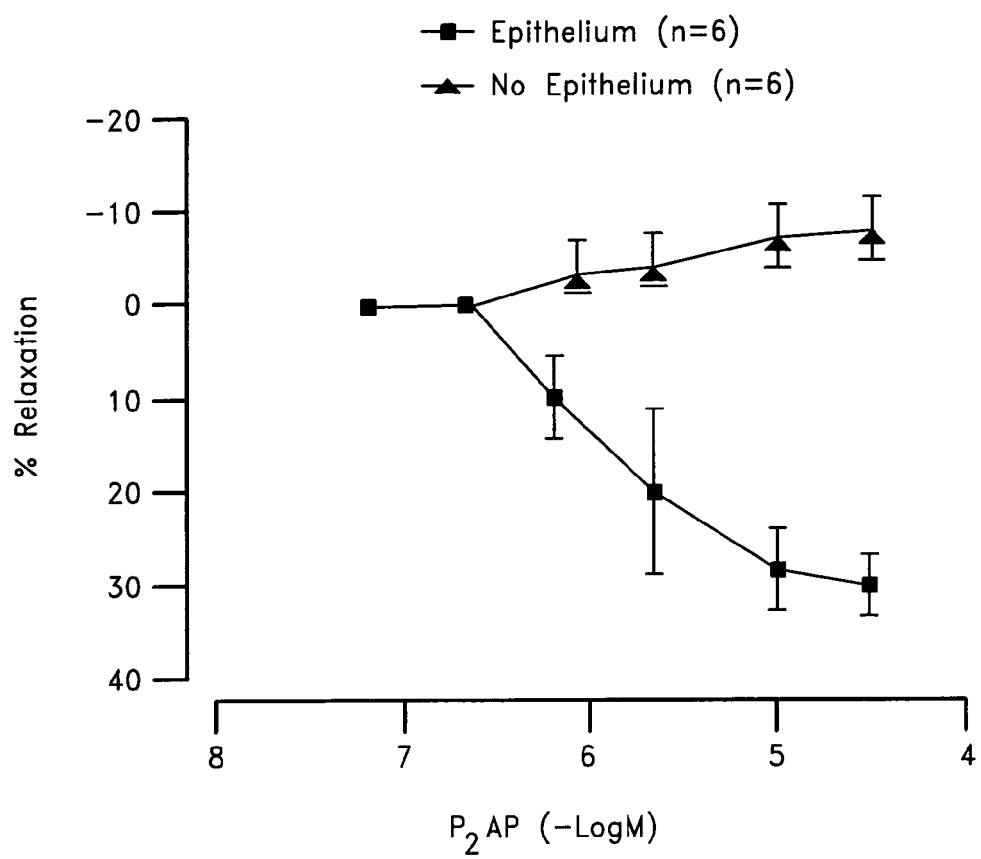
Figure 6:
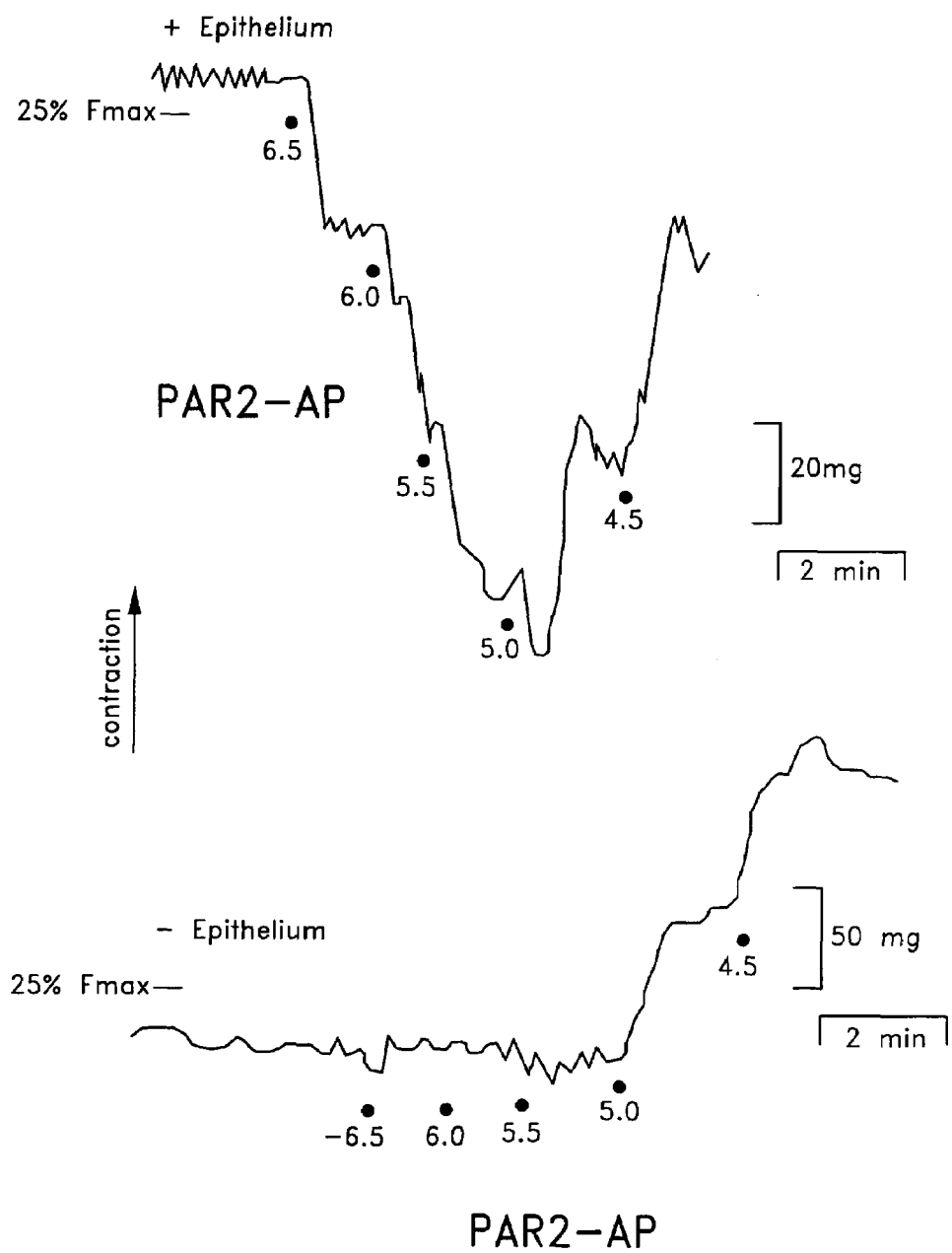
FIG. 6 is a chart recording demonstrating the obligatory role of the epithelium in mediating relaxation to the PAR2 activating peptide, PAR2-AP (SLIGRL—NH$_2$ (SEQ ID NO:2), logM), in isolated spiral strip preparations of the guinea-pig bronchus. Strips were contracted to approximately 25% $F_{max}$ with carbachol.

Whenever attempts to remove the epithelium from mouse bronchi or trachea were made, they invariably damaged the underlying smooth muscle, since all rings treated in this manner failed to contract to ACh. Therefore, studies were conducted using the guinea-pig to obtain information as to the possible role of the epithelium in mediating bronchial smooth muscle relaxation to PARs. Concentration dependent relaxations to PAR2-AP were observed in six out of thirteen bronchial rings in which the epithelium was intact; the remaining seven tissues either gave no response or small contractions to PAR2-AP. In the same number of epithelium-denuded rings (n=6) from animals where PAR2-AP caused relaxation (An=6), PAR2-AP either caused a small contraction or no response, as seen in FIG. 5. In a further experiment where spiral strips rather than rings were used, PAR2-AP caused relaxation which was clearly concentration- and epithelium-dependent, as shown in FIG. 6. The presence and absence of the epithelium was histologically confirmed. SFLLRN—$NH_2$ (SEQ ID NO:1) (TRAP) only caused concentration-dependent contractions, which were unaffected by removal of the epithelium.

EXAMPLE 5

Mediators of Epithelium-Dependent Broncho-Relaxation

Figure 7:
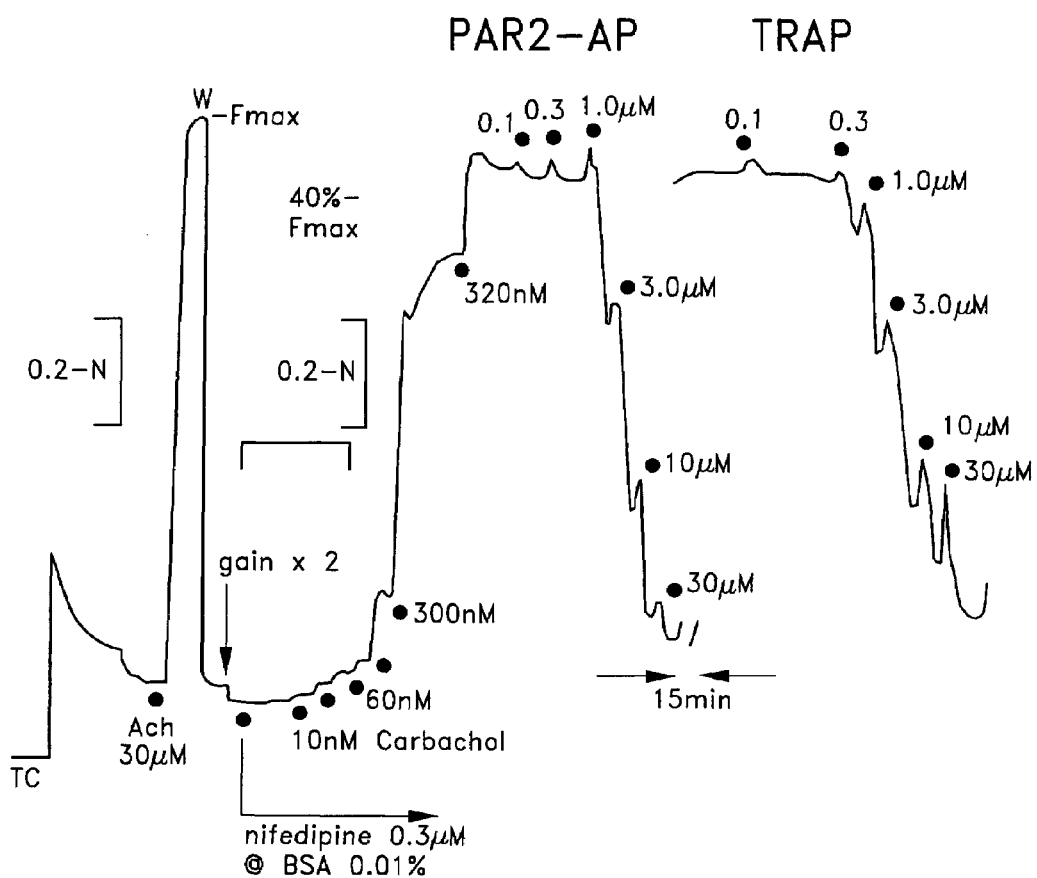
FIG. 7 shows chart recordings depicting both the technique used to record relaxation in isolated mouse bronchial ring preparations, and the efficacy of the PAR2 activating peptide, PAR2-A P (SLIGRL—NH$_2$) (SEQ ID NO:2) and thrombin receptor activating peptide, TRAP SFLLRN—NH2 (SEQ ID NO:1) as broncho-relaxant agents. The time calibration bar represents 40 min, 12 min and 4 min during the $F_{max}$ contraction, the 40% $F_{max}$ contraction with carbachol and the additions of both peptides, respectively.
Figure 8A:
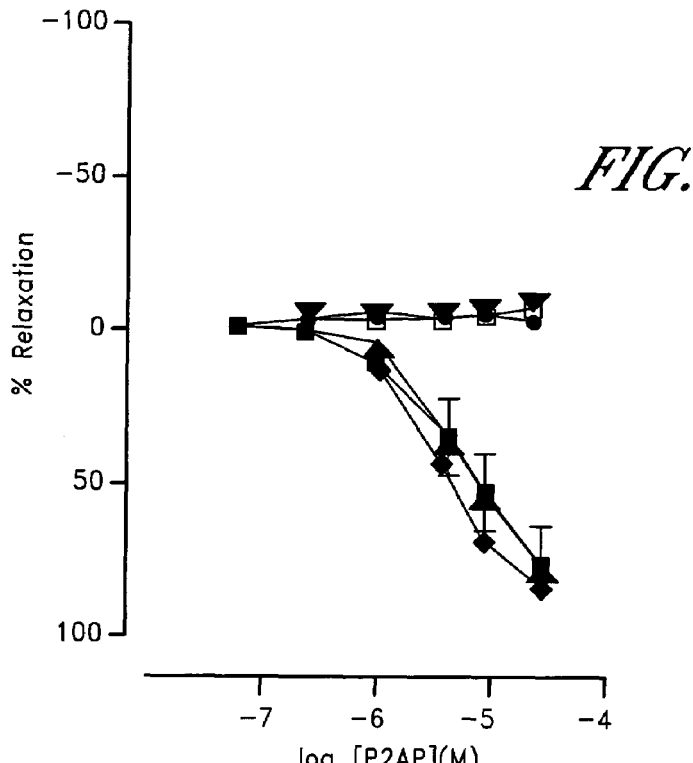
FIG. 8A depicts the sensitivity and maximum relaxation to SLIGRL—NH$_2$ (SEQ ID NO:2), (PAR2-AP) in isolated mouse bronchial rings with epithelium and the effect of potential inhibitors of these responses.
Figure 8B:
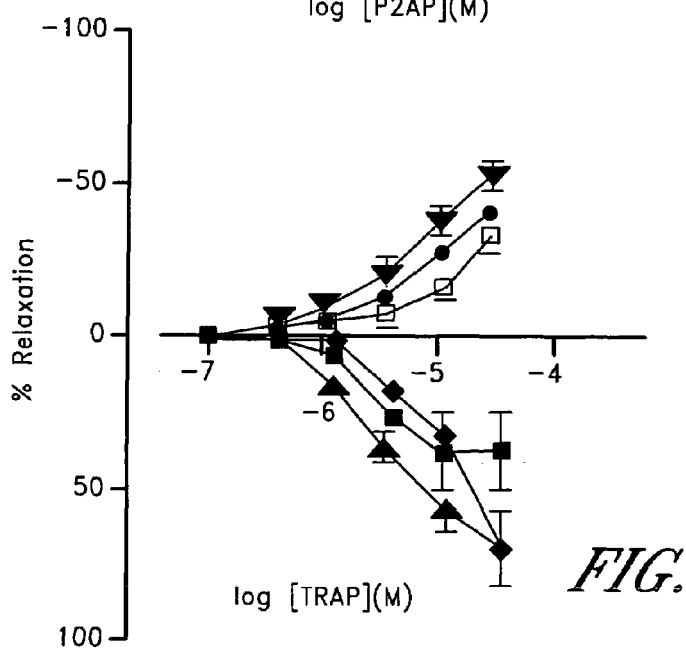
FIG. 8B depicts the sensitivity and maximum relaxation to SFLLRN—NH$_2$ (SEQ ID NO:1) (TRAP) in isolated mouse bronchial rings with epithelium and the effect of potential inhibitors of these responses.
Figure 8C:
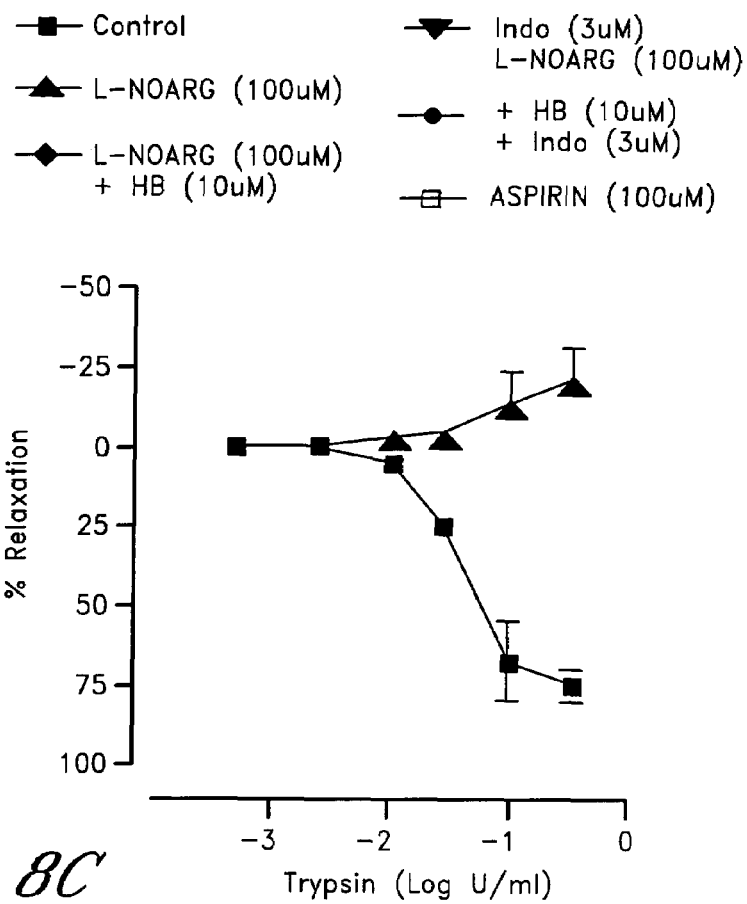
FIG. 8C depicts the sensitivity and maximum relaxation to trypsin in isolated mouse bronchial rings with epithelium and the effect of potential inhibitors of these responses.
Figure 8D:
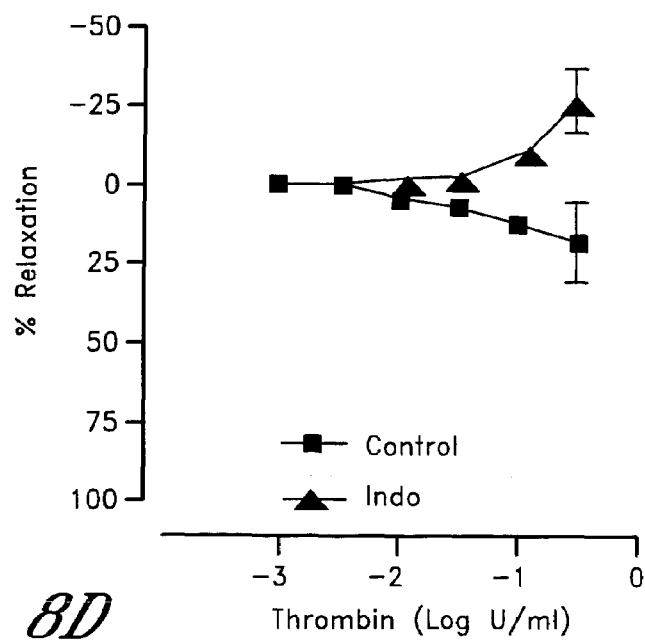
FIG. 8D depicts the sensitivity and maximum relaxation to thrombin in isolated mouse bronchial rings with epithelium and the effect of potential inhibitors of these responses. All responses are expressed as percentage relaxation of the initial levels of active force induced by carbachol (30%–60% $F_{max}$). Values are mean±SEM from 6–9 experiments and positive values represent contractions. Drugs used were L—NOARG (100 µM), a nitric oxide (NO) synthase inhibitor; HbO, (oxyhaemoglobin, 20 µM), a NO scavenger, and Indo (indomethacin, 3 µM) or aspirin (100 µM), both of which are cyclooxygenase inhibitors which prevent the synthesis of prostaglandin.
Figure 9:
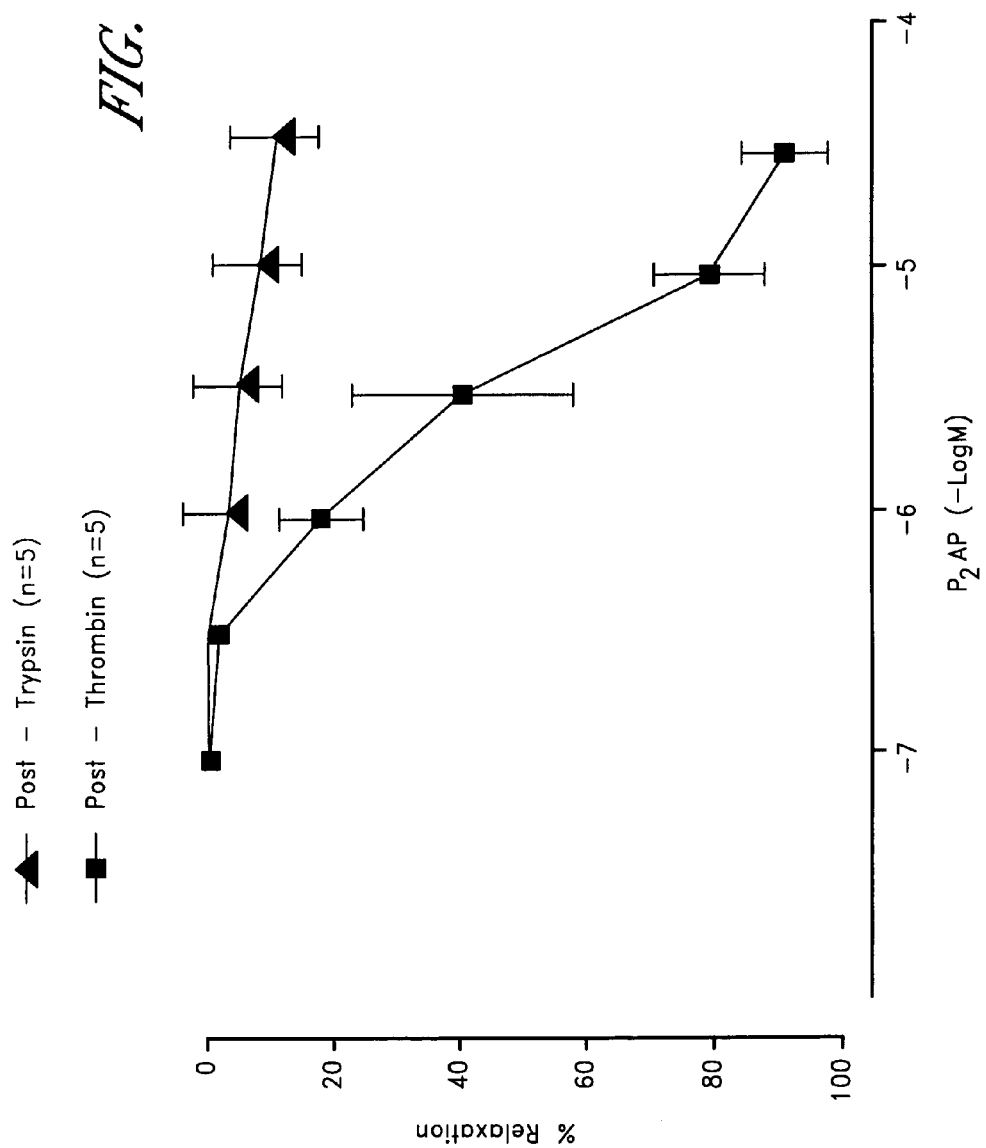
FIG. 9 shows the effect of desensitisation to trypsin (post-trypsin) and thrombin (post-thrombin) on the relaxation to PAR2-AP in ring preparations of isolated mouse bronchi. All responses are expressed as percentage relaxation of the initial levels of active force induced by carbachol (30%–60% $F_{max}$). Values represent mean±SEM from 5 experiments.
Figure 10:
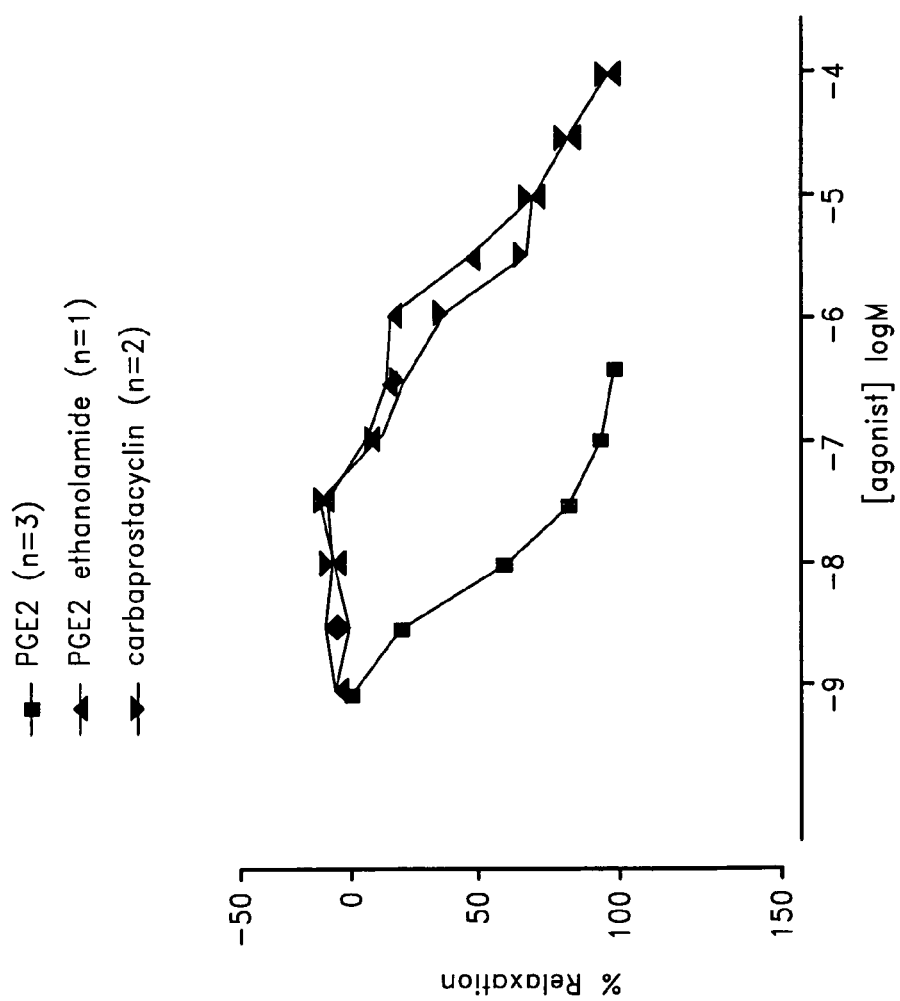
FIG. 10 depicts the sensitivity and maximum relaxation to authentic prostaglandin E$_2$ (PGE$_2$), a stable analogue of PGE$_2$, PGE$_2$ ethanolamide and a stable analogue of prostacyclin (PG12), carbaprostacyclin, in ring preparations of mouse isolated bronchi. Values are mean±SEM from the number of experiments (n) shown in parentheses, and are expressed as percentage relaxation of the initial level of active force induced by carbachol (30–60% $F_{max}$).

FIG. 7 shows how isolated mouse bronchi were set up to measure relaxation sensitively. After an initial passive stretch to 0.5 g (Ti) and recovery, each ring was contracted with acetylcholine (Ach; 30 μM). The contraction was taken as the tissue maximum and referred to as $F_{max}$. After washout (w) and recovery, the tissue was then contracted to approximately 40% $F_{max}$ with titrated, cumulative concentrations of carbachol, resulting in a change in gain. When the contraction to carbachol reached a stable plateau, cumulative, half-log molar concentrations of PAR2-AP and TRAP were added. The results demonstrate that both PAR2-AP and SFLLRN—NH$_2$ (SEQ ID NO:1) (TRAP) caused powerful concentration dependent relaxations in this preparation. These responses were unaffected by the combined treatment with the NO blockers L—NOARG (100 μM) and HbO (20 μM), but were abolished by the cyclooxygenase inhibitors indomethacin (3 μM) and as pirin (100 μm), as shown in FIG. 8. TRAP was less effective as a mediator of relaxation, and responses to this ligand were converted to concentration-dependent contractions by indomethacin and aspirin. This effect was partially blocked by L—NOARG and HbO, as seen in FIG. 8. Under the same bioassay conditions, trypsin cause activity-dependent relaxation which, as for PAR2-AP, was also blocked by indomethacin. By contrast, thrombin caused only poor indomethacin sensitive relaxation at high concentrations which, like TRAP, were converted to contractions by indomethacin. These results are shown in FIG. 8. Continual exposure of the mouse bronchi to high cumulatively increasing concentrations of PAR2-AP (up to 100 μM) for 2h allowed by washout had no effect on the sensitivity or maximum response to subsequent addition of PAR2-AP. All occurrences of relaxation were due to an indomethacin- and aspirin-sensitive mechanism, with no role for NO. Indomethacin and aspirin also converted the relaxation in response to SFLLRN—NH$_2$ (SEQ ID NO:1) (TRAP) to a contraction. Thrombin gave little or no relaxation in the absence of indomethacin, but like TRAP caused a contraction in its presence. In contrast, the response to PAR2-AP was virtually abolished after continual exposure of the tissue to a maximum concentration of trypsin, but not thrombin, as shown in FIG. 9, indicating that trypsin and PAR2-AP activated the same receptor-PGE$_2$ caused potent and maximum relaxation of the mouse bronchi, as shown in FIG. 10.

EXAMPLE 6

Turnover of PAR2

Turnover mechanisms are critical regulators for cells to maintain their responsiveness to PAR-activating enzymes. Therefore, if PARs are to be effective mediators of bronchoprotection, they should be rapidly replaced by new receptors once enzymically cleaved. The inventors examined turnover of functional PAR2 in the mouse bronchi since, unlike PAR1, they were purely inhibitory.

Figure 11A:
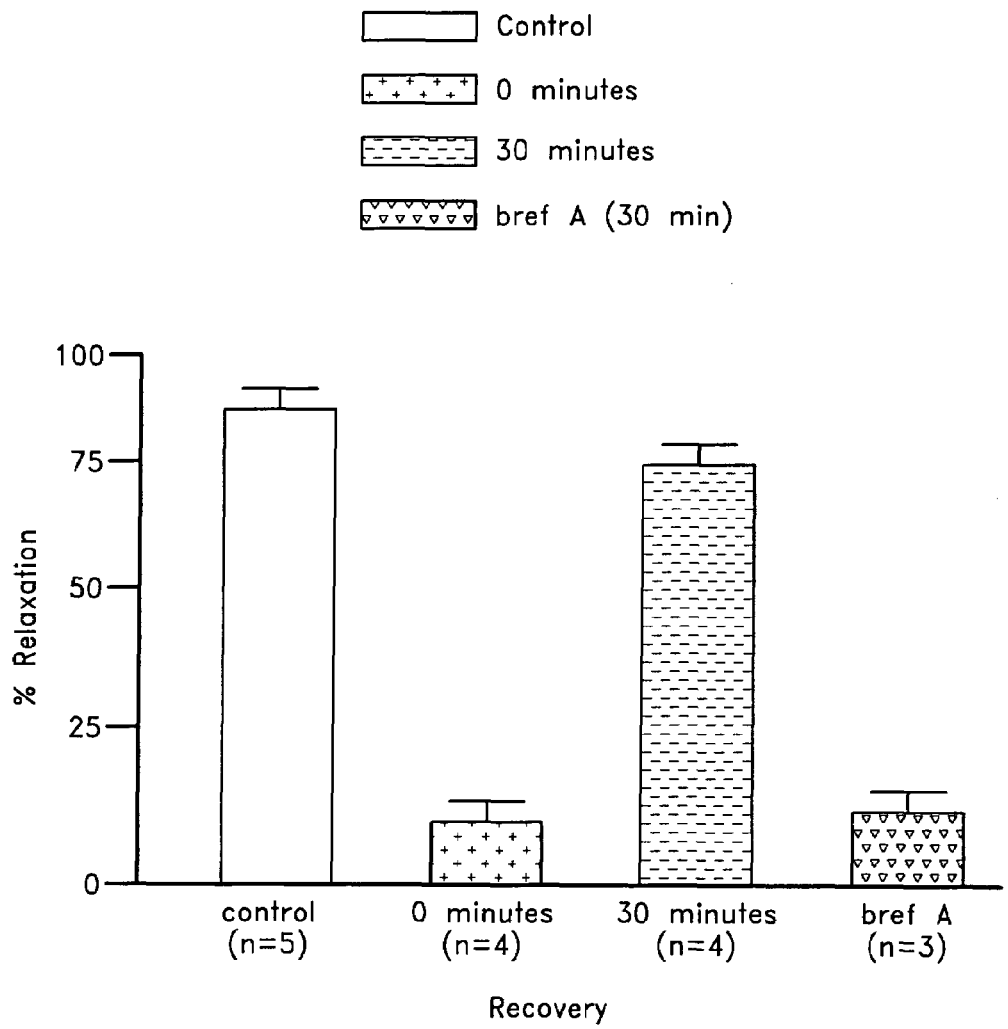
FIG. 11a shows the near-complete and rapid recovery of PAR2-mediated relaxation to trypsin following desensitization to trypsin (Ø i.e. "zero") in ring preparations of isolated mouse bronchi. This recovery (30 minutes) was abolished by the protein trafficking inhibitor, brefeldin A (10 µm). All responses are expressed as percentage relaxations of the initial levels of active force induced by carbachol (30–60% $F_{max}$). Values are mean±SEM from the number of experiments (n) shown in parentheses.
Figure 11B:
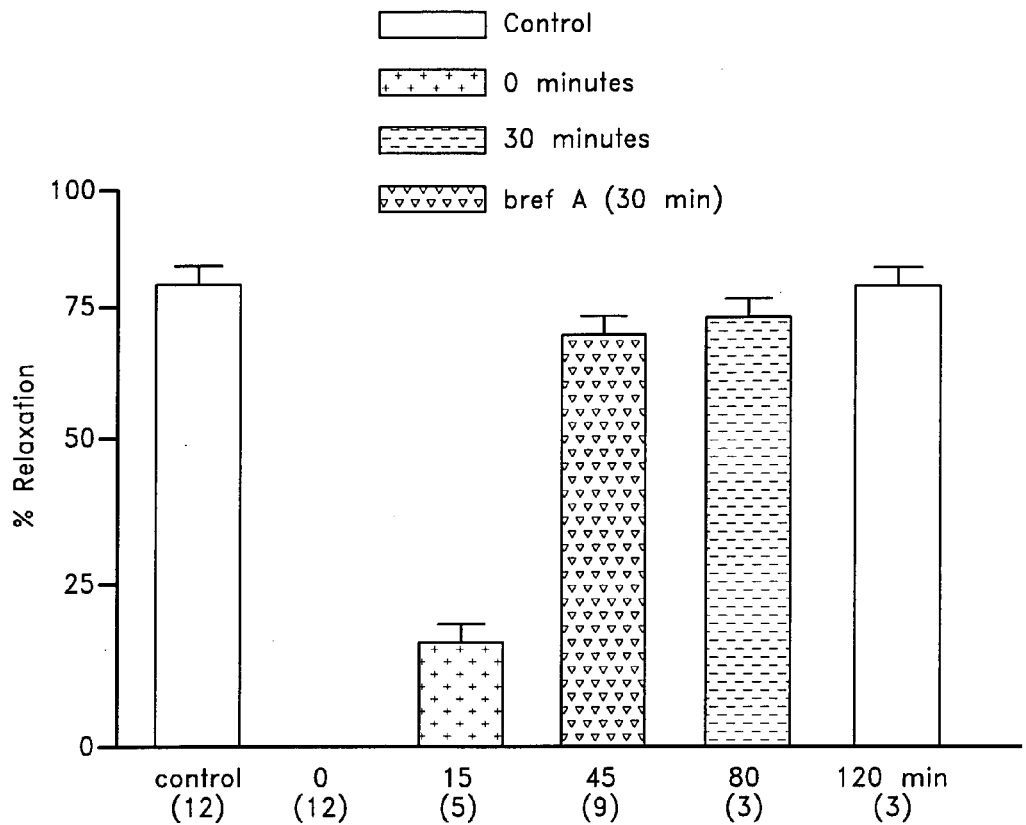
FIGS. 11B and 11C show results of a second experiment demonstrating that epithelial PAR2 receptors in mouse bronchi are regulated by a rapid turnover following desensitisation to trypsin. (11B) Responsiveness to trypsin (0.3 U/ml) recovered to approximately 70% of control at 45 minutes from the zero recovery time (the time at which trypsin caused no response after the desensitising concentration of trypsin 0.3 U/ml) was washed from the bath; see Examples). Time control responses to trypsin at 15, 45, 80 and 120 minute recovery were not significantly different from the initial control. (11C) The recovery of trypsin sensitivity at 45 minutes was abolished by the protein trafficking inhibitor, brefeldin A (10 µM) and the translation inhibitor cycloheximide (70 µM). Both compounds had no effect on time control responses to trypsin. Values are mean ± s.e. mean from 3–12 experiments (shown in parentheses). (p<0.01).
Figure 11C:
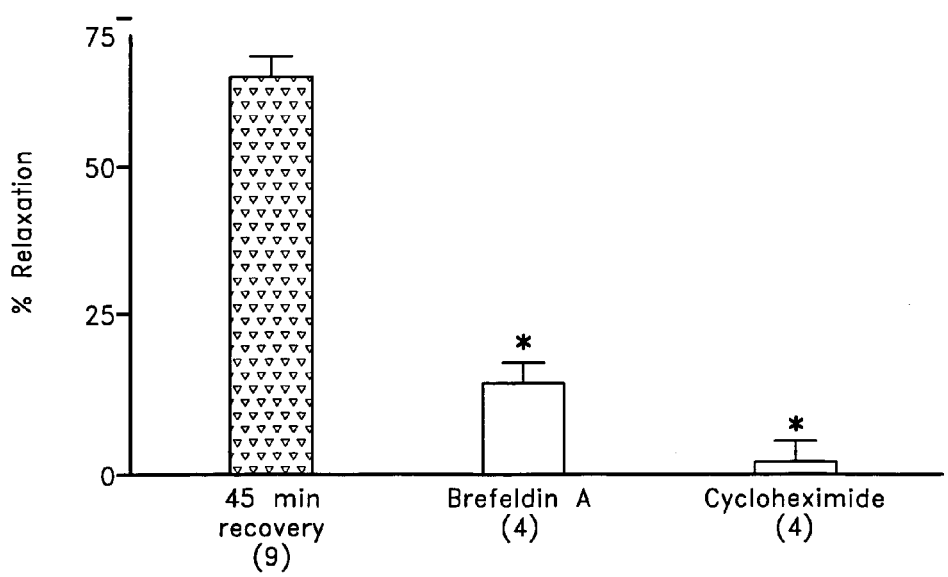

Mouse bronchi were prepared as described in Example 1. Recovery of PAR2-mediated relaxation to trypsin following desensitization to the compound was then measured. The results, presented in FIGS. 11a and 11B and C, showed that bronchial PAR2s were replaced very rapidly following activation with trypsin. Thus, in each experiment, complete recovery of maximum relaxation to 5 trypsin occurred 30 min after an initial desensitising concentration of trypsin. This recovery was abolished by the protein trafficking inhibitor brefelden A(10 μM) or the protein synthesis inhibitor cyclobeximide. The data show that PAR2s were rapidly replaced after activation with trypsin, since relaxation to trypsin returned to near-control levels within 45 minutes after the tissue was desensitised to trypsin. This complete and rapid recovery was abolished by the protein trafficking inhibitor, brefeldin A (10 μM) and the translation inhibitor, cycloheximide (70 μM; FIG. 11C). Equally rapid turnover of cloned PAR2 expressed in selected cell lines has been shown to be dependent on both de novo synthesis of new protein as well as trafficking of preformed receptors from intracellular pools. These data imply that new, fully intact PAR2s are vital for normal functioning of the airways.

EXAMPLE 7

PAR-Mediated Airway Relaxation Occurs in Rats and Pigs

Figure 14:
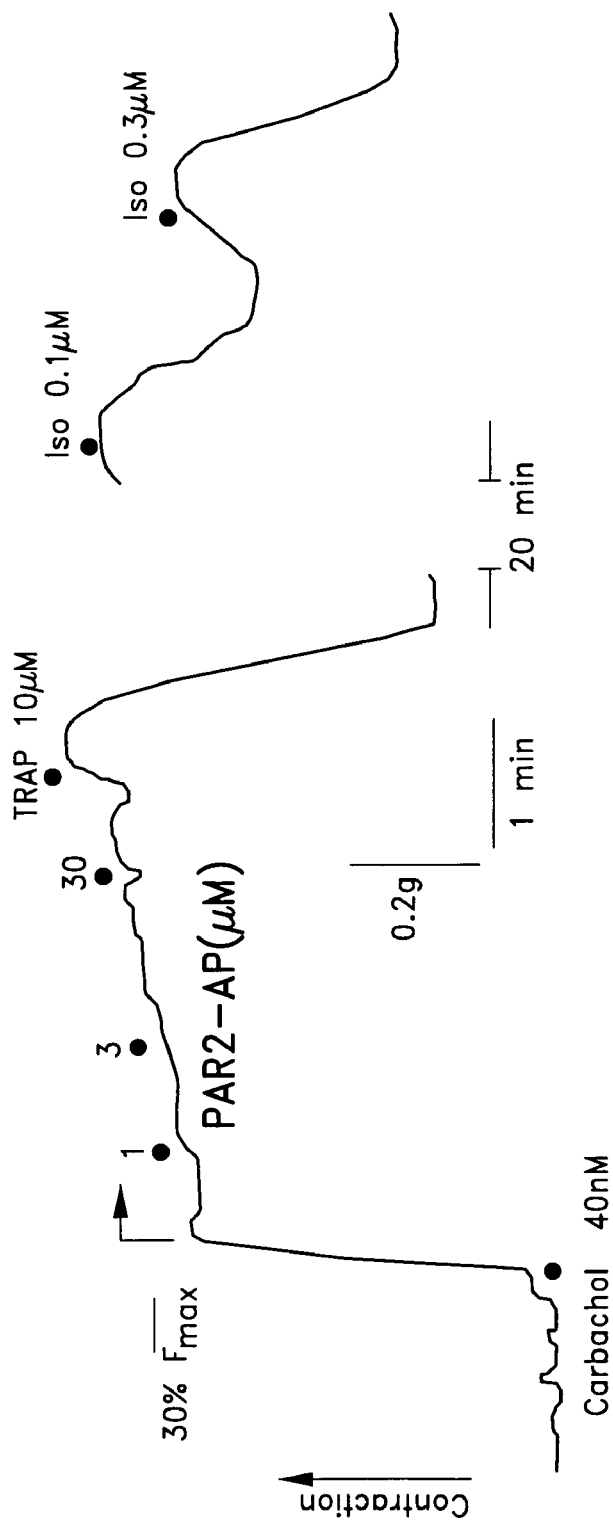
FIG. 14 depicts chart recordings showing the relaxation to the PAR1-activating peptide SFLLRN—NH$_2$ (SEQ ID NO:1) (TRAP), but not the PAR2-activating peptide, SLIGRL—NH$_2$ (SEQ ID NO:2) (PAR2-AP), in an isolated strip of epithelium-containing pig tracheal smooth muscle. SFLLRN—NH$_2$ (SEQ ID NO:1) (TRAP) caused a slow relaxation to near maximum to that of isoprenaline, which showed a similar slow time course. The tissue was contracted to approximately 30% of its maximum contraction to acetylcholine ($F_{max}$) with carbachol. During the break in the trace (20 min), the tissue also recovered its 30% $F_{max}$ level of active force spontaneously without washout.
Figures 15A, 15B:
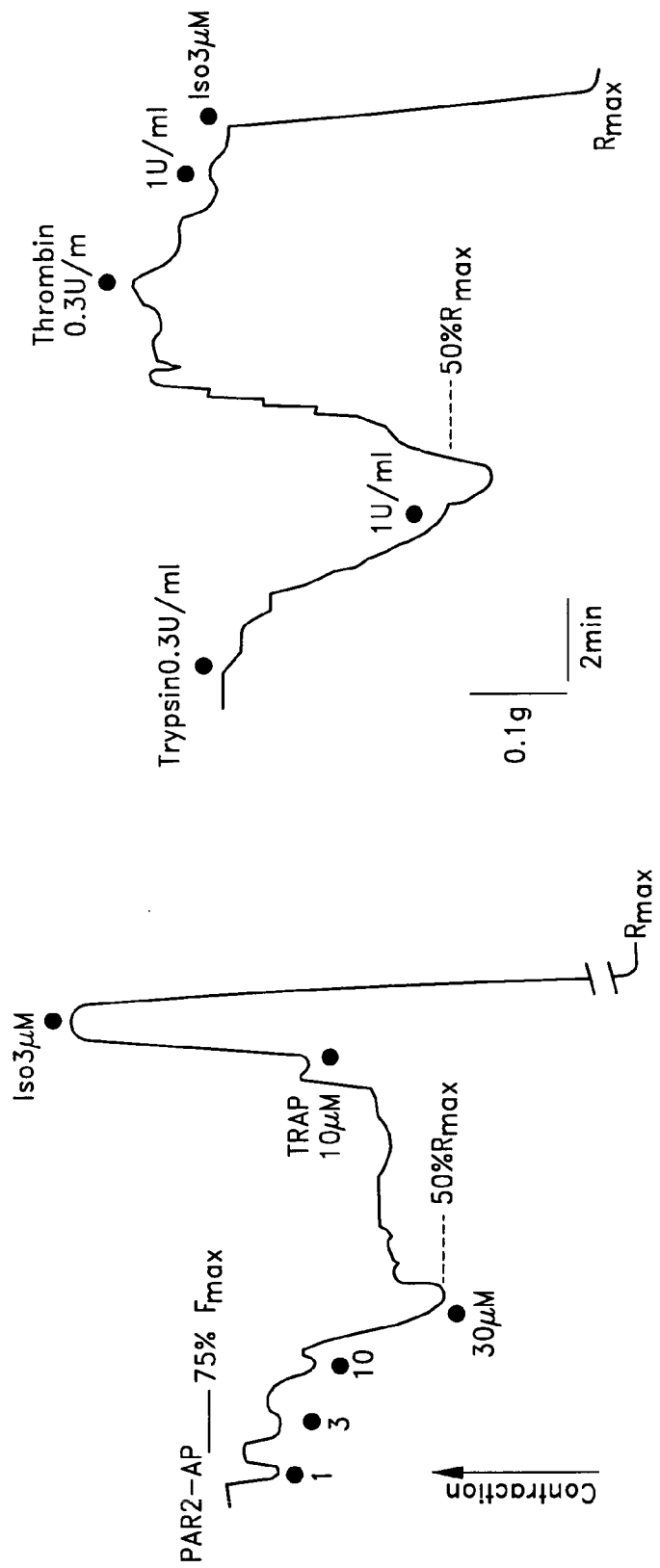
FIG. 15A depicts chart recordings showing relaxation to PAR2 activating peptide (PAR2-AP) or SLIGRL—NH$_2$ (SEQ ID NO:2).
FIG. 15B depicts chart recordings showing relaxation to trypsin in two isolated ring preparations of the rat bronchi with intact epithelium. In each case, the tissue was contracted to 50%–70% of their maximum contraction ($F_{max}$) to acetylcholine (30 μM). $R_{max}$ represents the maximum relaxation to isoprenaline.

The airways of both rats and domestic pigs also relaxed when PARs were activated, as shown in FIGS. 14 and 15. Pig tracheal muscle strips of approximately 2 mm×2 mm in size and with mucosa were prepared by dissecting away overlying cartilage. Strips were suspended in Krebs solution under 1 g passive tension, and contracted to approximately 30% maximal contraction with carbachol (40 μM). The PAR1 activating peptide TRAP, but not the PAR2 activating peptide, PAR2-AP, produced slow onset, near maximal relaxation of the tissue comparable in extent to that induced by isoprenaline, as indicated in FIG. 14.

Bronchi from Male Sprague-Dawley rats prepared as rings in the same way as for mouse bronchi produced results that were qualitatively similar to those observed in the mouse, as indicated in FIG. 15. The PAR1 activating peptide SFLLRN—NH$_2$ (SEQ ID NO:1) (TRAP) only caused a contraction, whereas thrombin caused a small relaxation.

These observations show that the bronchodilatory principle is general, and the inventors have demonstrated this in four species, including two phylogenetically-related species (mouse and rat) and two more distantly-related species, the guinea-pig and domestic pig. As shown in Example 10, these findings also extend to human airways.

EXAMPLE 8

PAR Mediated Relaxation Occurs in Non-Airway Tissue, and can Utilize Effector Mechanisms Different to those in the Mouse Bronchus (A) Guinea-Pig Taenia Coil 2 cm strips of teania coil with intact Auerbach's plexus, but which had been stripped of the mucosa, were suspended in Kreb's solution under 1 g passive tension, and contracted with histamine (1 μM) to induce active tension.

Figures 16A, 16B, 16C, 16D:
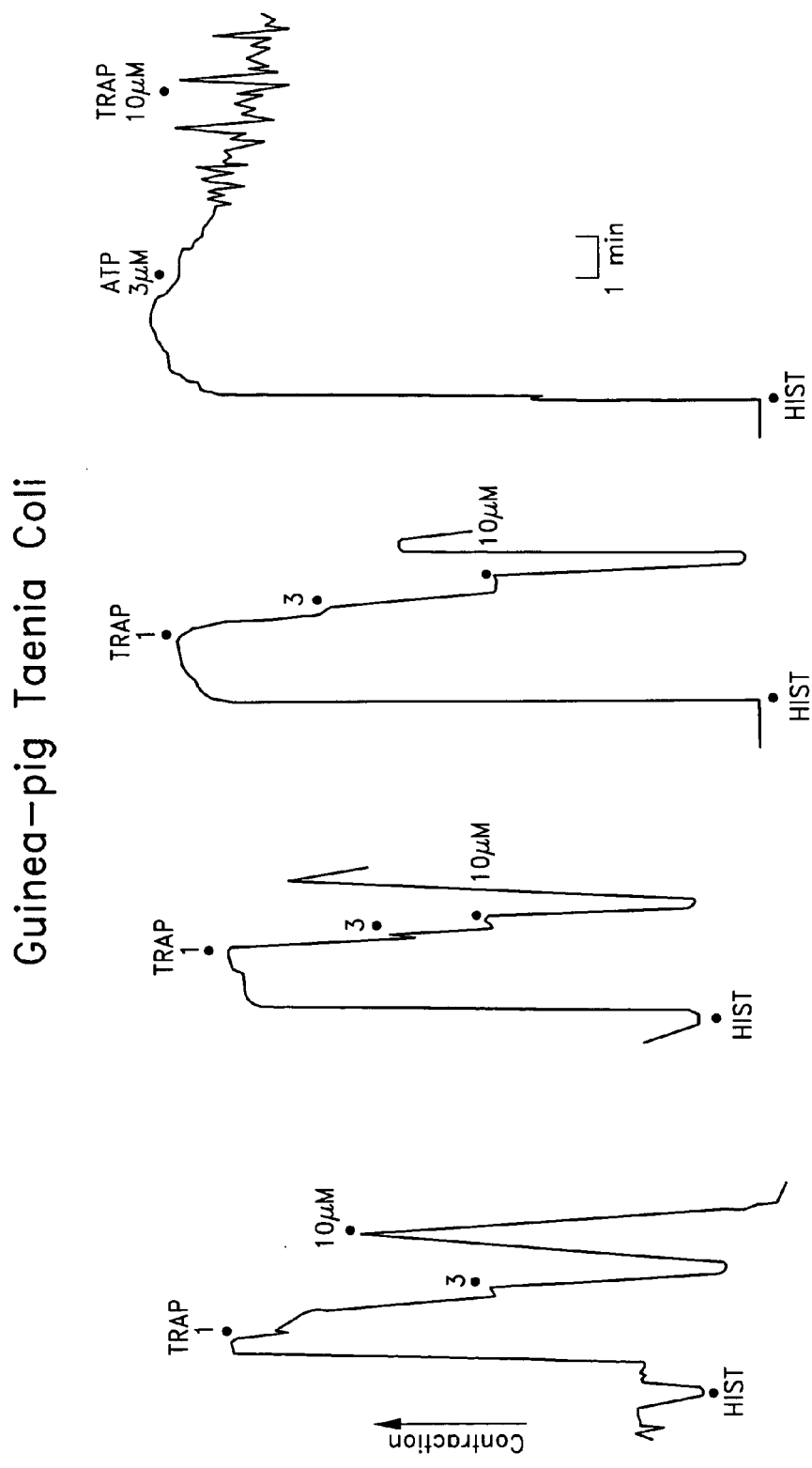
FIGS. 16A–16D depict chart recordings showing relaxation to the PAR1 activating peptide SFLLRN—NH$_2$ (SEQ ID NO:1) (TRAP) in a single preparation of the guinea-pig isolated taenia coli, which initially contracted repeatedly with histamine (HIST; 1 μM) to stable, submaximal levels of active force. At the breaks in the trace, the preparation was washed thoroughly and left to recover for approximately 30 min prior to the next contraction with histamine. (A), control; (B), after treatment with propranolol (1 μM) and prazosin (1 μM) to block any relaxant adrenoceptors; (C), as for (B) except the NO synthase inhibitor, L-NOARG (100 μM), was added as well; (D) as for (C) except the small conductance, $Ca^{2+}$-activated K+ channel (SK) inhibitor, apamin (0.1 μM), was added as well.

This tissue relaxed in response to TRAP in a concentration-dependent manner. The relaxation was not suppressed by the cyclooxygenase inhibitor indomethacin (3 μM), the nitric oxide (NO) inhibitor L—NOARG (100 μM), the beta-adrenoceptor antagonists propranolol (1 W) or the α-adrenoceptor antagonist prazosin (1 μM), thus precluding prostaglandin, NO, and adrenergic mechanisms. However, the relaxation was inhibited by pre-treatment with the small conductance Ca4 activated potassium channel (SK) inhibitor, apamin (100 μM), as shown in FIG. 16. There was no relaxation to ATP in the presence of apamin, indicating the selectivity of apamin for SK channels. These data indicate that the PAR-activated protective mechanism can couple to several response transduction systems, and is not limited by the availability of cyclooxygenase metabolism. The exact mediator of the apamin sensitive relaxation in this tissue is unknown, but candidates include the neuropeptides PACAP and VIP and the purine ATP, which are thought to directly or indirectly open SK channels that mediate relaxation.

(B) Rat Gastric Fundus

Longitudinal strips of gastric fundus from male Sprague-Dawley rats were suspended under 1 g passive isometric tension in Krebs solution.

Figure 17:
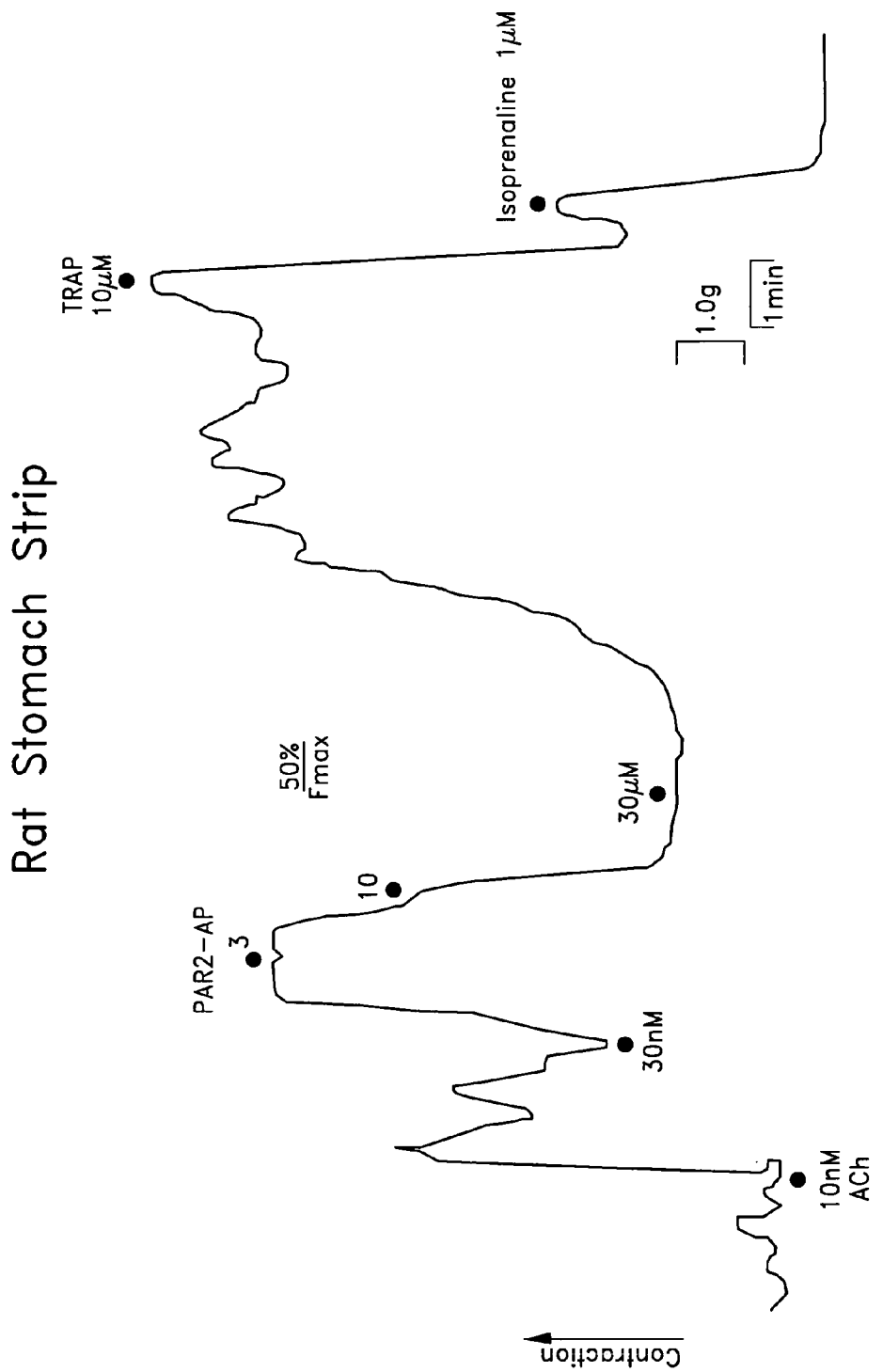
FIG. 17 is a chart recording showing relaxation to the PAR2 activating peptide (PAR2-AP or SLIGRL—NH$_2$ (SEQ ID NO:2) and the PAR1 activating peptide SFLLRN—NH$_2$ (SEQ ID NO:1) (TRAP) in an isolated strip of rat gastric fundus in which the mucosa was left intact. The tissue was contracted to approximately 50% of its maximum contraction to KCl (50 mM) with acetylcholine (Ach). Isoprenaline was added to obtain maximum relaxation.

This tissue related to both PAR1 and PAR2 activating peptides, as shown in FIG. 17.

(C) Human Distal Colon

Human distal colon strips obtained at bowel resection were suspended at 1 g passive isometric force and contracted with substance P (30 µM) to maintain a steady level of active tension.

Figure 18:
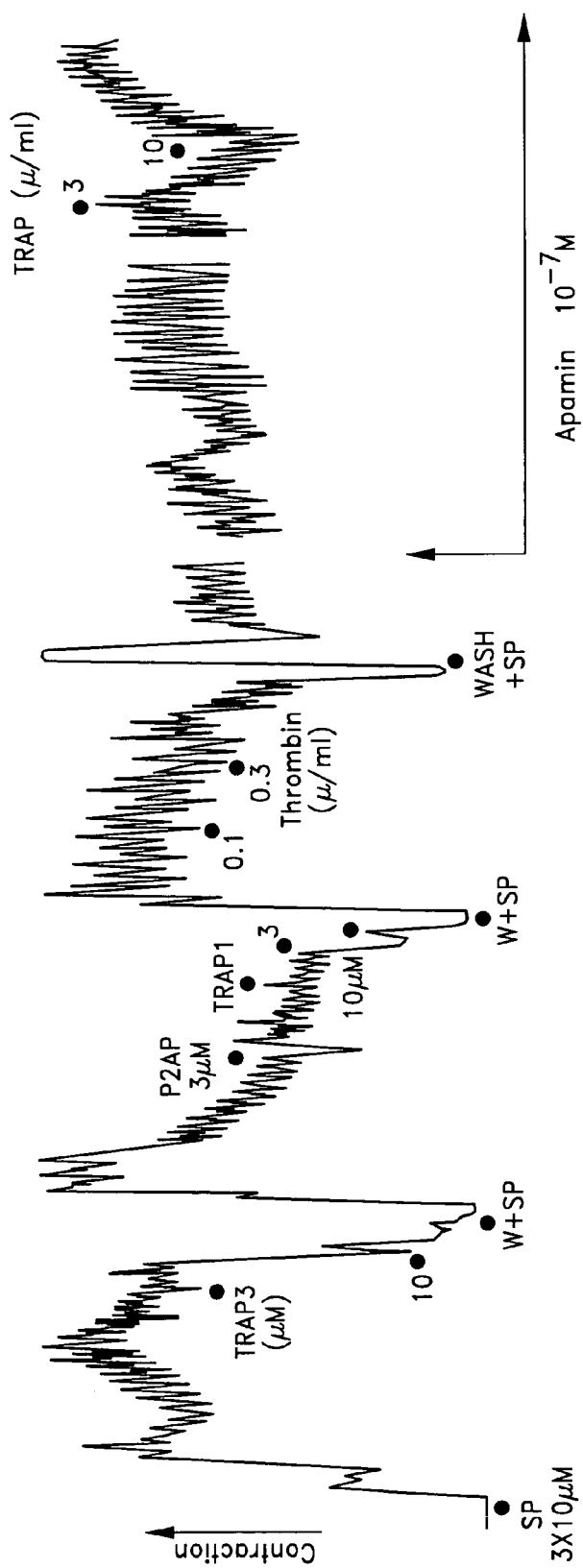
FIG. 18 is a chart recording showing the relaxation to the PAR1 activating peptide SFLLRN—NH$_2$ (SEQ ID NO:1)or TRAP) [and to a smaller extent, PAR2-AP or SLIGRL—NH$_2$(SEQ ID NO:2) in an isolated strip of longitudinal muscle of the human distal colon. The preparation was contracted to a stable level of active force with repeated additions of substance P(SP, w=wash). The breaks in the trace represent 10–15 min. Apamin was left in contact with the preparation for more than 30 min.

This tissue relaxed in an apparently apaminin sensitive manner to SFLLRN—NH$_2$ (SEQ ID NO:1) (TRAP) and to a lesser extent PAR2-AP. Thrombin, however, did not result in relaxation in this tissue, as depicted in FIG. 18.

EXAMPLE 9

PAR-Mediated Relaxation in Human Coronary Arteries

Human distal right coronary arteries (2–3 mm o.d.) were obtained from the explanted hearts of nine patients undergoing heart transplantation at the Alfred Hospital, Melbourne, Australia. Six patients were diagnosed with end-stage dilated cardiomyopathy, two with congenital septal defects and one with ischaemic heart disease.

Arteries were isolated immediately after explantation and transported to the laboratory in ice-cold Krebs solution (composition (mM): Na$^+$ 144, Cl$^-$ 128.7, HCO$_3^-$ 25, K$^+$ 5.9, Ca$^{2+}$ 2.5, Mg$^{2+}$ 1.2, H$_2$PO$_4^-$ 1.2, SO$_4^{2-}$ 1.2 and glucose 11). 3 mm ring segments, some with the endothelium removed by abrasion of the luminal surface with a filer paper taper moistened with Krebs solution, were mounted between two parallel, stainless steel wire hooks in 30 ml organ baths containing Krebs solution maintained at 37° C. and continuously bubbled with 95% v/v O$_2$, 5% v/v CO$_2$, One hook was attached to a micrometer-adjustable support leg and the other to an isometric force transducer (Grass Instruments, model FT03C) to record changes in isometric, circumferential force which were amplified and displayed on flat bed chart recorders (W & W Scientific Instruments).

Following a 60 min equilibration period, passive force (5 g) was applied to the artery rings, which were then allowed to recover for 30 min before again being stretched to 5 g. After a further 30 min, rings were exposed to 125 mM KCl (isotonic) Krebs solution (KPSS; (Drummond & Cocks, 1996)) to obtain a maximum contraction for each artery ring (KPSS$_{max}$). The KPSS was then replaced with normal Krebs solution and the tissues allowed to return to their optimal passive force level over 0–60 min. Nifedipine (0.3 µM) and indomethacin (3 µM) were added to inhibit spontaneous contractile activity (Stork & Cocks, 1994a) and prostanoid release, respectively.

(A) Responses to PAR Activators

Aortic ring segments were contracted to approximately 50% KPSS$_{max}$ with titrated concentrations of the thromboxane A$_2$ mimetic, U46619 (1 to 10 nM). Once the U46619-induced contraction had reached a stable level, cumulative concentration response curves to thrombin and trypsin (0.0001 to 1 U/ml, or the human PAR1 activating peptide (SFLLRN—NH$_2$) (SEQ ID NO:1), the human PAR2 activating peptide (SLIGKV—NH$_2$) (SEQ ID NO:3) or the mouse PAR2 activating peptide (SLIGRL—NH$_2$) (SEQ ID NO:2) (0.01 to 100 µM) were generated in the presence of bovine serum albumin (BSA; 0.005%). At the completion of each curve, maximum endothelium-dependent and -independent relaxation for each ring segment was determined with the addition of substance P(3 nM) and isoprenaline (1 µM), respectively.

(B) Effect of Nitric Oxide Inhibitors

To examine the contribution of nitric oxide (NO) to PAR-mediated relaxation, aortic ring segments were either left untreated or were treated with the endothelial NO synthase inhibitor, L—NOARG; (100 µM), the NO scavenger, HbO (20 µM), or a combination of these agents, before the U46619-induced contraction.

(C) Desensitization Experiments

Tissues were either left untreated or were treated with cumulative additions of one of thrombin (0.1 U/ml) or trypsin (0.1 U/ml) every 30 min for 2 h in the presence of BSA (0.005% w/v). Tissues were then washed thoroughly with Krebs solution and contracted to approximately 50% KPSS$_{max}$ with U46619. Tissues were then exposed to the enzyme (0.1 U/ml) with which they had previously been treated until no further relaxation was observed. Importantly, the tissues were washed with Krebs solution, containing an appropriate concentration of U46619 to maintain the precontraction, between treatments with each activating enzyme. This ensured that receptor desensitisation was not masked by occupation of the receptor by the tethered ligand sequence. Once desensitisation was achieved, cross-desensitisation was investigated by addition of the enzyme (0.1 U/ml) not used in the desensitisation process. Following this, cumulative concentrationresponse curves to the mouse PAR1 activating peptide, SLIGRL—NH$_2$ (SEQ ID NO:2), were generated. Again, substance P(3 nM) and isoprenaline (1 µM) were then added to determine maximal endothelium-dependent and -independent relaxations, respectively.

(D) PAR-Mediated Responses

Figure 19B:
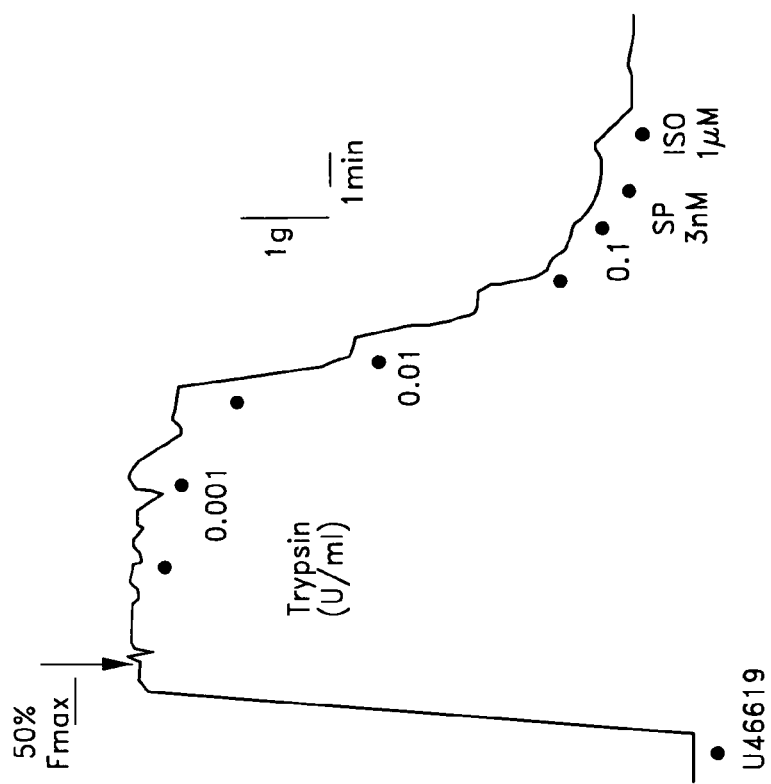
FIGS. 19A–19B show chart recordings illustrating relaxation to thrombin (a) and trypsin (b) in isolated human coronary arteries.
Figure 19A:
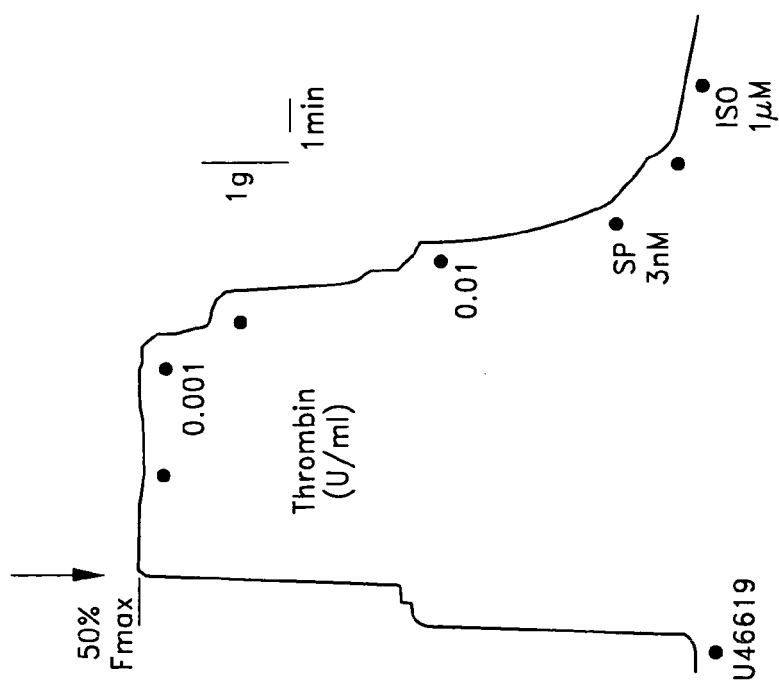
Figures 19C, 19D:
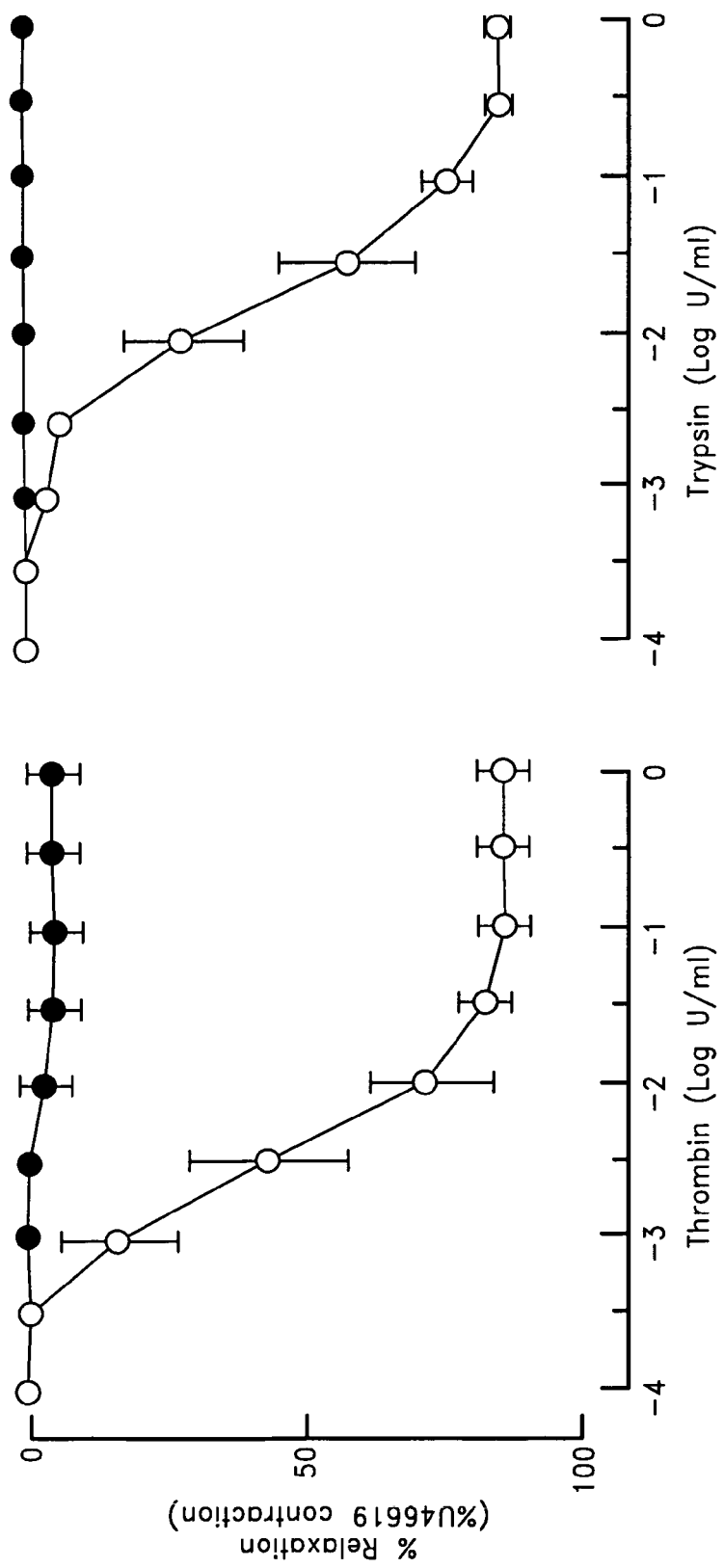
FIGS. 19C–19D illustrate cumulative concentration-response curves (c, d) that were generated in endothelium-intact (○) and -denuded (•) artery ring segments contracted to approximately 50% of their maximum contraction ($F_{max}$) in response to 125 mM KCl ($KPSS_{max}$) with U46619 as depicted in (a) and (b). The degree of relaxation is expressed as the percentage reversal of the U46619 contraction and is mean±SEM from five separate experiments (patients).

Thrombin (0.001 to 0.1 U/ml) and trypsin (0.01 to 1 U/ml) each caused rapid, enzyme activity-dependent relaxations of U46619-contracted human coronary artery rings, which were abolished upon removal of the endothelium, as shown in FIG. 19. Sensitivity pEC$_{50}$, log U/ml) and maximum (R$_{max}$ % contraction reversal) values for thrombin were 2.5+ 0.2 and 88.9±4.9%, respectively (n=5, from five patients). Relaxations to trypsin had a similar maximum (88.1±2.9%) to that for thrombin, but a significantly decreased (P<0.05) sensitivity pEC$_{50}$ 1.7±0.1) (n=5, from five patients).

Figures 20A, 20B:
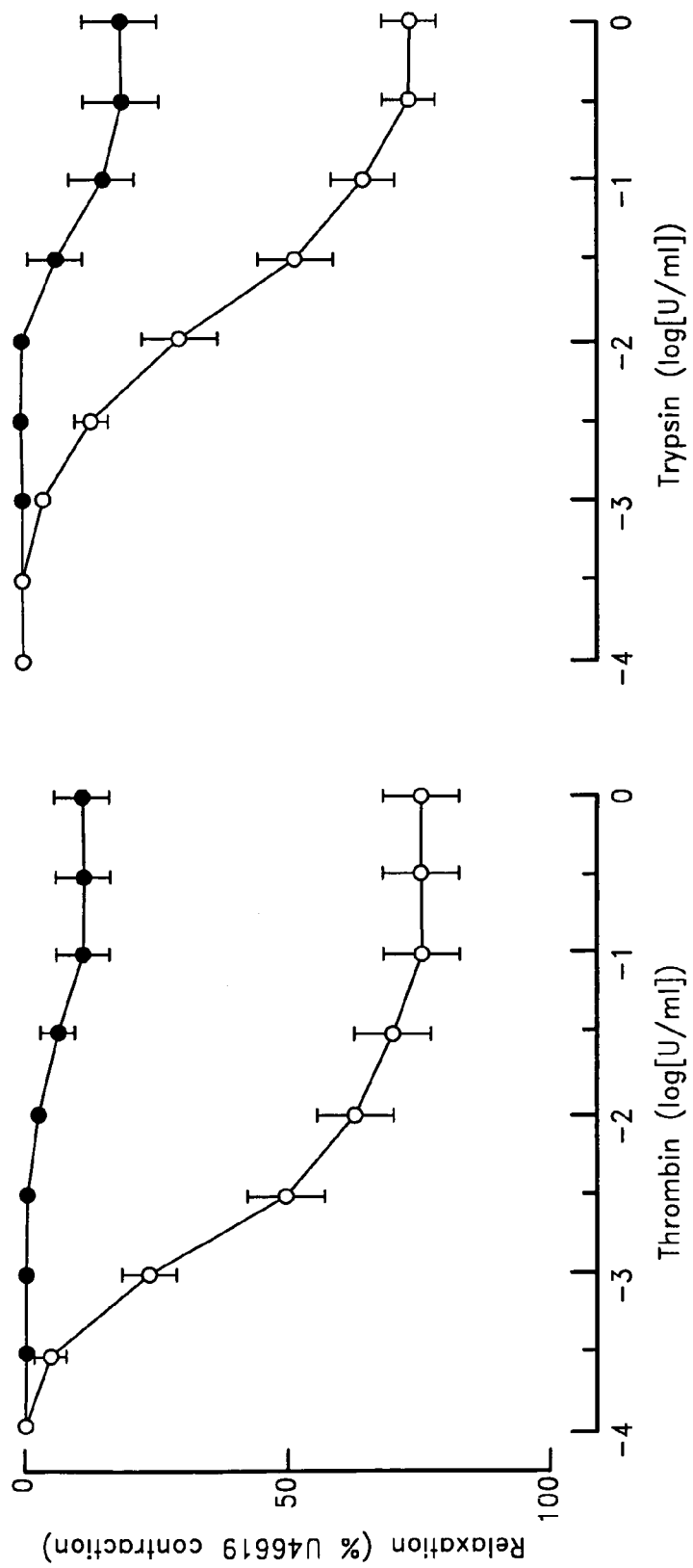
FIGS. 20A–20C shows the effects of inhibitors of nitric oxide on responses to thrombin (A), trypsin (B) and bradykinin (C) in human isolated coronary artery ring segments contracted to approximately 50% of their maximum contraction in response to 125 mM KCl with U46619. Responses to each enzyme were examined in control tissues (○) and tissues treated with a combination of $N^G$-nitro-L-arginine (100 μM) and oxyhaemoglobin (20 μM) (•). (Data are mean±SEM from 5–7 separate experiments (patients).
Figure 20C:
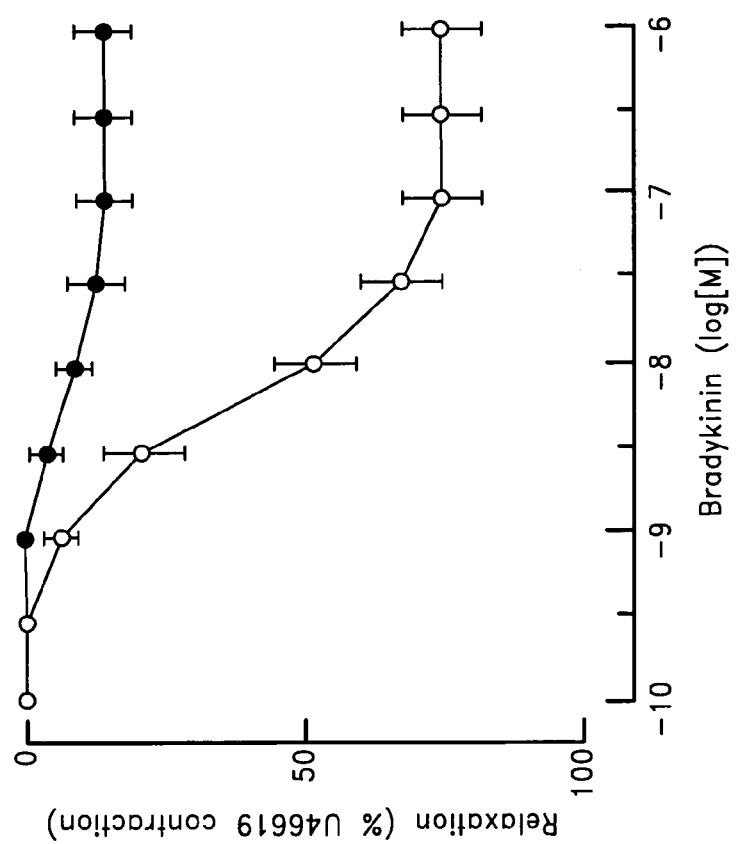

The endothelial NO synthase inhibitor, L—NOARG(100 uM), in combination with the NO scavenger, HbO (20 µM) significantly decreased both the sensitivity and maximum relaxation (P<0.05) of thrombin pEC$_{50}$ 1.0±0.4, R$_{max}$ 14.2±7.1%; n=5, from five patients) and trypsin (pEC$_{50}$ 1.3±0.2, R$_{max}$ 17.2±10.7%; n=5, from five patients), as shown in FIGS. 20A and 20B, respectively. For both enzymes, the effect of L—NOARG in combination with HbO was not significantly different from that of either HbO or L—NOARG alone. The effect of these NO inhibitors on PAR-mediated responses was also not significantly different to their effect on bradykinin (n=7, from seven patients) as shown in FIG. 20C. Thus, as with other endothelium dependent dilators of human coronary arteries, PAR-mediated relaxations appear to be mediated predominantly by endothelial cell-derived NO.

Figure 21:
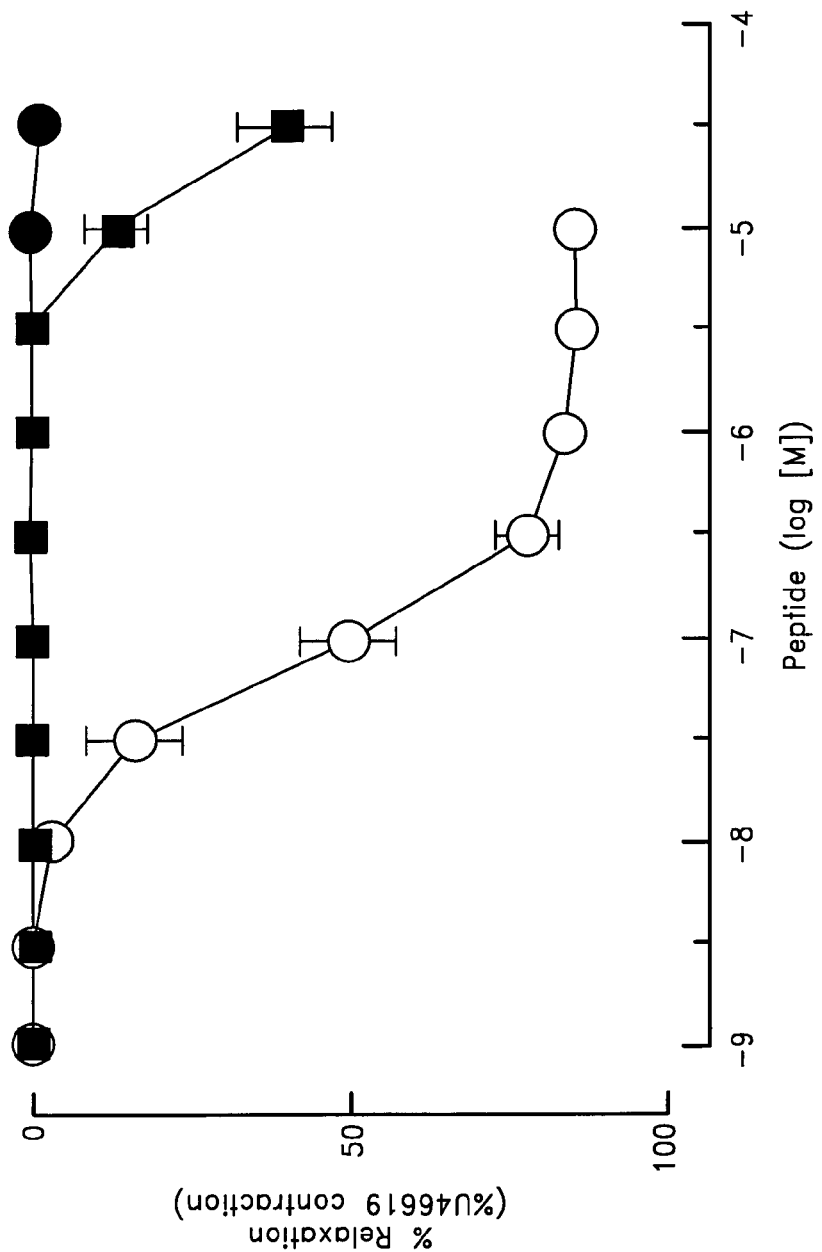
FIG. 21 shows the responses to PAR1 and PAR2 activating peptides in human isolated coronary artery ring segments contracted to approximately 50% of their maximum contraction in response to 125 mM ($KPSS_{max}$) with U46619. Cumulative concentration-response curves were generated to the human PAR1 activating peptide, SFLLRN—NH$_2$ (SEQ ID NO:1), in endothelium-intact (○, n=10 from 5 patients) and denuded (•, n=5 from 5 patients) preparations and to the human PAR2 activating peptide, SLIGKV—NH$_2$ (SEQ ID NO:3), in endothelium-intact tissues (■, n=5 from 2 patients). Data are expressed as mean±SEM.

The PAR1 activating peptide, SFLRN—NH$_2$ (SEQ ID NO:1), also caused potent relaxation of precontracted human coronary artery segments, with pEC$_{50}$ (–log M) and R$_{max}$ values of 6.9±0.1 and 95.2±1.3% (n=10, from five patients), respectively. This relaxation was abolished by endothelium denudation, as shown in FIG. 21. In contrast, responses to the human PAR2 activating peptide (SLIGKV—NH$_2$) (SEQ ID NO:3) were significantly less (R$_{max}$ 39.9±11.0%; n=5, from two patients). Interestingly, the mouse PAR2 activating peptide, SLIGRL—NH$_2$ (SEQ ID NO:2), which has a similar sequence to the human PAR2 activating peptide and has been shown to be equally active on PAR2 in other preparations (Blackhart et al, 1996), caused no relaxation.

(E) Desensitization of PARs

Figure 22A:
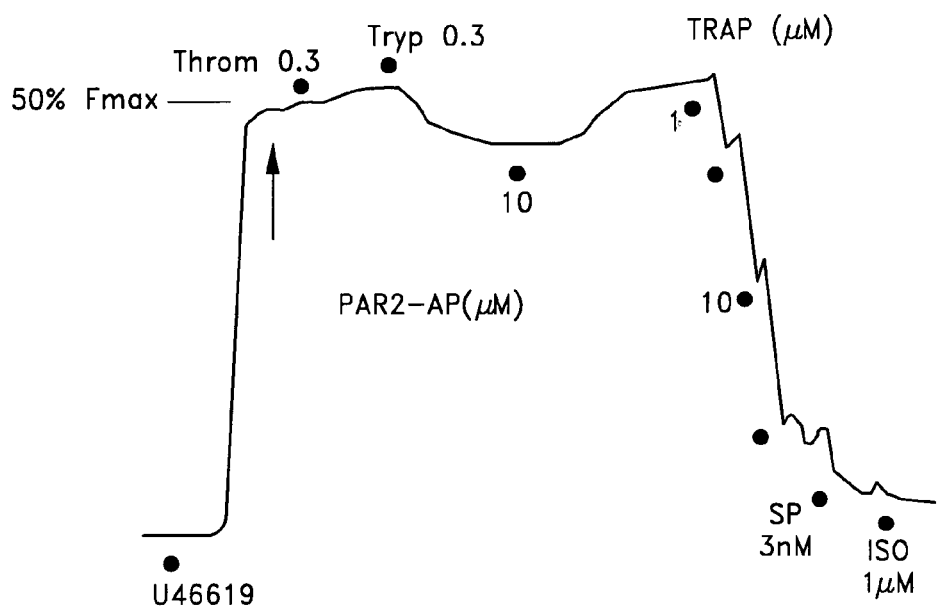
FIGS. 22A–22B show digitized traces of original chart recordings showing the effect of desensitization to thrombin (a) and trypsin (b) on relaxation to the thrombin receptor peptide ligand, SFLLRN—NH$_2$ (SEQ ID NO:1) (TRAP), in separate rings of human coronary artery contracted to—50% $F_{max}$ with 3 nM (a) and 4 nM (b) final concentrations of U46619. SP=substance P; ISO=isoprenaline; Throm=thrombin; Tryp=trypsin (units of both enzymes given as U/ml). The time calibration bar represents 20 min prior to the arrow. Tissues were incubated for at least 2h with maximum concentrations of (a) thrombin and (b) trypsin, and then washed prior to contraction with U46619.
Figure 22B:
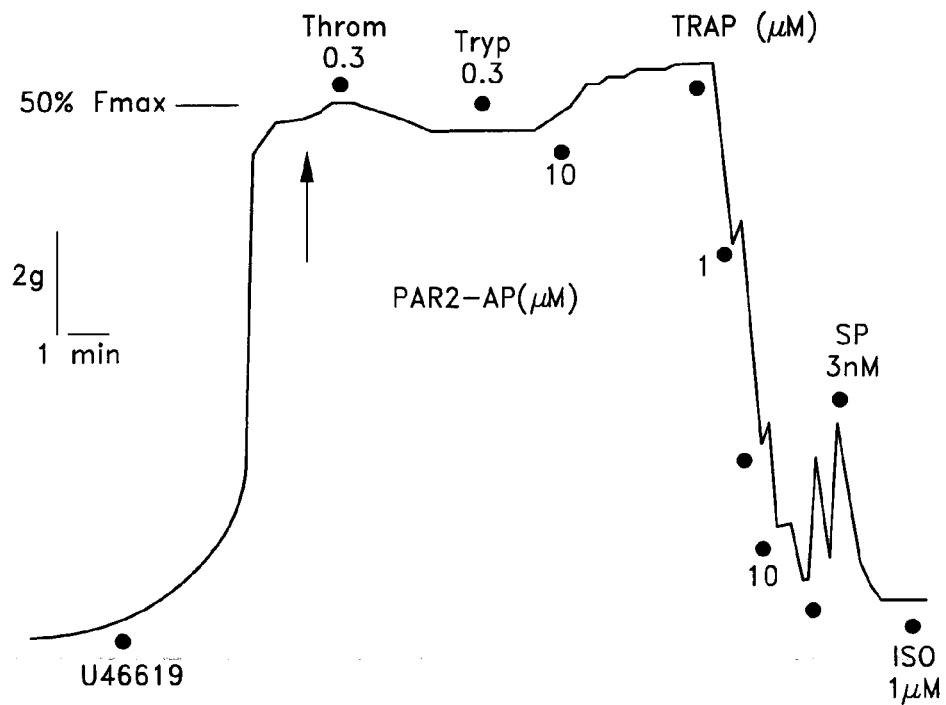
Figure 23:
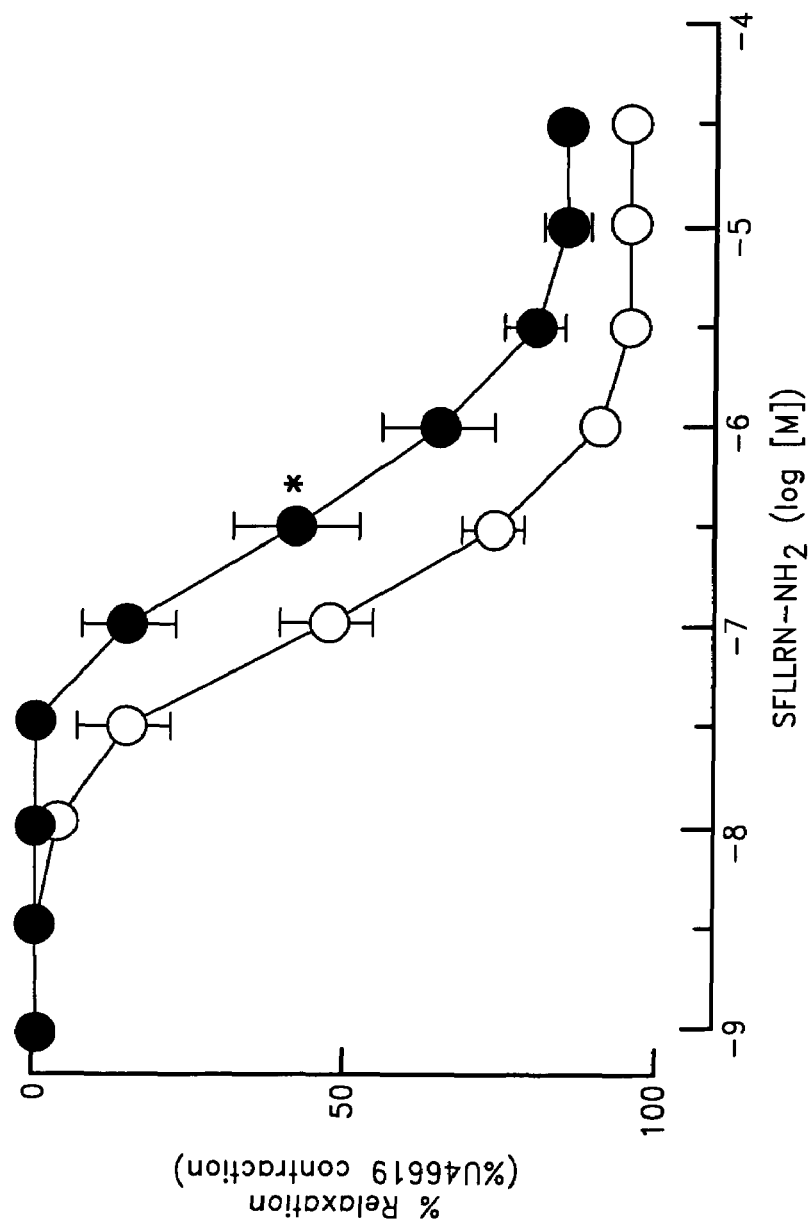
FIG. 23 shows the effect of thrombin desensitization on responses to the PAR1 activating peptide in human isolated coronary artery. Ring segments contracted to approximately 50% of their maximum contraction in response to 125 mM ($KPSS_{max}$) with U46619 were either untreated (○) or desensitized to both thrombin and trypsin (•) before cumulative concentration-response curves to the human PAR1 activating peptide, SFLLRN—NH$_2$ (SEQ ID NO:1), were generated. Data are expressed as mean±SEM (n=8, from 4 patients).

Desensitisation of tissues with either thrombin or trypsin caused loss of responsiveness to maximum relaxation-inducing concentrations of both enzymes, as shown in FIGS. 22a and 22b, indicating that the receptors) involved are activated by either of these enzymes. Interestingly, under these desensitizing conditions, the maximum response to SFLLRN—NH$_2$ (SEQ ID NO:1) was unaffected ($R_{max}$92.0±5.0), although there was a small, but significant (P<0.05) decrease in sensitivity (pEC$_{50}$ 7.0±0.1 vs 6.4±0.2; n=8, from 4 patients), as illustrated in FIG. 23.

This study is the first to show functional evidence of the presence of PAR-like receptors in isolated human coronary arteries. While the presence of mRNA encoding the first thrombin receptor, PAR1, has previously been reported in endothelial cells of human abdominal aorta (Nelken et al, 1992), others have demonstrated that the presence of protease-activated receptor mRNA does not necessarily correlate with tissue responsiveness (Saifeddine, 1996). Previous evidence for functional PAR in human endothelial cell s has been limited to the measurement of calcium fluxes in umbilical vein endothelial cells (Ngaiza, 1991; Kruse, 1995). However, it is important to examine the functional responses mediated by these receptors, and the studies described herein provide evidence that activators of PAR cause powerful, endothelium-dependent relaxation of human coronary arteries in vitro.

As has been demonstrated in the vasculature of the rat (Saifeddine et al, 1996) and pig (Hwa et al, 1996), the present studies show that U46619-contracted human coronary artery ring preparations were induced to relax by both thrombin and trypsin. However, only the peptide fragment corresponding to the human PAR1 tethered ligand sequence (SFLLRN—NH$_2$) (SEQ ID NO:1) was fully active in this preparation, while the PAR2 tethered ligand sequence (SLIGKV—NH$_2$) (SEQ ID NO:3) induced only a partial reversal of the U46619-induced contraction at comparably high concentrations.

Responses to both thrombin and trypsin were entirely dependent on the presence of an intact endothelium, and were virtually abolished by a combination of L—NOARG-mediated inhibition of endothelial NO production and scavenging of residual NO by HbO, indicating that PAR induced relaxations were mediated by endothelium-derived NO. The degree of inhibition was similar to that observed with bradykinin in this study, and is consistent with other reports that endothelium-dependent relaxation of human coronary vessels is mediated predominantly by NO for agents including bradykinin (Kemp & Cocks, 1997) and substance P (Chester et al, 1990). Others have also shown that PAR-mediated vasodilatation in rat (Muramatsu et al, 1992), pig (Tesfamarium et al, 1993) and dog (Tesfamarium, 1994) vessels is due to endothelial cell-derived NO. In contrast to previous reports which showed that thrombin contracted endothelium denuded preparations of coronary artery from dog (White, 1994; Tesfamarium, 1994) and pig (Glusa & Markwardt, 1988), neither thrombin nor trypsin induced contraction of endothelium-denuded human artery preparations in the present study. The lack of contraction to thrombin may be explained by the observation that mRNA for PAR1 was present only in endothelial cells in normal, nonatherosclerotic arteries (Nelken et al, 1992). Whether thrombin or the PAR1 activating peptide can cause contraction of endothelium-free vessels obtained from patients suffering from atheroma is of interest, since Nelken et al, (1992) also located PAR1 mRNA in smooth muscle cells in affected vessels. The observations suggest that both enzymes mediate relaxation by PAR 1 activation. However, although trypsin can cleave and activate PAR1, as shown in Vu et al (1991) the concentrations required ($\geq$25 U/ml or 50 nM) are far in excess of those observed in the present studies on human coronary arteries to cause endothelium-dependent relaxation (0.01–1 U/ml or 0.02–2 nM). The low potency of the human PAR2 tethered ligand sequence, SLIGKV—NH$_2$ (SEQ ID NO:3), and the lack of activity of the equivalent murine sequence, SLIGRL—NH$_2$ (SEQ ID NO:2), could initially be taken as evidence for the sole presence of PAR1 in human coronary arteries, with the specificity of this peptide being lost at high concentrations leading to "cross over" activation of PAR1. The human PAR2 tethered ligand sequence, SLIGKVD—NH$_2$ (SEQ ID NO:7), however, does not activate PAR1 at concentrations up to 1 mM in human platelets (Blackhart et al, 1996)—far in excess of those used in this study. Furthermore, structure-activity studies have shown that PAR1 activating peptides lacking an aromatic residue at position 2 (as is the case with SLIGKV—NH$_2$ (SEQ ID NO:3)) are incapable of activating PAR1 in both transfected cell lines (Nystedt et al, 1995) and human platelets (Scarborough et al, 1992; Vassallo et al, 1992). Therefore, PAR 1, and to a lesser extent PAR2, may exist in human coronary endothelial cells. Such a conclusion, however, is contrary to the present findings that heterologous desensitisation was induced by either thrombin or trypsin.

Such evidence suggests a single receptor type. In porcine coronary arteries, which are known to express both PAR1 and PAR2 (Hwa et al, 1996), heterologous desensitisation was observed with high concentrations of trypsin, but only homologous desensitisation occurred with thrombin (Hwa et al, 1996). Thus, while cross-desensitisation and the poor sensitivity of SLIGKV—NH$_2$ (SEQ ID NO:3) and SLIGRL—NH$_2$ (SEQ ID NO:2) point to their involvement of a single receptor population, the ability of relatively low concentrations of trypsin to mediate relaxalation similar to those observed with thrombin is inconsistent with the view that a 'typical' thrombin receptor is involved.

One explanation for these apparently disparate results is that human coronary artery endothelial cells posses an "atypical" thrombin receptor capable of activation by low concentrations of trypsin. For PAR1 and PAR3, low concentrations of thrombin cause rapid activation by means of a receptor-specific recognition site for this enzyme, termed the hirudin-like binding domain (Liu, 1991; Vu et al, 1991). This thrombin-binding region is located in the extracellular amino-terminal, immediately distal to the Arg$^{41}$-Ser$^{42}$ cleavage point required for receptor activation, and allows close alignment of the thrombin catalytic site with S this peptide bond (Vu et al, 1991). Therefore, these receptors are capable of targetting thrombin to their specific cleavage site, ensuring efficient receptor cleavage and rapid signal transduction prerequisites for efficient cellular responsiveness. Both the mouse and rat PAR2s are known to lack the hirudin-like thrombin binding domain (Saifeddine et al, 1996), and consequently are unresponsive to thrombin. However, these receptors most likely possess a similar amino-terminal recognition site for trypsin, since, like thrombin, trypsin causes high potency and rapid responses, most likely due to targeting of the enzyme to the PAR2 cleavage site.

The "atypical" thrombin receptor in the human coronary artery endothelial cell appears to be sensitively activated by both thrombin and trypsin via either a common or dual enzyme binding site(s). Further support for the existence of such a receptor is provided by the observation that SLIGKV—NH$_2$ (SEQ ID NO:3) is capable of inducing vasodilatation despite the lack of the critical aromatic residue at position 2. Therefore, without wishing to be bound by any proposed theory, the inventors believe that the receptor responsible for endothelium-dependent relaxation of human coronary artery is a PAR1-like receptor, which has a modified amino-terminal exodomain comprising a trypsin binding domain and a modified tethered ligand binding region containing different pharmacophore specificities.

This study also shows that complete desensitization of responses to both thrombin and trypsin had only a small inhibitory effect on the responses of the arteries to SFLLRN—NH$_2$ (SEQ ID NO:1), which is contrary to earlier reports using pig coronary artery (Tesfamarian, 1994; Hwa, 1996) and rat aorta (Hollelberg et al., 1996). However, differences in desensitization procedures between these previous studies and the present one might provide clues as to how PAR responsiveness is regulated following enzymic activation. In the present study, high concentrations of both thrombin and trypsin were used for 2 to 3 hours, followed by approximately 30 minutes recovery while enzyme washout and tissue contraction occurred. This resulted in complete loss of responsiveness to both thrombin and trypsin while retaining responsiveness to SFLLRN—NH$_2$ (SEQ ID NO:1). With a similar protocol in the pig coronary artery, homologous desensitization with thrombin and heterologous desensitization with trypsin were observed. However, in each case, responsiveness to SFLLRN—NH$_2$ (SEQ ID NO:1) and SLIGKV—NH$_2$ (SEQ ID NO:3) was maintained—In the study of Hwa et al (1996), a high enzyme concentration was used over a much shorter contact time (10 to 20 minutes), and importantly, the enzyme was not washed out. The results showed a loss of responses to SFLLRN—NH$_2$ (SEQ ID NO:1) after homologous desensitization with thrombin, and loss of both SFLLRN—NH$_2$ (SEQ ID NO:1) and SLIGKV—NH$_2$ (SEQ ID NO:3) responses following heterologous desensitization with trypsin.

The retention and loss of responses to the tethered ligand sequences following desensitization shown in the present studies and in that of Hwa et al (1996) may reflect the rates of internalization and recycling of PARs following enzymic activation. Both PAR1 and PAR2 are rapidly internalised upon enzymic activation, stimulating the mobilisation of a pool of intact, pre-formed receptors which are rapidly (<30 minutes) inserted into the cell membrane (Bohm et al, 1996; Hein et al, 1994; Hoxie et al, 1993). The loss of subsequent enzyme-induced responses observed by Hwa et al (1996) using a rapid desensitization technique could be explained by the inability of the cell to replenish cell surface receptors from its intracellular reserve over this short period. With the prolonged desensitization technique used in this study, any reserves of intracellular receptors would probably have been depleted. Despite this, responses to SFLLRN—NH$_2$ (SEQ ID NO:1) were only minimally affected.

Therefore, it is proposed that, once activated, human endothelial cell PAR are internalised into early endosomes, as previously reported for human erythroleukemia cells (Hoxie et al, 1993), and are then returned to the membrane without their amino-terminal exodomain. Despite the absence of this exodomain they are able to respond to exogenously-applied tethered ligand sequences. This also indicates the presence of an endogenous activator which may act independently of receptor cleavage.

EXAMPLE 10

PAR-Mediated Relaxation in Human Bronchioles

Small (500 μm) bronchioles were carefully dissected from discarded sections of human left lung which had been excised at surgery from two male lung cancer patients (49 and 63 years old, Royal Melbourne Hospital, Melbourne, Australia).

Figure 24:
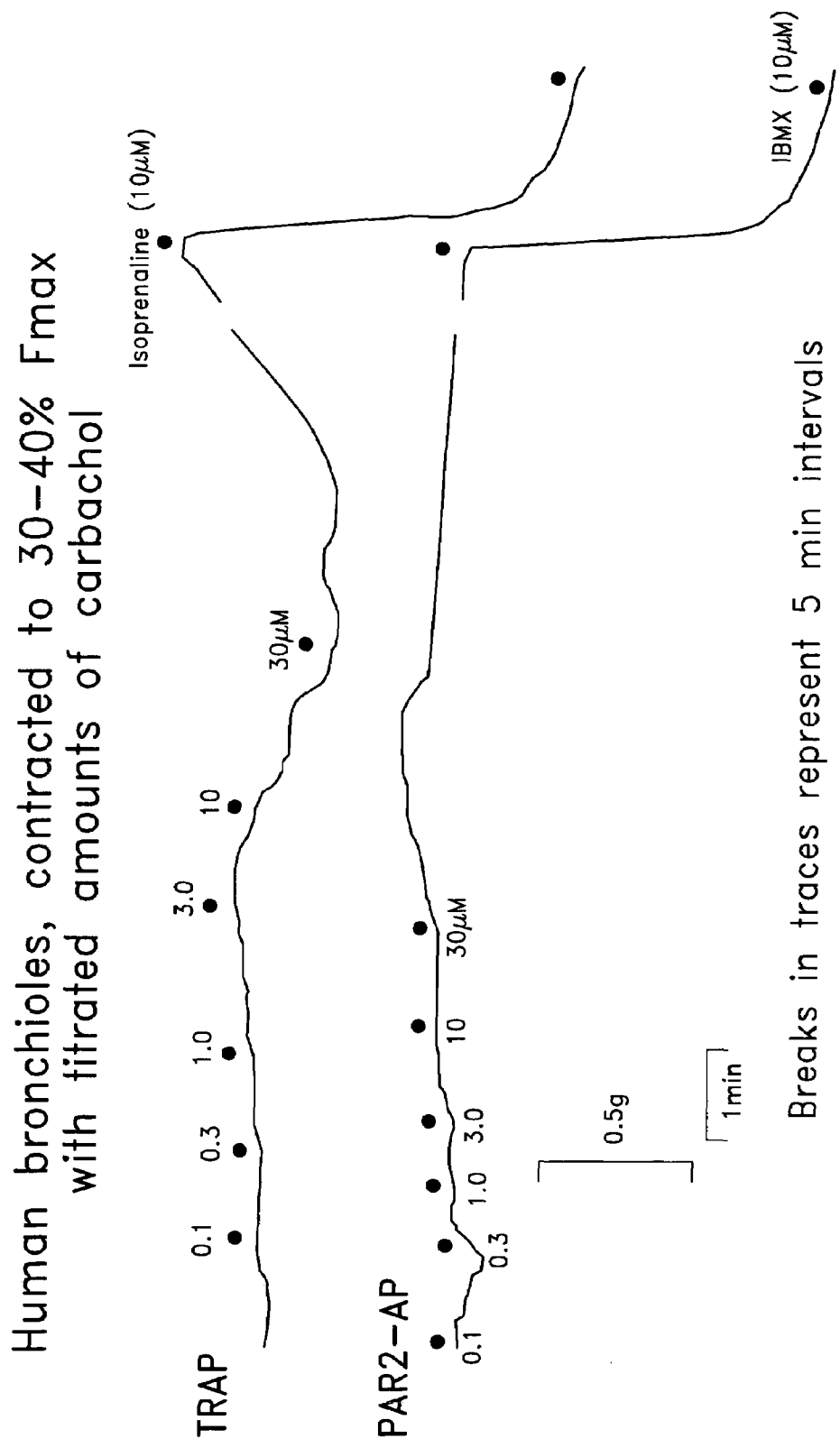
FIG. 24 shows relaxation to the PAR 1-activating peptide (A;TRAP) but not the PAR2 activating peptide (B;PAR2-AP) in two 2 mm long ring segments of isolated human bronchioles (approximately 500 μm internal diameter). Both segments were contracted to approximately 30% $F_{max}$ with carbachol, 0.005% w/v BSA was added and then TRAP and PAR2-AP were cumulatively added. Only TRAP caused concentration-dependent relaxations up to a maximum of approximately 30% that of isoprenaline plus IBMX. Breaks in the traces represent 10 min.
Figure 25:
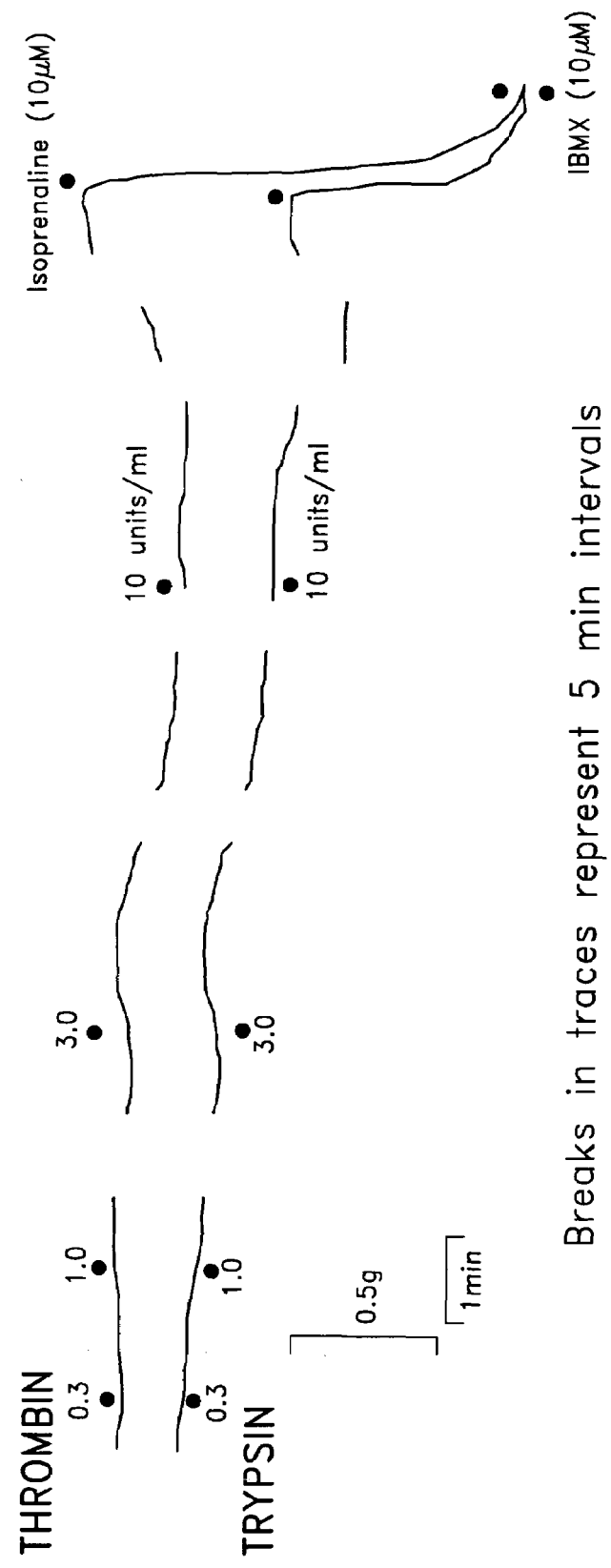
FIG. 25 shows relaxation to (A) thrombin and (B) trypsin in two separate 2 mm long ring segments of isolated human bronchioles (approximately 500 μm in internal diameter). The set-up procedure was as described in FIG. 24. Both enzymes caused slow, activity-dependent relaxation of between 30 and 60% maximum relaxation to isoprenaline plus IBMX. The traces were interrupted (5–20 minute breaks) to depict rates of onset of relaxation and maximum responses.

Dissection of these bronchioles required a fine-dissecting microscope and an assistant to continually flood the preparation with cold oxygenated Krebs solution to remove air bubbles and keep the tissue viable. Bronchioles approximately 2 mm in length were then mounted on 40 μM diameter stainless wires in a Krebs solution-filled myograph chamber, as described for the mouse bronchus preparation above. Unlike the mouse bronchi, the human bronchiole preparation developed active force spontaneously after the initial stretch to 0.5 g, then recovered partially as shown in FIGS. 24 and 25.

Like the mouse tissues, the human bronchioles were contracted to approximately 30–40% $F_{max}$ with titrated cumulative concentrations of carbachol. FIGS. 24 and 25 show that both thrombin and trypsin caused activity dependent relaxation that was reversed by indomethacin. In contrast, only the PAR1-activating peptide SFLLRN—NH$_2$ (SEQ ID NO:1) (TRAP) relaxed the bronchioles. The PAR2-activating peptide, SLIGRL—NH$_2$ (SEQ ID NO:2) (PAR2-AP) appeared to cause some contraction, but this was most likely baseline drift.

This finding shows that thrombin and trypsin caused relaxation, but that only TRAP, not PAR2-AP, mimicked this activity. This is remarkably similar to the pattern of activity observed for PAR-mediated endothelium-dependent relaxation in the human isolated coronary artery in Example 5.

EXAMPLE 11

Cellular Localization of PAR2 in the Airway Wall

Before testing the hypothesis that airways epithelial PAR2 are bronchoprotective, the inventors determined their cellular localisation within the airway wall. Using an antibody directed against the carboxyl terminal of mouse PAR2 and confocal fluorescence miscroscopy. The inventors found specific PAR2 immunoreactivity localised to epithelial cells, often focally within the cytoplasm, as well as to smooth muscle cells and fibroblasts in the submucosa of the mouse bronchus. These results are shown in FIG. 26.

Fresh frozen, paraformaldehyde-fixed sections (14 μM) of mouse bronchus were incubated with a rabbit antiserum directed against the carboxy-terminal of mouse PAR2 (CS-VKTSY) (SEQ ID NO:5) at a dilution of 1:500 for 48h, washed with PBS and then incubated with a biotinylated donkey anti-rabbit antiserum (Amersham) for 2 h, washed again with PBS, and then labelled with FITC-conjugated streptavidin (Amersham), all at room temperature. After a final wash in PBS, the sections were mounted in buffered glycerol and viewed under a Biorad MRC1000 confocal scanning laser system installed on an Olympus IMT2 microscope with a krypton/argon laser. Visualisation of FITC was achieved using a 488 nm excitation filter and a 522/535 nm emission filter. Images of 768×612 pixels were then processed using Adobe Photoshop software.

The inventors demonstration that PAR2 immunoreactivity was often localised in discrete cytoplasmic regions of airway epithelial cells supports the concept of rapid turnover from intracellular stores; which was demonstrated in Example 6. Furthermore, the inventors were unable to demonstrate specific localisation of PAR2 mRNA in mouse bronchi using in situ hybridisation whilst readily detecting PAR2 mRNA in the same tissue via reverse-transcriptase-polymerise chain reaction (RT-PCR). This discrepancy supports the idea that there are intracellular stores of receptors which are filled by translation of stable mRNA segments of low transcript number. Therefore, the capacity of airways epithelial cells in situ to rapidly replenish functional PAR2 following their enzymatic activation provides additional evidence that the epithelial PARs are involved in protection of the bronchial wall during inflammation.

EXAMPLE 12

PAR2 in Airway Epithelium

Using an antibody directed against the carboxyl terminal of mouse PAR2 and confocal fluorescence microscopy, the inventors found specific PAR2 immunoreactivity localised to epithelial cells, often focally within the cytoplasm, as well as to smooth muscle cells and fibroblasts in the submucosa of the mouse bronchus (FIG. 26). In functional studies, the mouse PAR2 tethered ligand sequence, SLIGRL—$NH_2$ (SEQ ID NO:2); Nystedt et al, 1994) and trypsin each caused concentration-dependent, rapid onset and near-maximum relaxation of mouse bronchial rings contracted with the stable muscarinic agonist carbachol. These relaxations were abolished by either removal of the epithelium or inhibition of cyclooxygenase (FIGS. 1 & 26). For SLIGRL—$NH_2$ (SEQ ID NO:2) the sensitivity ($pEC_{50}$–log M) was 5.6±0.1 and the maximum relaxation ($R_{max}$) was 94±3%.

Similar concentration-dependent relaxations were obtained from the PAR1 tethered ligand sequence SFLLRN—$NH_2$ (SEQ ID NO:1); Dery et al, 1988; $\lambda pEC_{50}$, 5.6±0.1; $R_{max}$, 76±11%) and thrombin. In contrast to PAR2 activation, removal of the epithelium or inhibition of cyclooxygenase unmasked smooth muscle contractions to PAR1 activation with SFLLRN—$NH_2$ (SEQ ID NO:1) (FIGS. 1 & 26). Unlike SLIGRL—$NH_2$ (SEQ ID NO:2) (Blackhart et al, 1996) which is a specific activator of PAR2, SFLLRN—$NH_2$ (SEQ ID NO:1) can activate both PAR1 and PAR2. However, the inability of SLIGRL—$NH_2$ (SEQ ID NO:2) to contract epithelium-denuded or cyclooxygenase blocked preparations of the mouse bronchi indicates that SFLLRN—$NH_2$ (SEQ ID NO:1) causes smooth muscle contraction via activation of PAR1. It is clear that the relaxations observed in response to SLIGRL—$NH_2$ (SEQ ID NO:2) or low concentrations of trypsin were due to activation of epithelial PAR2 or an unidentified receptor with similar sensitivity to SLIGRL—$NH_2$ (SEQ ID NO:2) and trypsin. This is confirmed by the one observation that the responses to SLIGRL—$NH_2$ (SEQ ID NO:2) were abolished by prior desensitisation to trypsin but were unaffected by thrombin desensitisation whilst those to SFLLRN—$NH_2$ (SEQ ID NO:1) were abolished following desensitisation to both thrombin and trypsin.

Relaxations to SLIGRL—$NH_2$ (SEQ ID NO:2) and SFLLRN—$NH_2$ (SEQ ID NO:1) in the mouse bronchi were not due to nitric oxide (NO) since they were unaffected by the NO synthase inhibitor, $N^G$-nitro-L-arginine (100 μM) and the NO scavenger, oxyhaemoglobin (20 μM; FIG. 26). Therefore, a prostanoid rather than NO mediated the relaxations of both PARs. $PGE_2$ is a likely candidate, since it is the most prevalent prostanoid released from the airway epithelium and the inventors found it to sensitively and powerfully relax mouse bronchi ($pEC_{50}$, 8.2±0.1; $R_{max}$, 100%, FIG. 1).

Smaller, intrapulmonary airways are likely to contribute more than larger airways to resistance to flow in the lungs. Therefore, the inventors investigated the effects of PAR-activating peptides in first generation branches of the mouse main bronchi. The inventors observed similar indomethacin-sensitive relaxations to the PAR ligands in these preparations although the sensitivity and maximum relaxation to both SFLLRN—$NH_2$ (SEQ ID NO:1) ($pEC_{50}$, 5.5±0.02; $R_{max}$, 58±10%) and SLIGRL—$NH_2$ (SEQ ID NO:2) ($pEC_{50}$, 5.1±0.05; $R_{max}$, 58±4%) were significantly less (P<0.05) than those in the main bronchi (FIG. 26).

Since enzymatic activation of PARs is irreversible, rapid resensitisation mechanisms are critical for the maintenance of tissue responsiveness to PARactivating proteases. Turnover of cloned PAR1 expressed in selected cell lines has been shown to be rapid and dependent on both de novo synthesis of new protein as well as trafficking of performed receptors from intracellular pools (Dery et al, 1998; Bohm et al, 1996). The data generated herein show that in the mouse bronchi, PAR2-mediated relaxations returned after 45 min following desensitisation to trypsin (FIG. 11 B). This recovery was abolished by the protein trafficking inhibitor, brefeldin A (10 μM) or the translation inhibitor, cycloheximide (70 μM; FIG. 11C). These findings, together with the demonstration here that PAR2 immunoreactivity was often localised in discrete cytoplasmic regions of airway epithelial cells (FIG. 26), support the concept of rapid PAR2 turnover from intracellular stores in airway epithelium. Furthermore, the inventors were unable to demonstrate specific localisation of PAR2 mRNA in mouse bronchi using in situ hybridisation whilst readily detecting PAR2 mRNA in the same tissue via reverse transcription-polymerase chain reaction. The apparent discrepancy between these findings could be explained by the immunohistochemical demonstration of intracellular stores of PAR2 (FIG. 26) which are continually replenished by translation of stable message of low transcript number. Thus, the capacity of airway epithelial cells in situ to rapidly recover their sensitivity to PAR2 agonists following receptor desensitisation supports a role for epithelial PAR2 in bronchoprotection.

In addition to the mouse, the inventors also observed PAR-mediated bronchorelaxation in the airways of other species. Thus, SLIGRL—$NH_2$ (SEQ ID NO:2) caused epithelium-dependent and indomethacin-sensitive relaxations in rat isolated bronchi ($pEC_{50}$, 5.5±0.1; $R_{max}$, 56±5%) and bronchioles ($pEC_{50}$, 5.1±0.1; $R_{max}$, 67±5%) and similar potency ($pEC_{50}$, 5.4±0.2), epithelium-dependent relaxation in the guinea-pig isolated bronchi but with a significantly (P<0.05) lower $R_{max}$ (31±5%) than those in both rat and mouse bronchi. Also, from experiments (n=4), the inventors observed PAR2-mediated relaxations in human intrapulmonary airways which, although weak by comparison with those in mice, were blocked by indomethacin.

Importantly, the inventors have demonstrated here that SLIGRL—$NH_2$ (SEQ ID NO:2) is a highly effective inhibitor of bronchoconstriction in vivo. Thus, a 30 sec exposure to an aerosol of a 0.1 mg/ml solution of SLIGRL—$NH_2$ (SEQ ID NO:2), but not the scrambled peptide sequence LSIGRL—$NH_2$ (SEQ ID NO:4) caused inhibition (50–70%) of 5-hydroxytryptamine (5-HT)-induced changes in airway resistance ($R_L$) and dynamic compliance ($C_{dyn}$) in anaesthetised rats. This effect of SLIGRL—$NH_2$ (SEQ ID NO:2) could be functionally antagonised by higher doses of 5-HT.

It is clear from the data presented herein that the PAR-mediated bronchorelaxation described herein is cyclooxygenase-dependent. $PGE_2$ is the likely prostanoid involved since it is the only cyclooxygenase product released by airway epithelial cells capable of inducing potent bronchorelaxation. Also, substance P, another substance which induces epithelium-dependent bronchorelaxation, has been shown to mediate this response in the rat bronchi via release of $PGE_2$ from the epithelium. $PGE_2$ exerts other bronchoprotective actions in humans at concentrations well below those required for bronchodilatation. These include inhibition of cholinergic neurotransmission, lung mast cell activation, eosinophil chemotaxis, IL-2 production by T lymphocytes and IL-4-induced IgE production by B lymphocytes. Furthermore, $PGE_2$ synthesised by human airway epithelium probably contributes to refractoriness to histamine challenge in humans and exercise-induced asthma. Also, inhalation of $PGE_2$ in allergic asthmatics not only prevents the early phase of the response to allergen challenge but the late phase as well. Therefore, although inhalation of $PGE_2$ causes acute cough in man, stimulation of endogenous $PGE_2$ release by PAR2 may place crucial roles in airway defence.

The studies presented herein assign functionality for PAR2 and PAR2 in the airways. Also, they show that PAR2 activation results in powerful bronchodilatation in vivo and epithelium-dependent bronchial relaxation in vitro with no evidence for direct contraction. Therefore, airway epithelial PAR2 is bronchoprotective. However, because PAR2 is also expressed in the subepithelium, particularly on smooth muscle cells, the inventors propose a dual compartment model for the role of PAR2 in the airways. In this model the barrier function of the epithelium separates epithelial cells (compartment 1) from the underlying tissues in compartment 2. Also, epithelial and subepithelial PAR2 are differentially regulated by specific tryptic enzymes released preferentially in each compartment—epithelial trypsin for compartment 1 and mast cell tryptase for compartment 2. The inventors propose that trypsin is the endogenous activator of epithelial PAR2 is supported by the demonstration here that trypsin(ogen) is colocalised with PAR2 in human airway epithelium. In addition, trypsin is regulated by $\alpha_1$-antitrypsin in the lungs whereas there are no known inhibitors of mast cell tryptase. Therefore, the model predicts that epithelial PAR2 normally override any proinflammatory effects of PAR2 activation in compartment 2 and that disruption of the epithelial barrier compromises the normal balance between the two compartments.

This study indicates that epithelial PAR2 causes powerful bronchorelaxation in vitro and that their activation in vivo suppresses bronchoconstriction. Therefore, activation of PAR2 initiates important paracrine protection in the airways by functionally antagonising elevated airway tone. If $PGE_2$ is the mediator of this effect, then airway epithelial PAR2 have the potential to initiate other paracrine protective responses as well as autocrine protective effects within the epithelium. As such, these receptors offer scope fro new therapies for diseases like asthma and bronchitis. This is supported by the demonstration that inhalation of $PGE_2$ in mild asthmatics markedly inhibited allergen-induced airway responses (constriction) and airway inflammation. The present invention provides a mechanism of activating the $PGE_2$-mediated bronchoprotection system.

EXAMPLE 13

PAR Mediated Relaxation in Mouse Bronchioles

In addition to the findings in mouse bronchi, shown in the earlier Examples, indomethacin-sensitive relaxations to both the PAR1- and PAR2-activating peptides were also observed in first branches of the main bronchi of the mouse, which the inventors have termed bronchioles. However, the sensitivity and maximum relaxation to SFLLRN—$NH_2$ (SEQ ID NO:1) ($pEC_{50}$ 5.5±0.02; $R_{max}$, 58±10%) and SLIGRL—$NH_2$ (SEQ ID NO:2) ($pEC_{50}$ 5.1±0.05; $R_{max}$ 58±4%) were significantly less (P<0.05) than those shown in FIG. 27 for the main bronchi. Similar responses to SLIGRL—$NH_2$ (SEQ ID NO:2) were observed in other species. Thus, SLIGRL—$NH_2$ (SEQ ID NO:2), caused indomethacin-sensitive relaxations in rat bronchi ($pEC_{50}$ 5.5±0.1; $R_{max}$ 56±5%) and bronchioles ($pEC_{50}$ 5.1±0.01; $R_{max}$ 67±5%) and similar potency ($pEC_{50}$ 5.4±0.2%) epithelium-dependent relaxation in the guinea-pig but with significantly (P<0.05) lower efficacy ($R_{max}$ 31±5%) than in both rat and mouse bronchi. Furthermore, in preliminary experiments, the inventors observed PAR2mediated relaxation in human bronchi (n=4), which in one case was blocked by indomethacin. The similar potencies for SLIGRL—$NH_2$ (SEQ ID NO:2) in mice, rats and guinea-pigs indicate expression of a similar receptor, whilst the different efficacies suggest either different receptor numbers or coupling between species. The rank order of efficacies for SLIGRL—$NH_2$ (SEQ ID NO:2), mouse>rat>guinea-pig, however, contrasts with the severity of symptoms in allergic models of asthma. For example, mice show resistance to immunological challenge including only a small degree of airway hyperreactivity (AR) compared with rats and guinea-pigs, the latter of which show characteristic high levels of A4[16] and may die when exposed to similar immunological challenges. One reason why mice appear relatively asymptomatic when used in immunological models of asthma may in part be due to a higher relative effectiveness of their PAR2-dependent bronchoprotective mechanism.

Figure 26A:
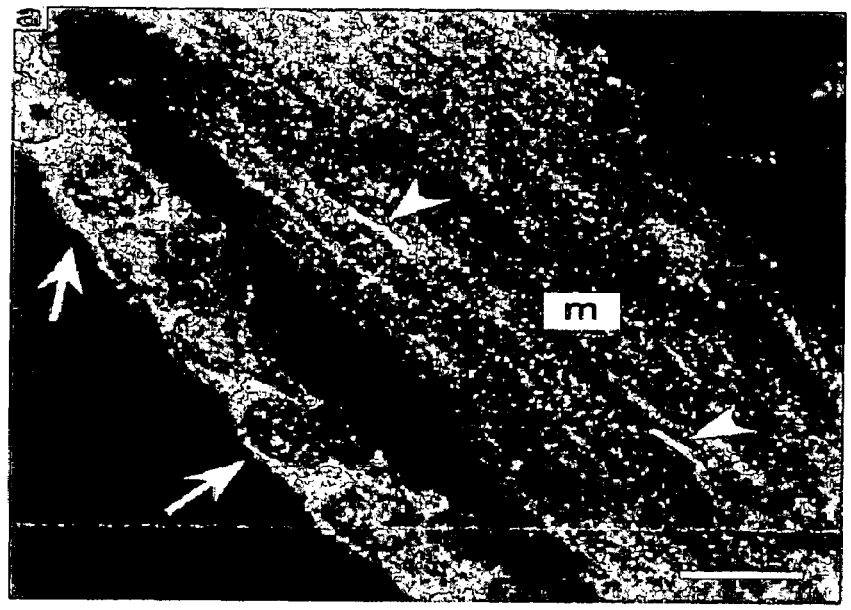
FIGS. 26A–26D show the immunohistochemical localization of PAR2 in mouse bronchi, and demonstrates that PAR2 and PAR1 mediates epithelium-dependent relaxation in isolated rings of this tissue.
  (a) Confocal photomicrograph showing PAR2 immunofluorescence to discrete epithelial cells (arrow) as well as smooth muscle cells (m) and fibroblasts (arrow head). In some epithelial cells, the fluorescence appeared concentrated within areas of the cytoplasm. Pre-absorption with they peptide sequence used to raise the mouse PAR2 antibody quenched the epithelial, smooth muscle and fibroblast fluorescence. The scale bar represents 10 μm.
  (b) An original, digitised chart recording of changes in isometric force in a single ring of mouse left bronchus with intact epithelium. The tissue was contracted to approximately 40% $F_{max}$ to acetylcholine (Ach; 30 μM) with cumulative, titrated concentrations of carbachol. Note the change of gain, and that the force recovered spontaneously over the 15 minute break in the trace after maximum relaxation to SLIGRL—NH$_2$(SEQ ID NO:2).
  (c) Removal of the epithelium with 0.1% v/v Triton X-100 abolished relaxation to SLIGRL—NH$_2$ (SEQ ID NO:2) and SFLLRN—NH$_2$ (SEQ ID NO:1) whereas the tissue could still sensitively relax to PGE$_2$.
  (d) Light photomicrographs of cross sections of mouse bronchi, showing that the 0.1% Triton X-100 perfusion technique removed the vast majority of columnar epithelial cells (arrows) with no microscopic evidence of damage to the underlying smooth muscle (m). Scale bar represents 30 μm.
Figure 26D:
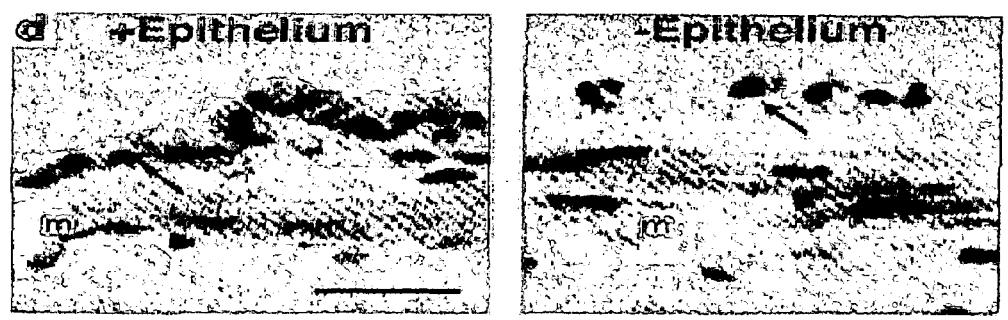
Figure 26B:
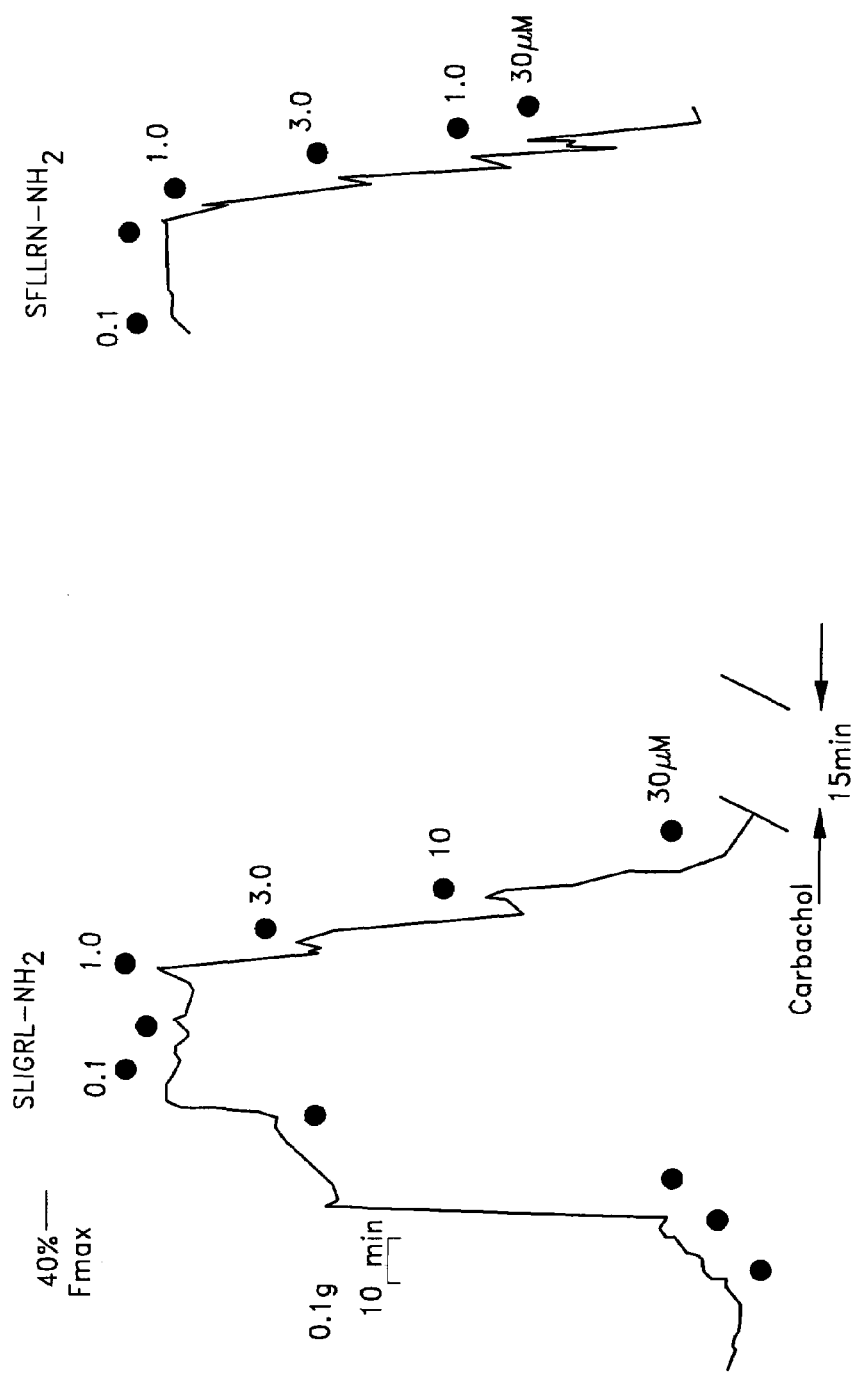
Figure 26C:
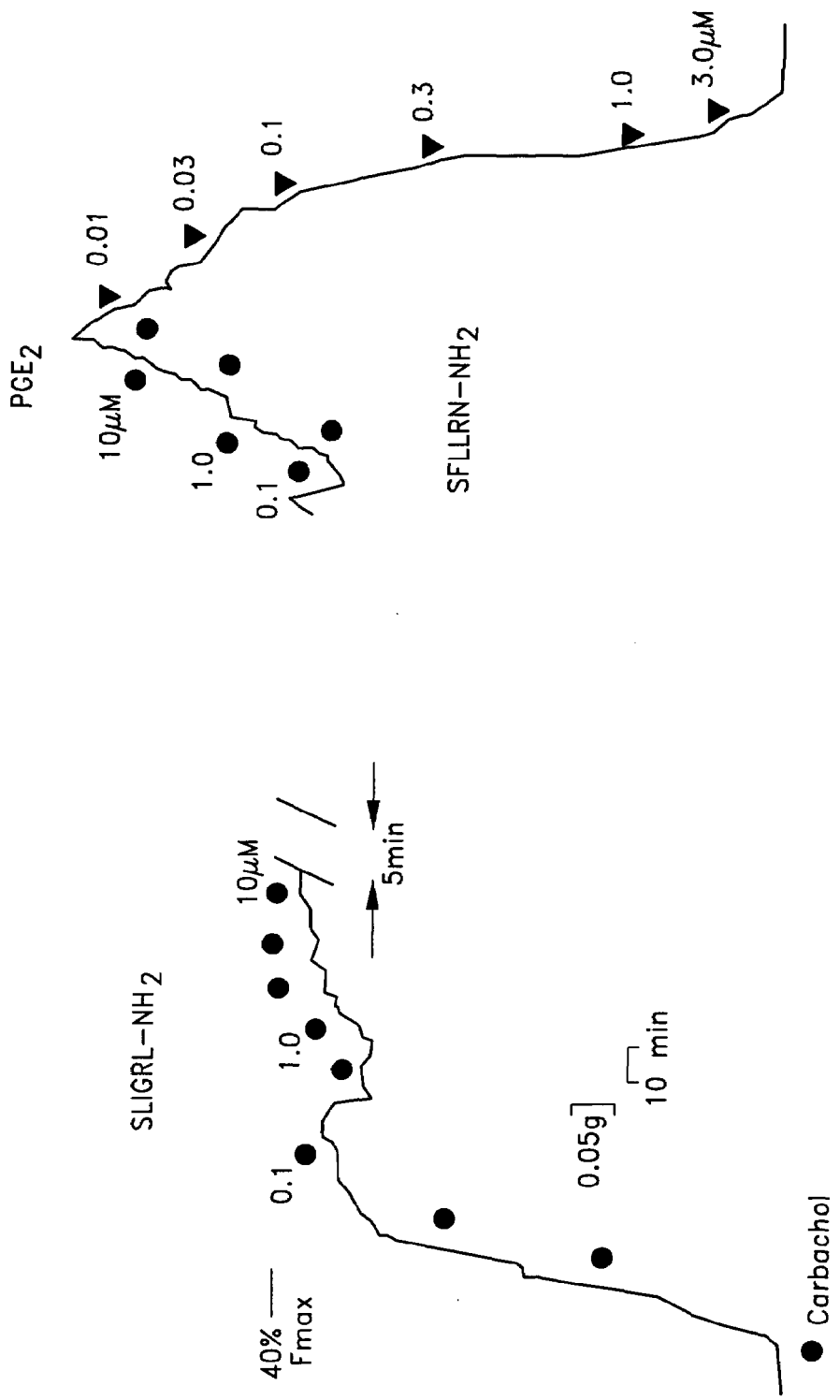
Figure 27A:
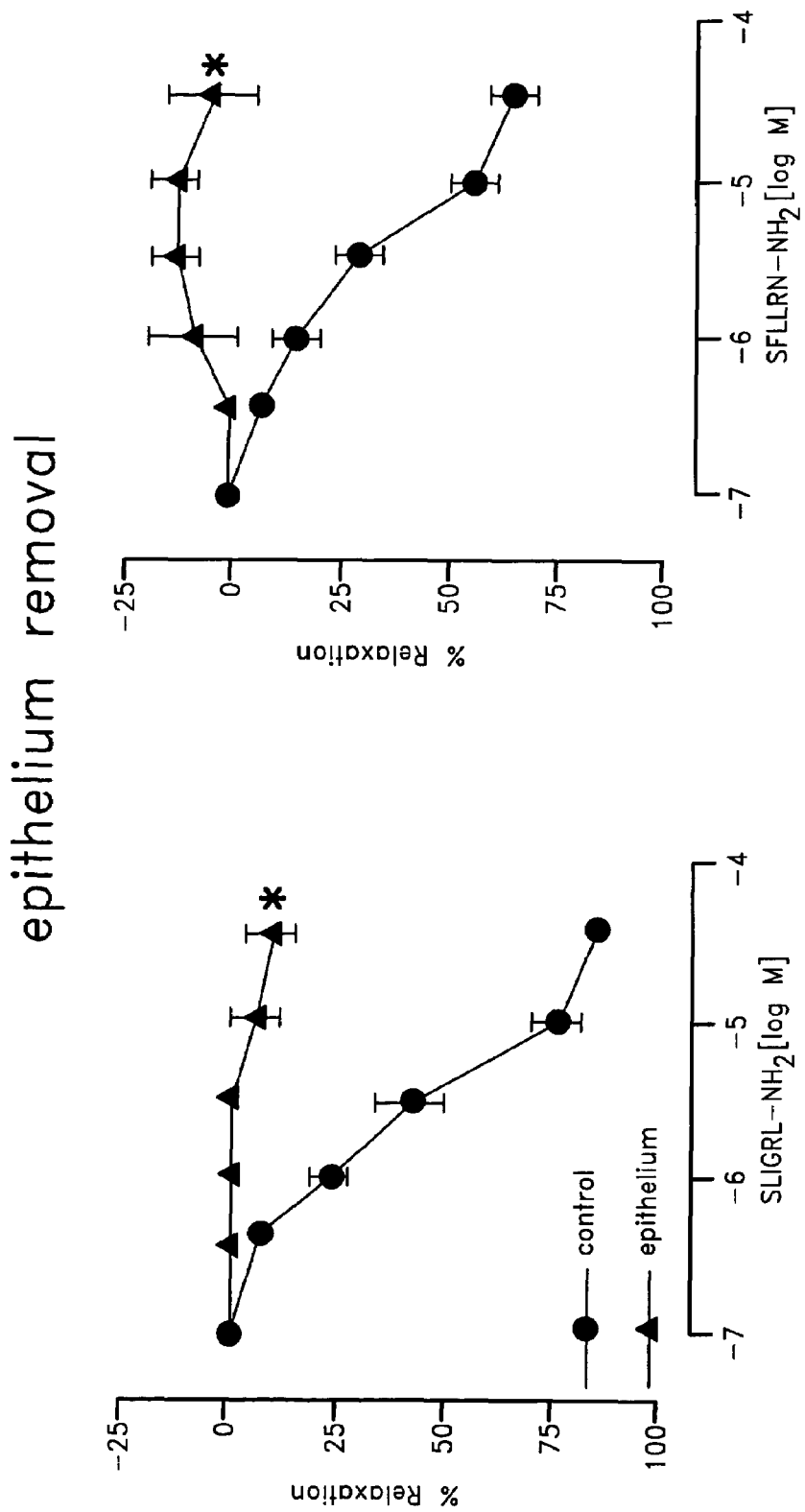
FIGS. 27A–27C shows the mechanisms of PAR-mediated bronchodilation.
  (a) epithelium-; and
  (b) cyclooxygenase-dependent relaxations of mouse isolated bronchi to the PAR2 and PAR1 synthetic peptide ligands SLIGRL—NH$_2$ (SEQ ID NO:2) and SFLLRN—NH$_2$ (SEQ ID NO:1), respectively.
  (c) relaxations to trypsin and thrombin in epithelium-intact preparations were similarly abolished by cyclooxygenase inhibition. Group data from similar experiments to that described in FIG. 26, except that tissues were treated with indomethacin (3 μM) and aspirin (100 μM) to block cyclooxygenase activity. All relaxations and contractions are expressed as percentages of the initial force to carbachol (40% $F_{max}$) regardless of treatment. Values on the graphs are mean±s.e.mean from 5–9 experiments, except aspirin (n=3). *P<0.01. Note that the NO inhibitors had no effect on the relaxations to PAR1- and PAR2-activating peptides.
Figure 27B:
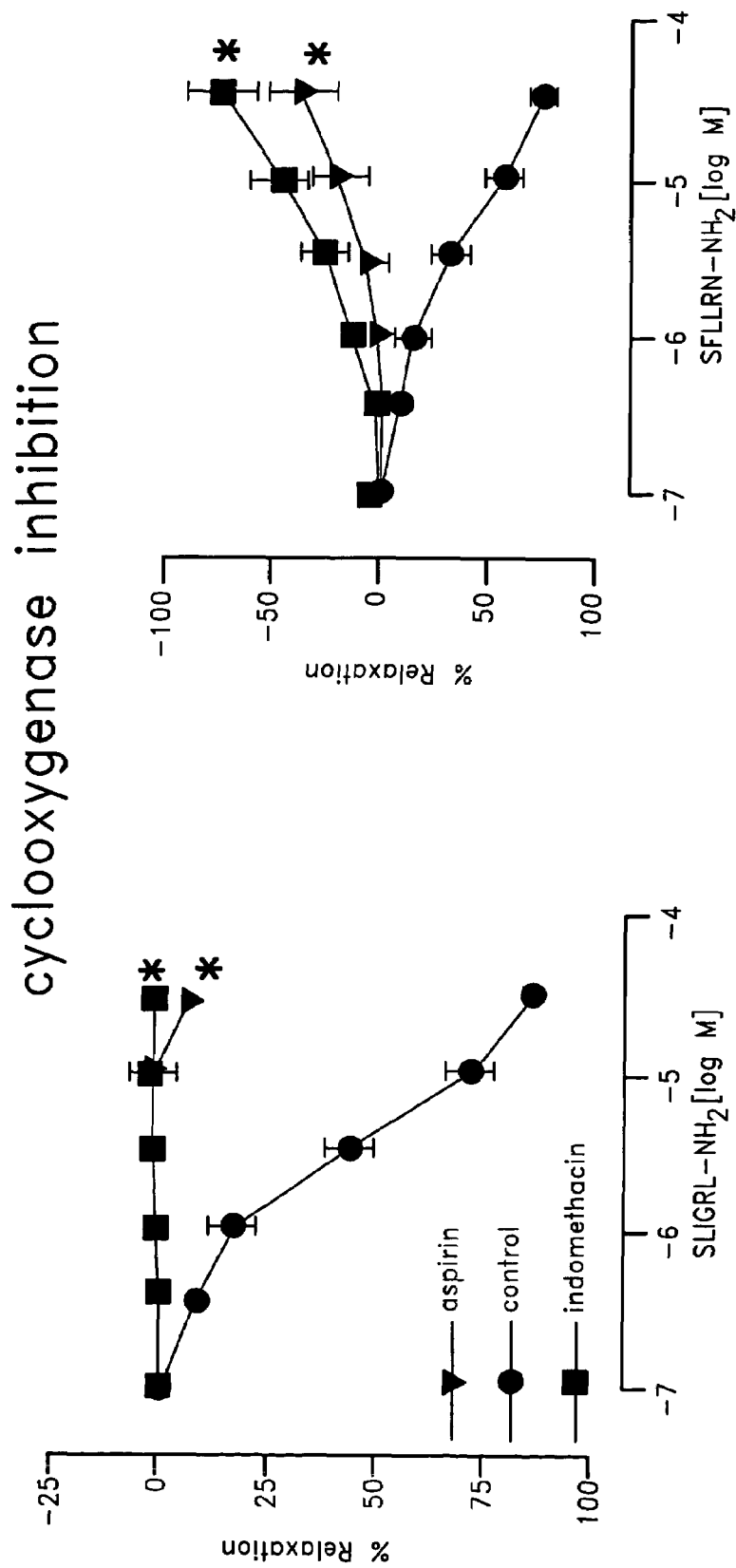
Figure 27C:
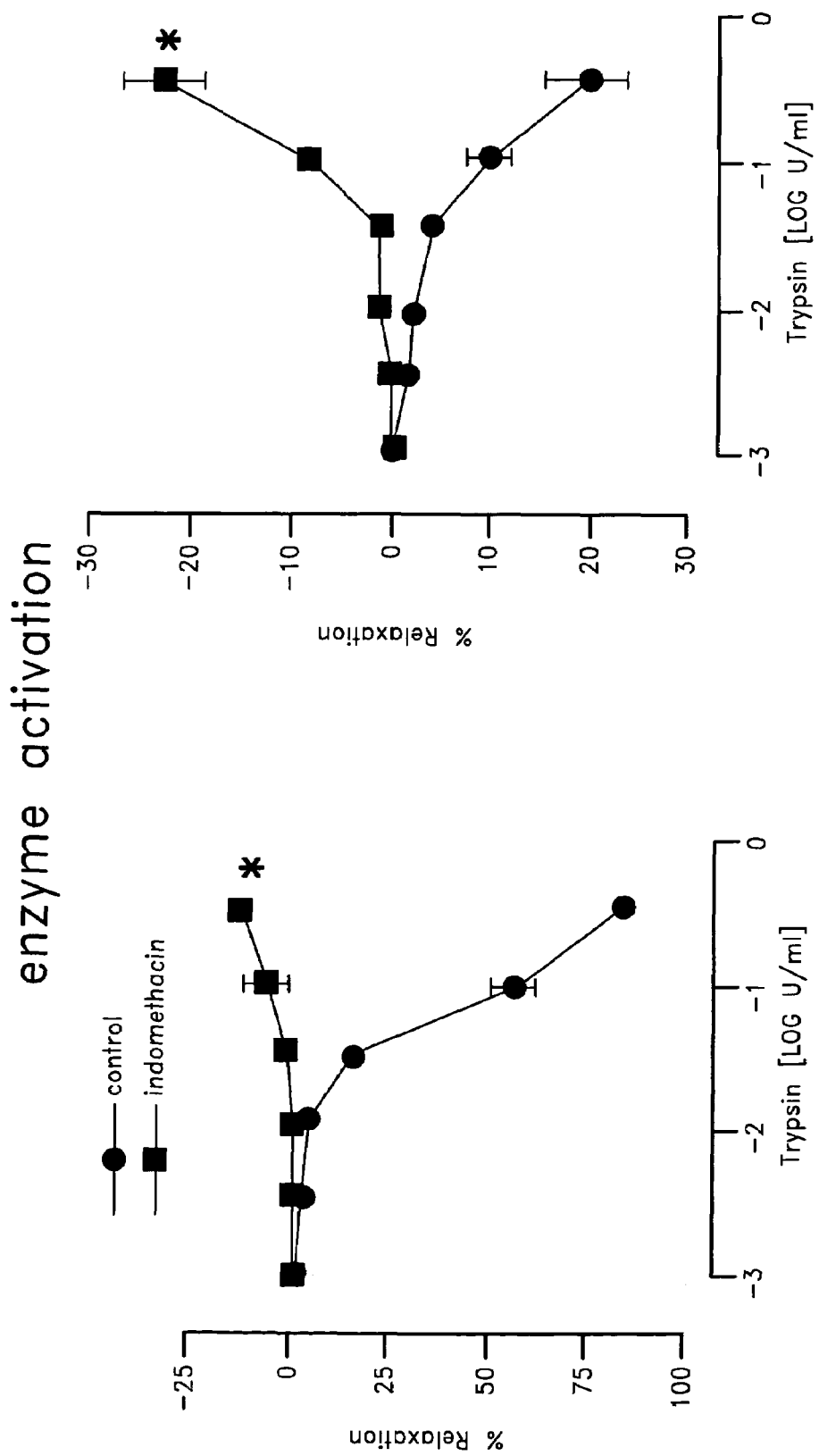

The mouse PAR2 tethered ligand sequence, SLIGRL—$NH_2$ (SEQ ID NO:2) (Nystedt et al, 1994) and trypsin each caused concentration-, epithelium- and cyclooxygenase-dependent, rapid onset and near-maximum relaxations of mouse bronchial rings contracted with the stable muscarinic agonist carbachol, as shown in FIGS. 26b and c and FIG. 27. For SLIGRL—$NH_2$ (SEQ ID NO:2) the sensitivity ($pEC_{50}$, –log M) was 5.6±0.1 and the maximum relaxation ($R_{max}$) was 94±3%. Similar concentration-dependent relaxations were also obtained to the PAR1 tethered ligand sequence SFLLRN—$NH_2$ (SEQ ID NO:1) (Dery et al, 1998) [$pEC_{50}$ 5.6±0.1; $R_{max}$ 76±11%] and thrombin. In contrast to PAR2, however, both removal of the epithelium and inhibition of cyclooxygenase with either indomethacin or aspirin unmasked direct smooth muscle contractions to PAR1 activation, as shown in FIGS. 26 and 27. Neither of the relaxations to SLIGRL—$NH_2$ (SEQ ID NO:2) and SFLLRN—$NH_2$ (SEQ ID NO:1) was due to nitric oxide (NO11, since they were completely unaffected by the NO synthase inhibitor, $N^G$-nitro-L-arginine (100 μM) either alone, or in combination with the NO scavenger, oxyhaemoglobin (20 μM), a combination of NO inhibitors which abolishes all NO release from vascular endothelial cells in situ (Drummond and Cocks, 1996; Kemp and Cocks, 1997). Therefore, these results indicate that a prostanoid released from the epithelium mediated the relaxations to both PARs. $PGE_2$ is a likely candidate, since it is the most prevalent prostanoid released from the airway epithelium, as shown in FIG. 26, and the inventors found it to be a potent bronchodilator in this tissue, causing 100% relaxation with a pEC$_{50}$ of 8.2±0.1 (n=6).

Figure 28A:
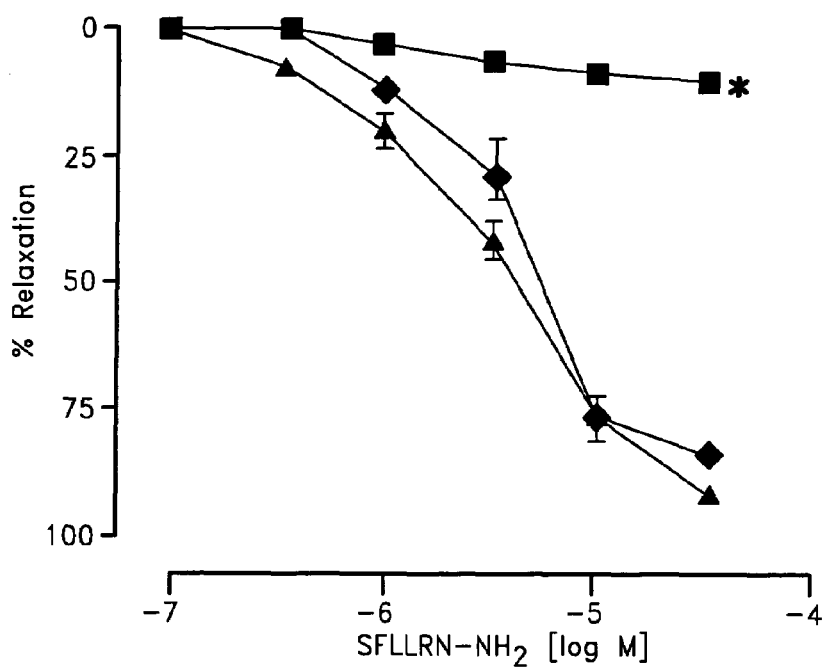
FIGS. 28A–28B show that the PAR1- and PAR2-activating peptides SFLLRN—NH$_2$ (SEQ ID NO:1) and SLIGRL—NH$_2$ (SEQ ID NO:2) respectively, act at separate receptors to cause bronchial relaxation. Desensitization to trypsin (■) but not to thrombin (▲) abolished the responses to the PAR2 peptide, SLIGRL—NH$_2$ (SEQ ID NO:2) (a), whereas relaxation to the PAR1 peptide, SFLLRN—NH$_2$ (SEQ ID NO:1), was markedly inhibited following desensitization to both enzymes (b). In both cases, (•) represents control responses. Values on the graphs are mean±s.e. mean from 5–6 experiments. *P<0.01
Figure 28B:
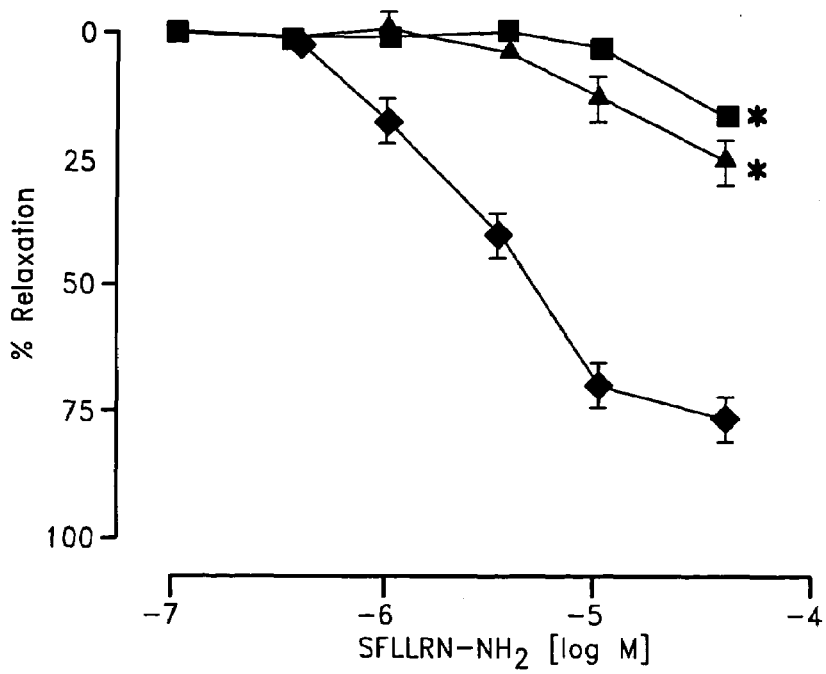

The relaxations to SLIGRL—NH$_2$ (SEQ ID NO:2) and SFLLRN—NH$_2$ (SEQ ID NO:1) in the mouse bronchi were likely to have been due to activation of separate receptors, since those to SLIGRL—NH$_2$ (SEQ ID NO:2) were abolished by prior desensitisation to trypsin but not thrombin whilst those to SFLLRN—NH$_2$ (SEQ ID NO:1) were inhibited by both thrombin and trypsin, as shown in FIG. 28. Also, desensitisation with SLIGRL—NH$_2$ (SEQ ID NO:2) blocked the response to trypsin. This pattern of activity agrees with previous reports showing that thrombin only activates PAR1 while higher concentrations of trypsin can activate both PAR2 and PAR1 (Vu et al, 1991; Molino et al, 1997).

EXAMPLE 14

Lung Inflammation Studies

Mice were challenged with bacterial lipopolysaccharide (LPS; 10 μg/mouse) via intranasal administration under light halothane aneasthesia. Prior to this challenge, mice were treated with SLIGRL—NH$_2$ (SEQ ID NO:2) (2 mg/kg or 20 mg/kg) or saline (control) via the same route of administration.

Three hours after receiving LPS, the mice were killed via an intraperitoneal injection of sodium pentabarbitone and the lungs were canulated and lavaged with 4×0.5 ml washes of phosphate buffered saline. The total number of cells retrieved by this procedure was determined with a haemocytometer. Differential counts of individual cell types were performed on cytospin preparations of the lavage fluid, stained with the conventional May-Grunwald/Giemsa blood stain. The total number of neutrophils in each sample was then calculated from the proportion of neutrophils in the cytospin preparations, as a proportion of the total number of cells retrieved. In animals which received neither LPS or SLIGRL—NH$_2$ (SEQ ID NO:2), very few neutrophiis were observed.

Figure 36:
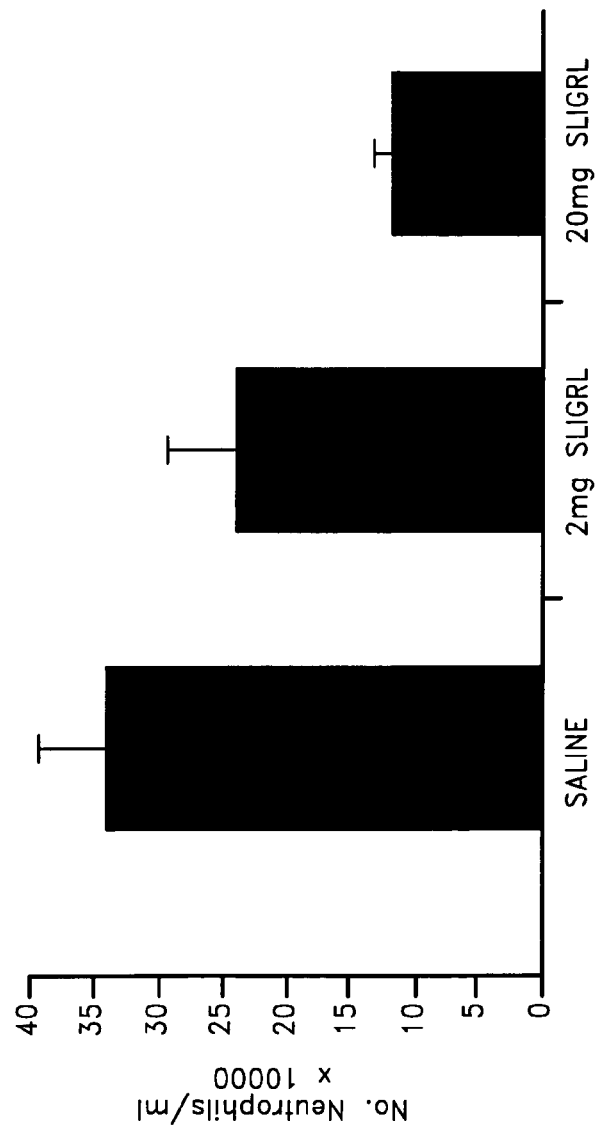
FIG. 36 is a graphical representation showing the effect of inhaled SLIGRL (SEQ ID NO:2) on LIDS induced neutrophil recruitment in murine lungs.

FIG. 36 shows group data for n=7 controls, n=3 at 2 mg/kg SLIGRL (SEQ ID NO:2) and n=6 at 20 mg/kg SLIGRL (SEQ ID NO:2). Clearly prior treatment with SLIGRL (SEQ ID NO:2)causes a dose-dependent inhibition of the increase of neutrophil infiltration into the lungs in response to LPS.

These data further show that activation of epithelial PAR2 evoke a generalised bronchoprotective response in the airways.

EXAMPLE 15

Ussing Methods for Determination of PAR-Induced Changes in Airways Epithelial Ion Transport Methods Mice were killed by a lethal overdose of sodium pentobarbitone and the tracheae rapidly excised. The trachea was opened longitudinally through the ventral cartilage rings to make a fiat sheet. Each sheet of trachea was mounted between two perspex chambers so that the mucosal (luminal) and submucosal and bathed with warmed, oxygenated Krebs' solution, independently on each side. Electrodes in the chambers allowed recordings of transepithelial potential difference using an amplifier. The tissue was voltage clamped at 0 mV by passing a current from the amplifier via another set of electrodes in the chambers. The amount of current required to maintain voltage at 0 mV is defined as the short circuit current (Isc) and is conventionally used as a measure of all ionic fluxes across the preparation.

Human airways were obtained from discarded sections of lungs of patients undergoing lobectomy operations at the Royal Melbourne Hospital, Melbourne, Australia usually for lung cancer. The dissection and set up were as described above for the mouse trachea.

After an equilibration time of 30 min, compounds for testing and drugs to elucidate the mechanism of any changes in Isc to the test compounds were added to either side of the tracheal epithelium (ie to either bath). Compounds used for increasing Isc were PGE$_2$, adenosine 5'-triphosphate (ATP), uridine 5'-triphosphate (UTP) and the PAR1-, PAR2- and PAR4-activating peptides, SFLLRN (SEQ ID NO:1) and SLIGRL (SEQ ID NO:2) and GYPGQY (SEQ ID NO:6), respectively. These stimulants were added cumulatively with controls for any time-dependent tachyphylaxis.

Results

Mouse Trachea

Figure 30:
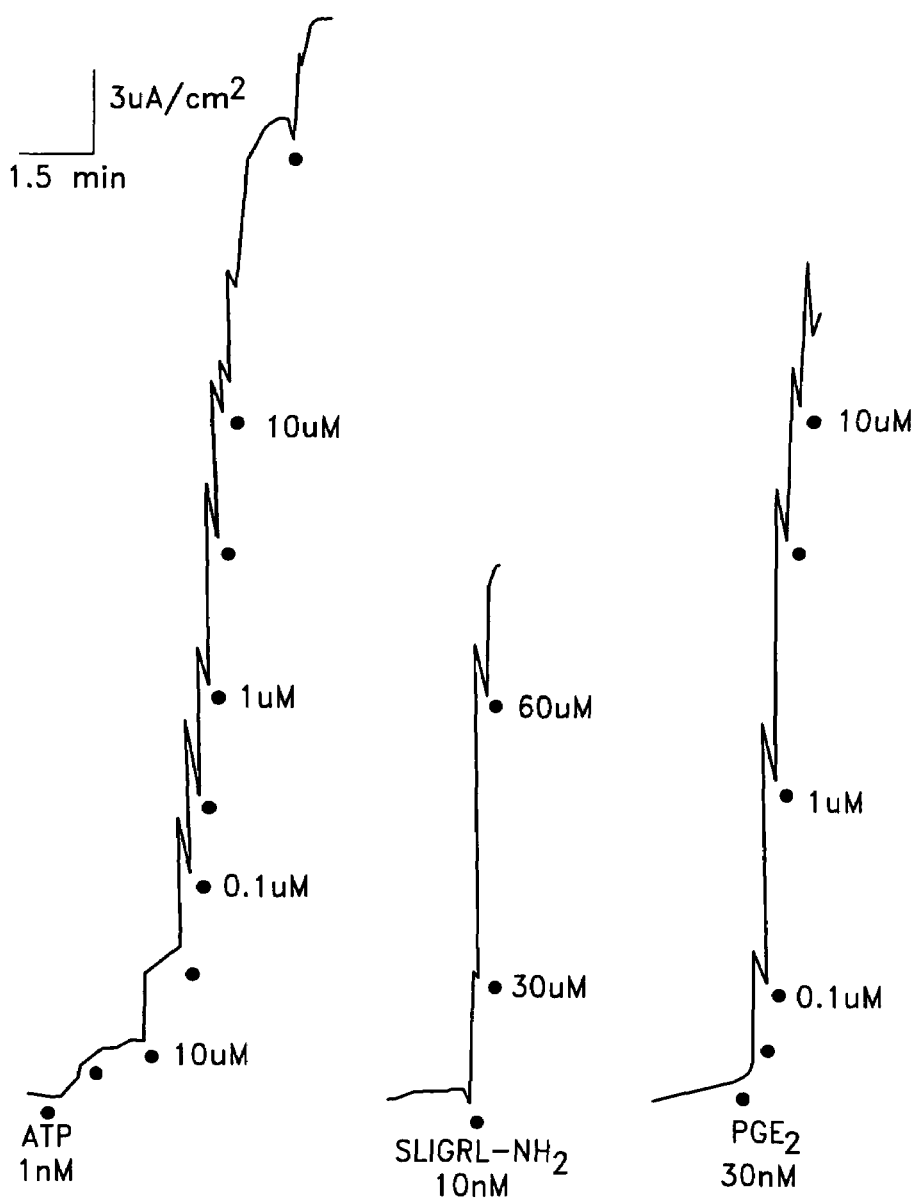
FIG. 30 is a graphical representation showing digitised traces of original chart recordings of increases in Isc to ATP, the PAR2 synthetic ligand; SLIGRL—NH$_2$ (SEQ ID NO:2) and PGE$_2$ in mouse trachea mounted in an Ussing Chamber. All drugs were applied on the apical surface.
Figure 31:
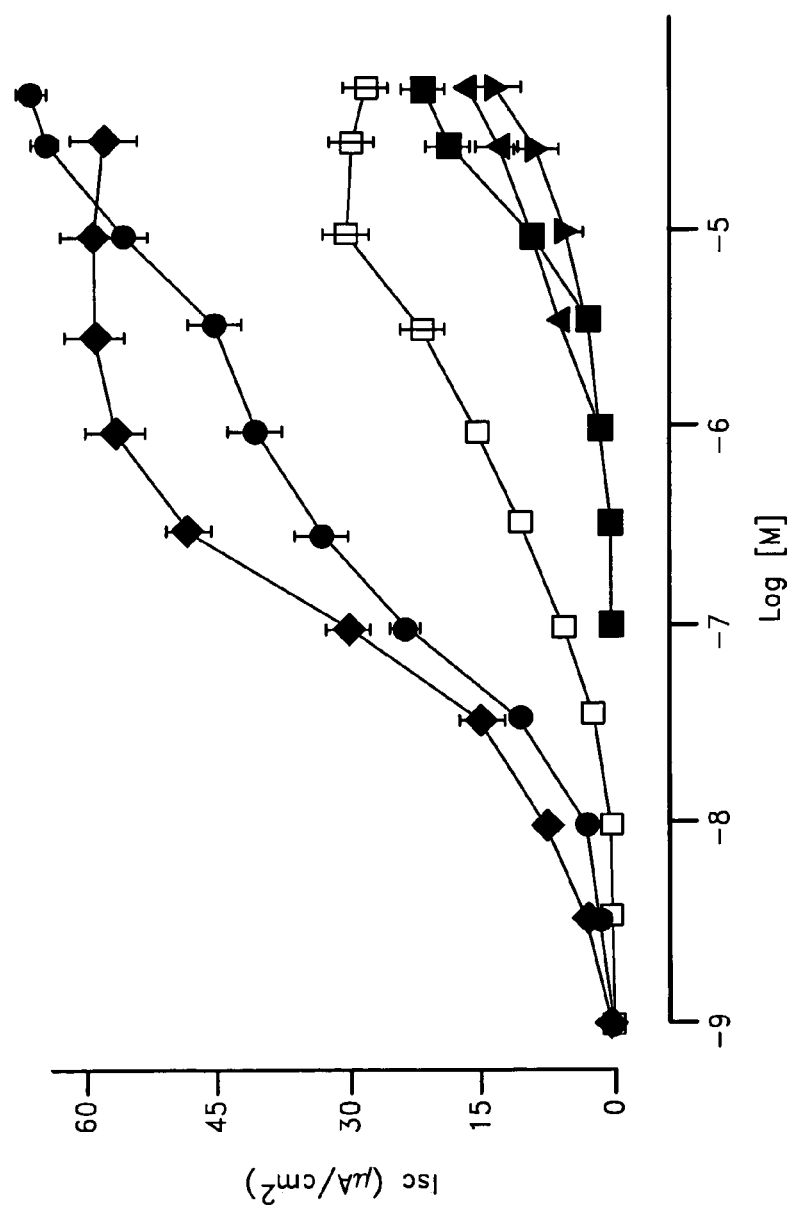
FIG. 31 is a graphical representation showing concentration-dependent increase in short circuit current (Isc) in mouse trachea mounted on the Ussing Chamber (see methods). Cumulative concentrations of SLIGRL—NH$_2$ (SEQ ID NO:2) (■), SFLLRN—NH$_2$ (SEQ ID NO:1)(▲), GYPGKF—NH$_2$ (▼), PGE$_2$ (♦), ATP (•) and UTP (□) were added to the luminal bath. Values on the graphs are mean±SEM from 5–6 experiments.
Figure 32C:
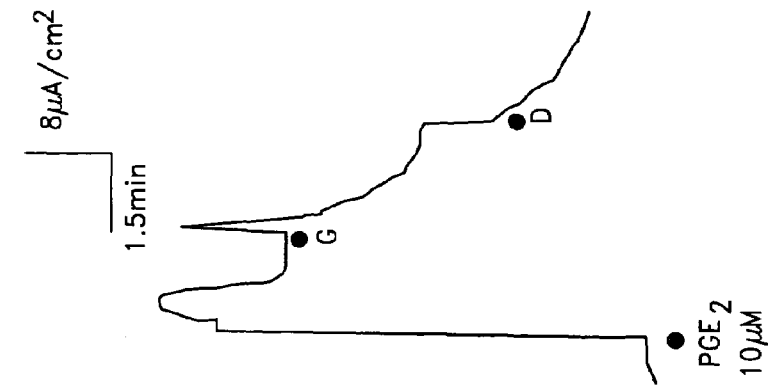
FIGS. 32A–32C show graphical representations of the effect of CFTR and dependent $Cl^{-Ca2+}$ channel inhibition by glibenclamide (100 μM: G) and DIDS (4,4' diisothiocyanostilbene 2,2'-disulphonic acid, 100 μM: D) respectively on (a) SLIGRL—NH$_2$ (SEQ ID NO:2) (30 μm), (b) ATP (10 μm) and (c) PGE$_2$ (10 μM). Digitised traces of original chart recordings for responses in mouse trachea mounted on an Ussing Chamber are shown. All drugs were applied on the apical surface.
Figure 32B:
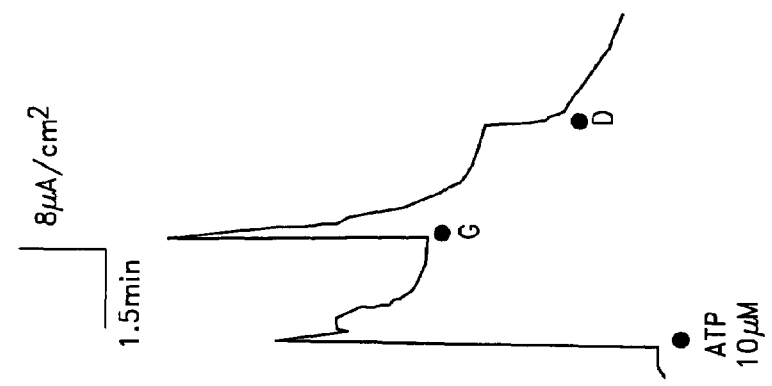
Figure 32A:
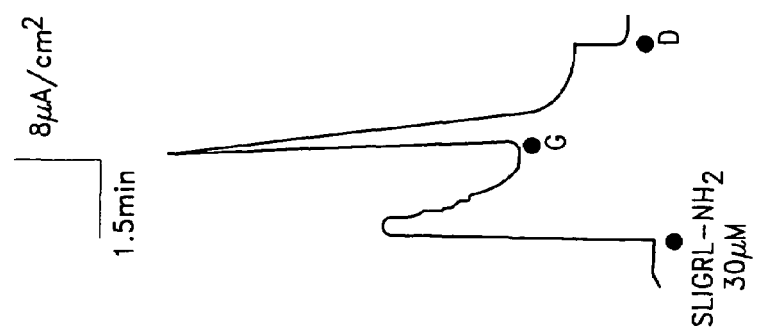
Figure 33A:
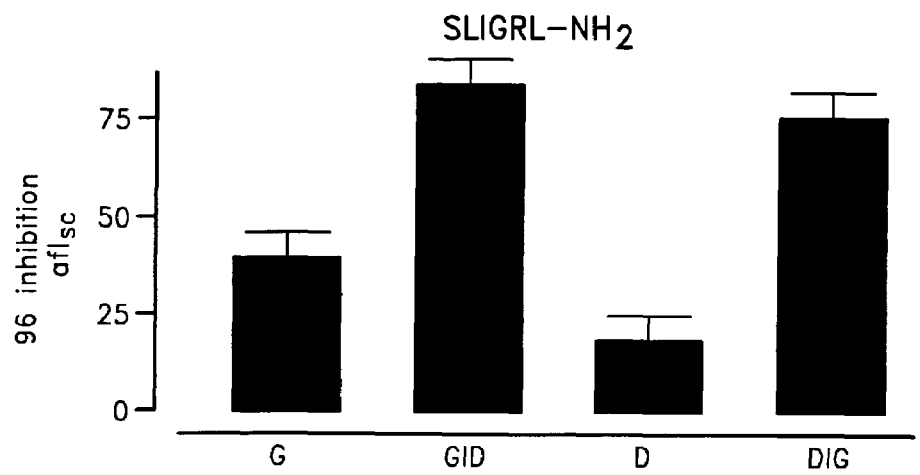
FIGS. 33A–33C show graphical representations of a mechanism of chloride secretion component of $1_{sc}$: the effect of glibenclamide (100 μM; G) alone or combined with 4,4'-diisothiocyanostilbene 2,2'-disulphonic acid (DIDs) (100 μM; G+D) or DIDS (100 μM; D) or combined with glibenclamide (100 μM; D+G) on (a) PAR2 synthetic ligand SLIGRL—NH$_2$ (SEQ ID NO:2) (30 μM). (b) ATP (10 μM) and (c) PGE$_2$ (10 μM) in isolated mouse trachea.
Figure 33B:
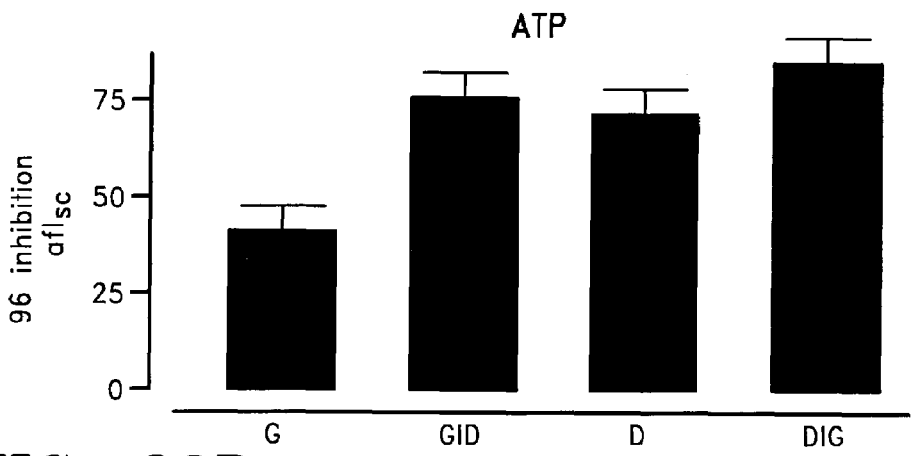
Figure 33C:
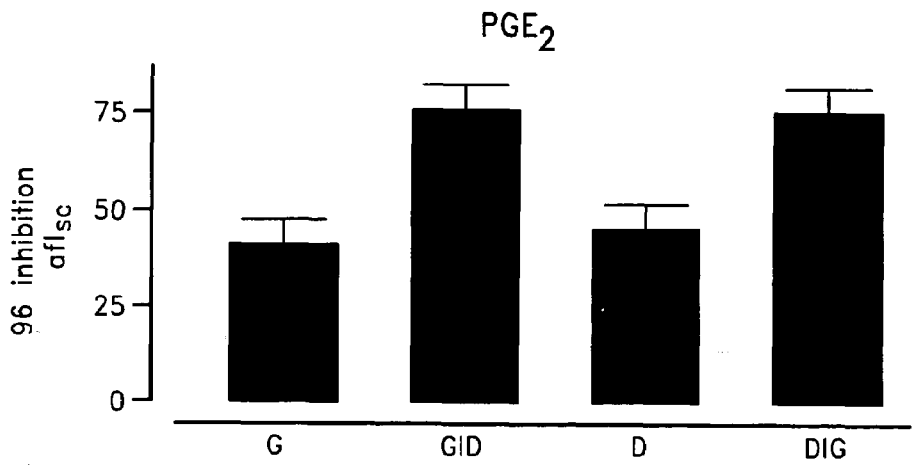

FIG. 30 shows typical original traces of the increases in Isc in response to luminally-applied ATP, SLIGRL (SEQ ID NO:2) and PGE$_2$. For all three cases, each concentration of activator caused a rapid initial rise in Isc usually followed by some degree of recovery until a steady plateau was reached. The group data for these and other activators is depicted in FIG. 31. FIG. 33 provides digitised traces of original chart recordings showing the effects of inhibitors of two distinct chloride channels on changes in Isc to single, submaximal concentrations of ATP, PGE$_2$ and SLIGRL (SEQ ID NO:2). The drugs used were glibenclamide (G), an inhibitor of the cystic fibrosis transmembrane regulator (CFTR; Schultz et al, 1999) and DIDS, an inhibitor of calcium-activated chloride channels (CICa; Gruber et al, 1999). From the group data for these experiments shown in FIG. 33, it can readily be seen that whilst most of the chloride conductance to SLIGRL (SEQ ID NO:2) was due to the CFTR channel, a substantial amount remained due to CICa. These increases in Isc to SLIGRL (SEQ ID NO:2), ATP and PGE$_2$ in the mouse airways were unaffected by the cyclooxygenase inhibitor, indomethacin.

Human Bronchi

Figure 34:
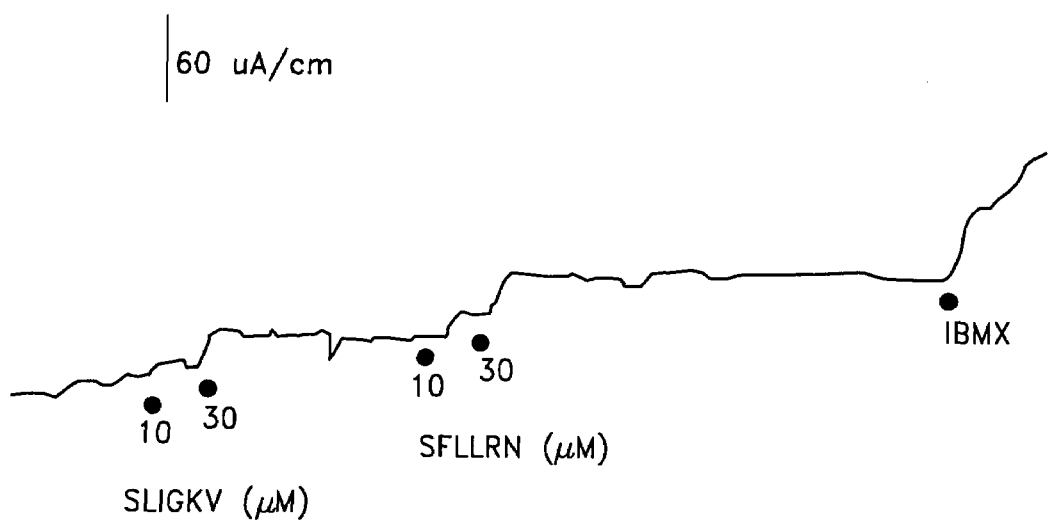
FIG. 34 is a graphical representation depicting increases in Isc to PAR2 and PAR1-activating peptides SLIGKV (SEQ ID NO:3) and SFLLRN (SEQ ID NO:1), respectively in human bronchial epithelium. The maximal response of the tissue, elicited by isobutylmethylxanthine is also shown.

FIG. 34 depicts increases in Isc to the PAR2- and PAR1- activating peptides, SLIGKV (SEQ ID NO:3) and SFLLRN (SEQ ID NO:1) respectively in the epithelium of a section of human intralobular bronchus. Prior to addition of the drugs shown, the preparation was incubated with amiloride, because secretory responses cannot be observed in human tissues unless sodium channels are inhibited by this drug. The maximum response elicited by the phosphodiesterase inhibitor, isobutylmethylxanthine (/BMX) is included. Note that the relatively poor response to the human PAR2- activating peptide, SLIGKV (SEQ ID NO:3), is in keeping with other data presented herein for PARE function (epithelium-dependent smooth muscle relaxation) and the apparent low level of expression of the receptor as determined by immunohistochemistry.

Discussion

Figure 35:
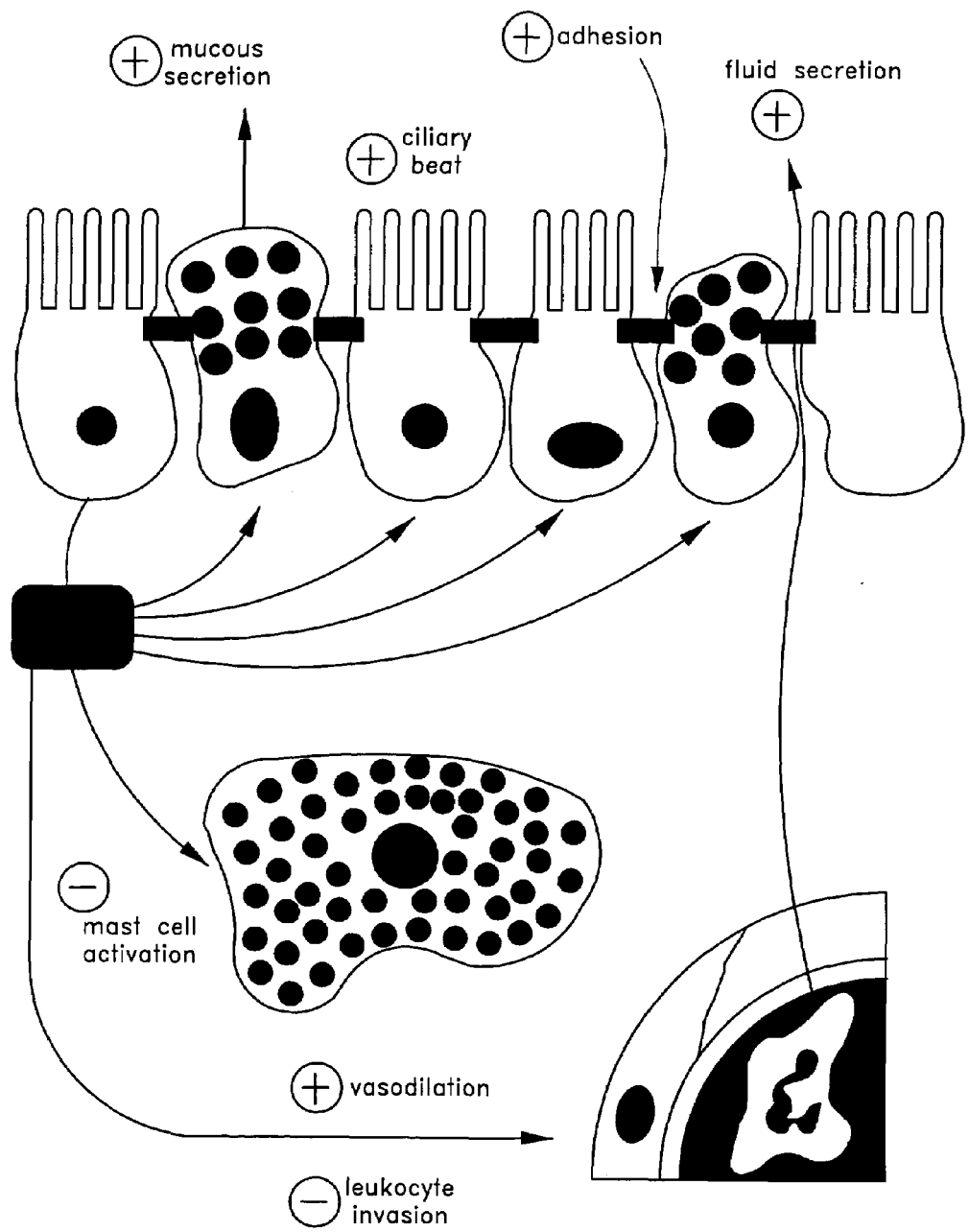
FIG. 35 is a diagrammatic representation showing cytoprotection by epithelium derived factors.

The finding that all three PAR-activating peptides increase chloride conductance in mouse airways and the preliminary data in human airways which shows that activation of PAR2 also increase Isc, further indicates that epithelial PARE in the airways (and most likely epithelial PAR1 and PAR4) are bronchoprotective. An increase in chloride secretion encourages water to follow and maintain the sol layer beneath the mucous layer (Boucher, 1999). Secretion of mucous from mucous goblet cells is also stimulated submucosally by $PGE_2$ (see FIG. 1) as is vasodilatation which enables fluid to follow the movement of ions. The finding that the increases in Isc to PAR2 and ATP did not involve a cyclooxygenase product (ie $PGE_2$) indicates that these receptors are directly linked to the two chloride channels underlying Isc changes as well as to the production of $PGE_2$ and its release into the submucosal compartment to orchestrate the many other anti-inflammatory mechanisms already alluded to (see FIG. 35).

An additional finding from this study may have important implications for treatment of people with cystic fibrosis (CF). These patients lack the CFTR and as a consequence the mucous layer in the airways becomes sticky due to the reduction in the efficiency of production of the layer of fluid normally maintained by the conductance of chloride through the CFTR (Boucher, 1999). Because CF' patients cannot move airway mucous and its entrapped pathogens, their lungs become persistently inflamed by bacterial infection, resulting ultimately premature (<30 yr) death. Activators of the alternative ClCa particularly by ATP and UTP have recently attracted much attention as a possible new therapeutic approach to improving the lung function of CF patients (eg Olivier et al, 1996) since this channel is present in CF patients. The present finding that PAR2 activators can also activate the ClCa are novel and also potentially important given that this effect is concomitant with generalised bronchoprotection indirectly via the release of $PGE_2$. The fact that the PAR-activating peptides were not as potent or efficacious as ATP may be related to endogenous peptidases that cleave the peptide PAR agonists. Stable peptides or non-peptide PAR-activators would not be subject to this process.

EXAMPLE 16

Effects of PAR Agonists on Monkey Airways

Figure 37:
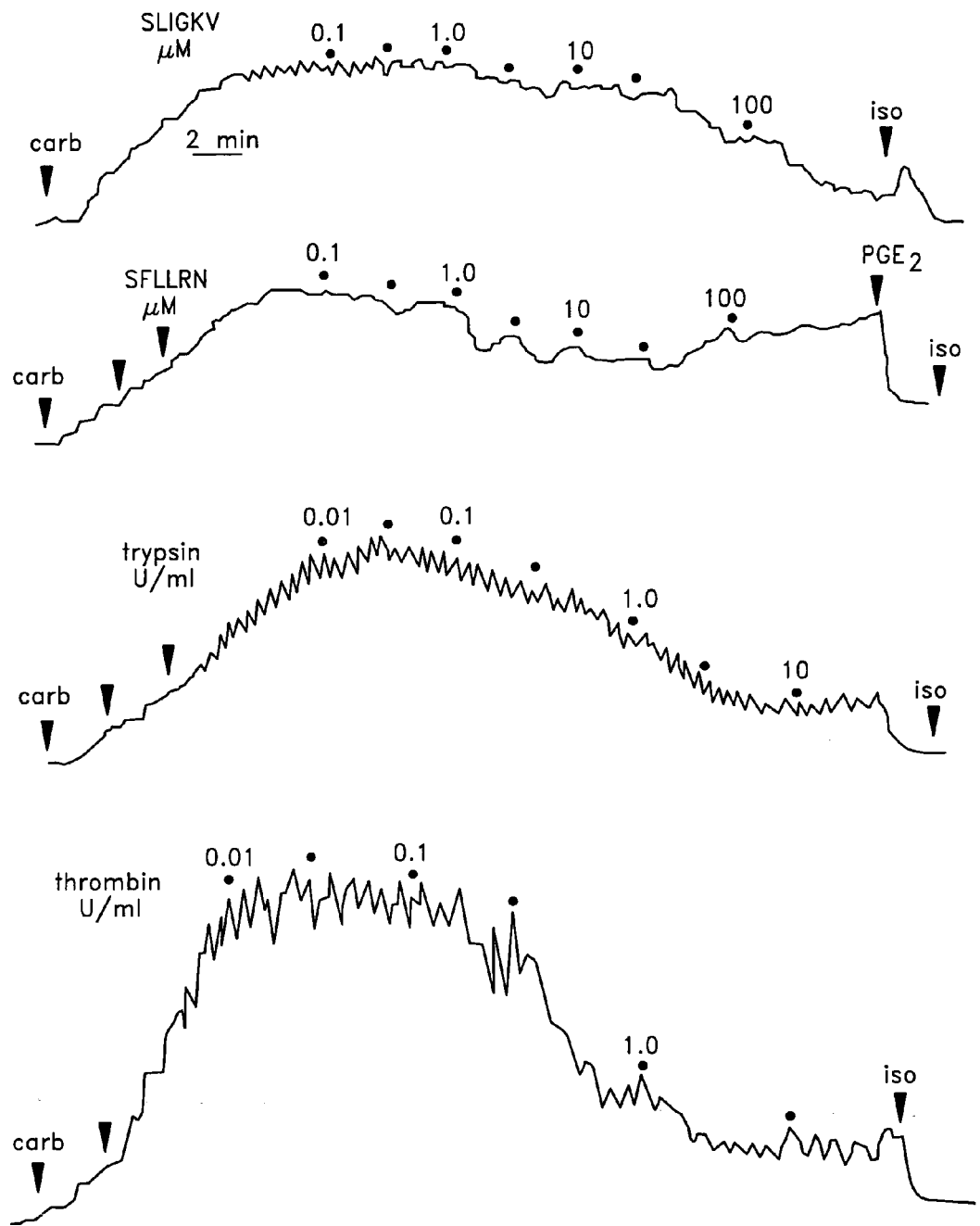
FIG. 37 is a graphical representation of digitised original chart recordings showing the smooth muscle relaxing effects of PAR1 and PAR2 peptide activators, SLIGKV (SEQ ID NO:3) and SFLLRN (SEQ ID NO:1) respectively and the PAR activating enzymes, thrombin (PAR1 selective) and trypsin (PAR2 selective) in isolated ring segments of monkey small bronchi. Traces are characteristic of similar tissues taken from four separate animals (two pigtail macaques; two cynamologus). The experimental details are similar to those for the mouse isolated bronchi. Briefly, approximately 2 mm long rings of small bronchi were mounted on wire hooks. In each trace, half log concentrations are not depicted for clarity. In some cases PGE3 and isoprenaline (iso) were added to (1) show that these tissues were responsive to $PGE_2$ and (2) to obtain maximum tissue relaxation.
Figure 38A:
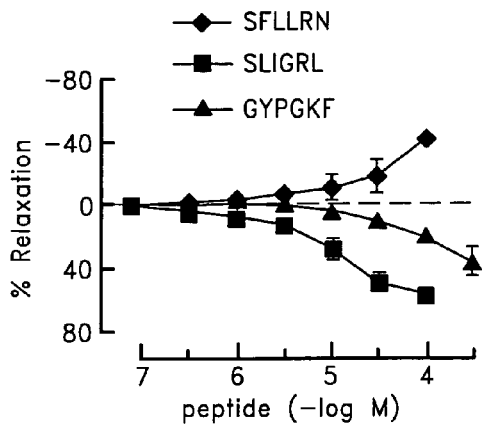
FIGS. 38A–38F show graphical representations of cumulative concentration in response curves to PAR1-, PAR2- and PAR4-activating peptides.
Figure 38B:
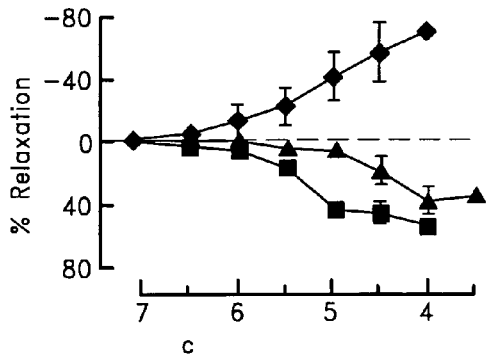
Figure 38C:
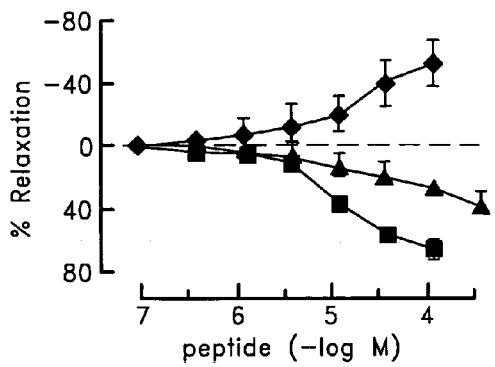
Figure 38D:
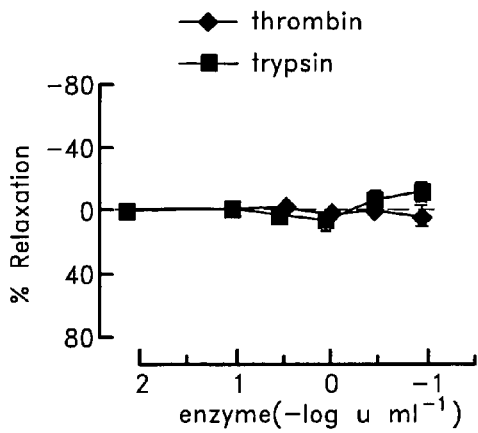
Figure 38E:
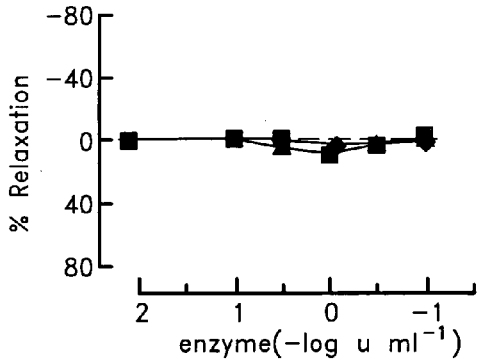
Figure 38F:
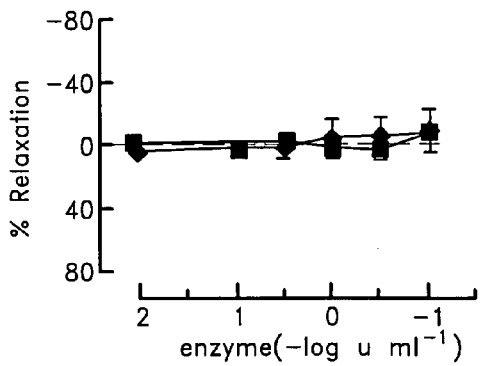

FIG. 37 is a representation of digitised original chart recordings showing the smooth muscle relaxing effects of PAR1 and PAR2 peptide activators, SLIGKV (SEQ ID NO:3) and SFLLRN (SEQ ID NO:1) respectively and the PAR activating enzymes, thrombin (PAR1 selective) and trypsin (PAR2 selective) in isolated ring segments of monkey small bronchi. Traces are characteristic of similar tissues taken from four separate animals (two pigtail macaques; two cynamologus). The experimental details are similar to those for the mouse isolated bronchi. Briefly, approximately 2 mm long rings of small bronchi were mounted on wire hooks. In each trace, half log concentrations are not depicted for clarity. In some cases $PGE_2$ and isoprenaline (iso) were added to (1) show that these tissues were responsive to $PGE_2$ and (2) to obtain maximum tissue relaxation.

EXAMPLE 17

Effects of PAR Agonists on Rat Airways

FIG. 38 provides cumulative concentration-response curves to the PAR1, PAR2 and PAR4-activating peptides, SFLLRN (SEQ ID NO:1), SLIGRL (SEQ ID NO:2) and GYPGKF and the PARactivating enzymes, thrombin and typsin in isolated rat trachea (a, d) bronchi (b, e) and first bronchi (c, f). Values are expressed as percentage relaxation or contraction from carbachol-induced contraction (mean±s.e. mean %, n=6–12). Confocal microscopic imaging was used to confirm the immunohistochemicailocalisation of PAR2 in rat trachea, bronchi and intrapulmonary bronchi. Colocalisation of PAR2 immunofluorescence with two separate PAR2 antibodies, PAR2-C antibody (green) and PAR2-N antibody (red) superimposed images show as yellow staining.

EXAMPLE 18

PAR-Like Receptor

Activation of PAR-like receptor results in endothelium-dependent, NO-mediated relaxation of contracted human coronary arteries in vitro. This receptor either has a common, low stringency "hirudin-like" thrombin binding domain, or other binding domains such that serine proteases other than thrombin (eg. trypsin) can sensitively activate it. This receptor also appears to be recycled via a mechanism whereby cleaved (activated) receptors are returned to the membrane, and are able to respond to agonists acting independently of receptor cleavage. The pathophysiological roles of endothelial cell PARs in human coronary arteries are unknown, although one possibility is that by inducing a vasodilator response, these receptors may limit the degree of thrombosis following plaque invasion by mast cells, as this process is known to be associated with release of proteases such as the trypsin like enzyme, tryptase (Kovanan et al, 1995). The non-selectivity to activation of this novel PAR receptor by thrombin and trypsin may also extend to other proteases.

The studies described herein have identified functional PAR1 and PAR2 in the bronchi of mouse, rat, domestic pigs and guinea-pigs which, when activated by specific proteases, thrombin and trypsin or the human PAR1 and mouse PAR2 tethered ligand sequences, SFLLRN—$NH_2$ (SEQ ID NO:1) and SLIGRL-$NH_2$ (SEQ ID NO:2) respectively, cause profound relaxation of bronchial muscle. PAR2, and most likely PAR1 are located in the epithelium, and when activated, mediate smooth muscle relaxation via the release of endogenous prostaglandin (PG), most likely $PGE_2$. This relaxation was as rapid and complete as that for isoprenaline, the clinically most efficacious and rapidly acting beta-adrenoceptor agonist bronchodilator currently available.

The inventors have demonstrated for the first time that two types of PAR receptors, PAR1 and PAR2, are located on bronchial epithelial cells. Without wishing to be limited by any proposed mechanism, the inventors postulate that activation of these receptors mediates relaxation of the airway by stimulating release of PG, most likely $PGE_2$, an endogenous local hormone. This relaxation is as efficient and rapid as that elicited by the most effective known bronchodilator drugs, the beta-2-adrenoceptor agonists, exemplified herein by isoprenaline. Therefore, the findings described herein demonstrate that activation of PAR stimulates activation of a potent and highly efficient protective mechanism that operates to keep the airways open. Furthermore, the $PGE_2$ released by PAR activation may have an important role in protecting airway tissue from pathological change by regulating tissue 5 responses to injury and regulating mucosal immunity.

The studies disclosed herein are not only the first to describe functionality for PAR2 and PAR1 in the airways, but they also show that PAR2 activation results in powerful epithelium-dependent bronchodilatation with no evidence for direct contraction, even though PAR2 was also localised on smooth muscle cells. As described herein the mouse, PAR2 is also expressed in both the epithelium and smooth muscle cells of human airways.

This dual localisation to PAR2 to the mucosal and submucosal layers of the airways is important, however, since it reconciles the inventors' proposal that epithelial PAR2 is anti-inflammatory, with the current dogma that like PAR1, PAR2 is pro-inflammatory (Dery et al, 1998), possibly being activated by mast cell-tryptase (Molino et al, 1997). Thus, the inventors propose a dual compartment model for the role of PAR2 in the air ways. In this model, anti-inflammatory epithelial PAR2 (compartment 1) normally override any pro-inflammatory effects of smooth muscle and perhaps fibroblast PAR2 (compartment 2) activated by mast cell tryptase, since PGE, potently inhibits mast cell activation. It is interesting to note that trypsin has been localised in epithelial cells of normal human airways. The inventors confirmed this finding and furthermore localised specific trypsinogen immunofluorescence to Clara cells in human bronchi. Therefore, in this model, epithelial and smooth muscle PAR2 may be differentially regulated by specific tryptic enzymes released preferentially in each compartment.

Based on these findings and the vasodilator effects of PARs in blood vessels, it appears that PAR activation is a general protective mechanism relevant, but not limited, to epithelia of bronchi and vessels, mucosal surfaces and joint connective tissues. Defects in this system may be important determinants of disease susceptibility and severity. Since PARs are activated by tissue injury and proteases are released both during innate and acquired immune responses, this invention has broad application to numerous disease states where deficient intrinsic protection from injury contributes to disease pathogenesis and/or severity. Therefore, the present invention has wide application in the design of diagnostic and therapeutic strategies for managing these conditions.

The invention makes possible new treatments for many, if not most, inflammation-related diseases of the airways. It may also apply to a therosclerosis in blood vessels, as well as to similar inflammation-mediated diseases of other muscle-lined tubes in the body, such as the bile duct, urogenital tract etc). The mechanism of relaxation of the PAR of the present invention offers scope for avoiding the limitations of beta-2 therapy. Treatment of inflammation-induced insufficiency in airways, for example in asthma, via this new pathway involves activation of a naturally-occurring system. Thus, it offers the prospect of being able to cure these diseases with gene therapy techniques, particularly given the easy route of access for adding the extra copies of the PAR2 gene. It also offers a possible solution to the long-standing problem as to why the airways of healthy individuals are protected from obstruction, whereas those of asthmatics are not protected. Furthermore, the need for vascular endothelial and airway epithelial cells to replace PAR2 quickly implies that they serve a protective function, rather than causing cell damage as previously believed, due to the potentially deleterious effects of mast cell-derived tryptase in preventing or treating infection.

Figure 12:
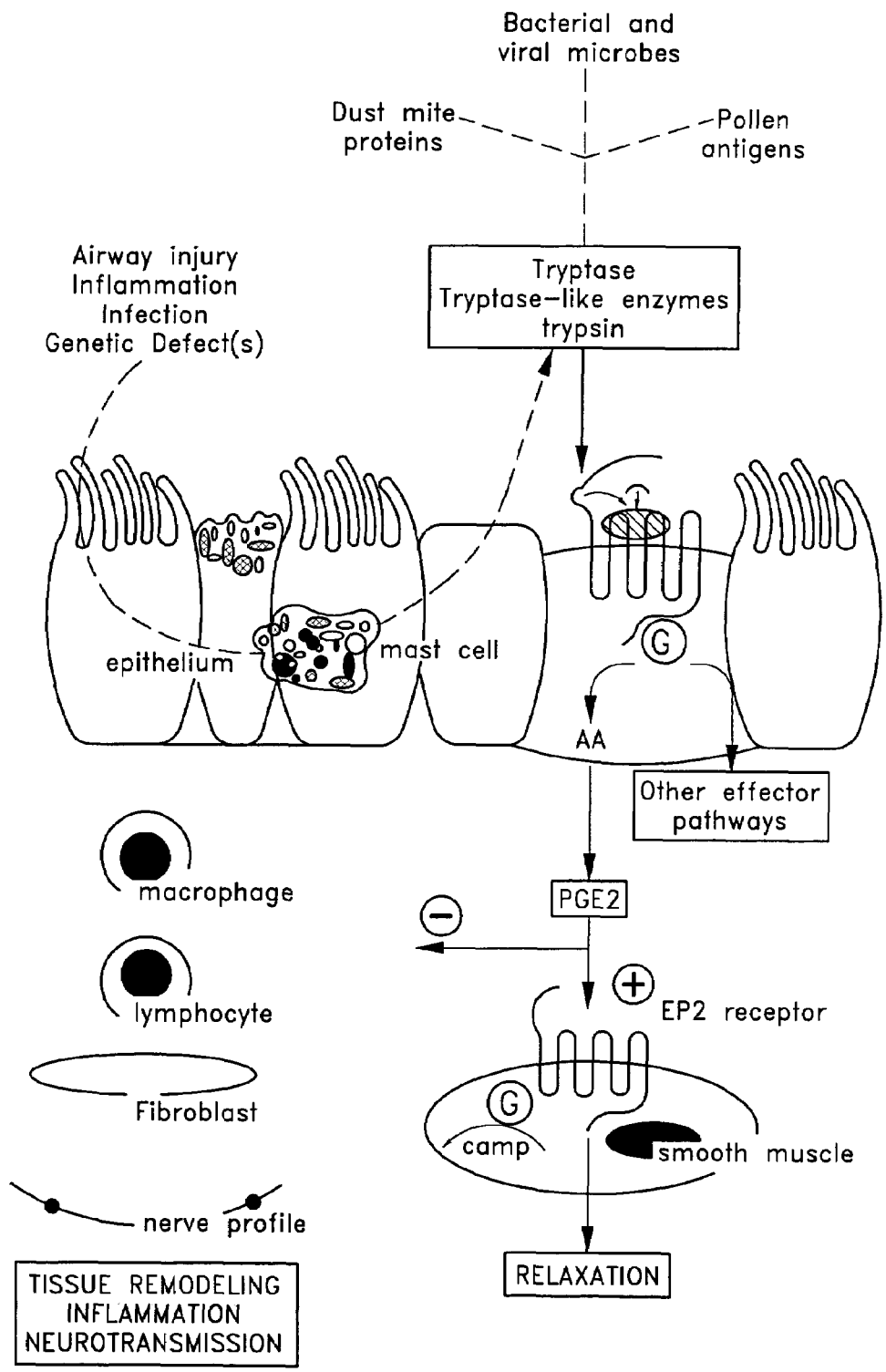
FIG. 12 is a schematic representation of the proposed broncho-protective role of PAR2 in the airways. The pathways denoted by the thick solid arrows (from activation of epithelial PAR2 by tryptase-like enzymes including trypsin to release of PGE$_2$, and its subsequent activation of EP$_2$ receptors to initiate cAMP-dependent smooth muscle relaxation or other possible beneficial actions of endogenously released PGE$_2$ are powerfully operational in the bronchi. The broken arrows indicate local sources of tryptase and tryptase-like enzymes and their relationship to inflammation. The: same protective mechanisms would be activated by thrombin-mediated stimulation of epithelial PAR1.
Figure 13:
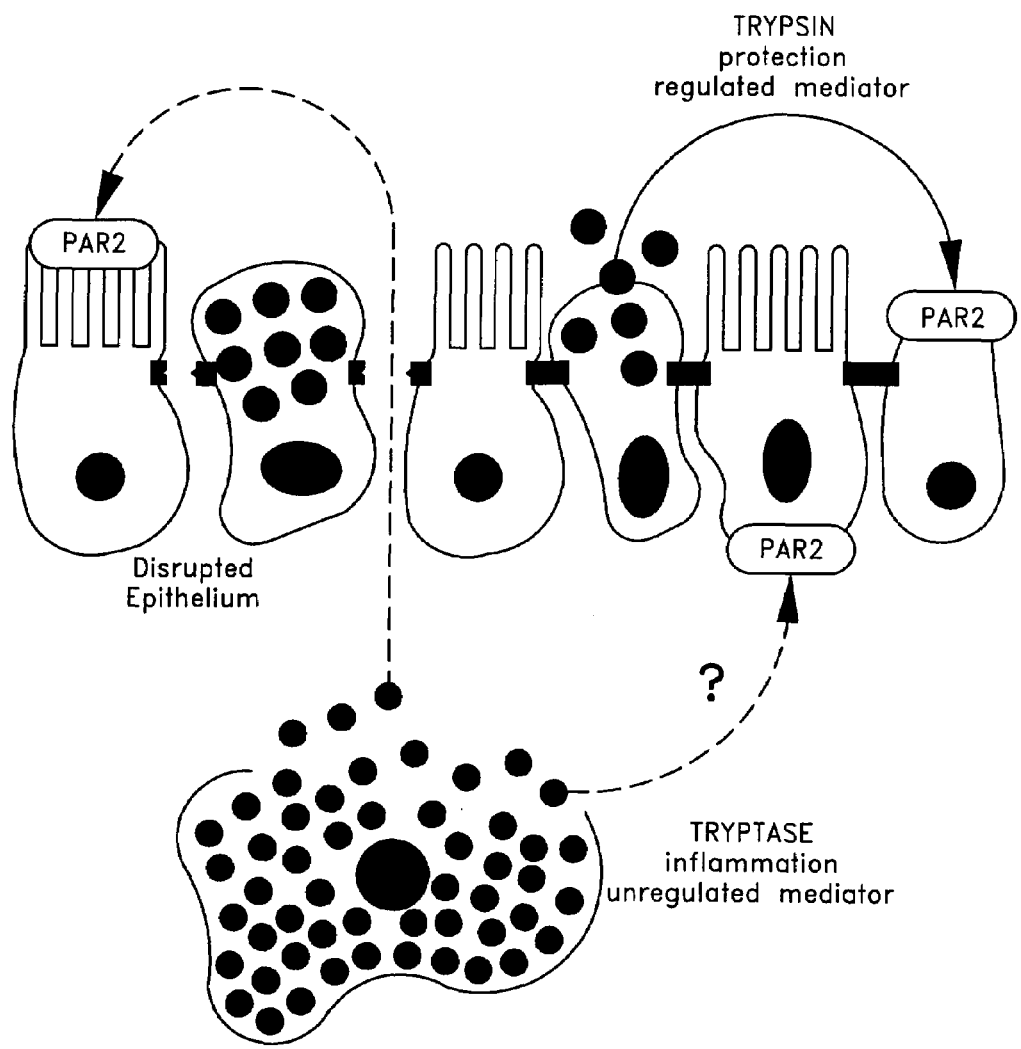
FIG. 13 is a diagrammatic representation of dual compartment model of PAR2 functionality in epithelial cells. PAR2, expressed by epithelial cells, serves to sense tryptic enzymes released by the epithelium itself during defensive reactions. Activation of PAR2 by these enzymes results in cytoprotection via the many means already alluded to in this patent. In contrast, mast cell tryptase, an enzyme potentially able to activate PAR2, cannot activate PAR2 because the epithelial barrier prevents it from gaining access to the tops of epithelial cells were PAR2 is concentrated. However, if the epithelium is disturbed then mast cell tryptase gains access to PAR2, which it may chronically activate because there are no endogenous activators of this enzyme. In contrast, epithelia produce proteins that inhibit epithelium-derived enzymes like trypsin. Hence trypsin can only mediate short-term, protective effects. Also indicated is that some epithelial cells may express PAR2 on their bottom surfaces, perhaps mediating some effects of mast cell tryptase. To date, PAR2s have never been observed in this position in airway tissues of any species.

The findings described herein not only demonstrate that blood vessels and airways are similar in that their inner lining cells possess powerful smooth muscle relaxing mechanisms, but also suggest that PARs may orchestrate a more general endogenous protective tissue response to inflammatory challenge and disease, which includes regulation of smooth muscle contractility, inflammatory cell migration and function, neural activity and tissue remodelling. PARs are ideally configured for such a role. They are in effect "caged", theoretically lying dormant until activated by specific proteases, many of which are known to be involved in airway immune and inflammatory responses, as depicted in FIG. 12.

Furthermore, following activation they are inactivated by rapid internalisation, which then signals equally rapid replenishment of new receptors from intracellular pools and de novo protein synthesis from stably expressed mRNA. Finally, the location of PARs to the epithelium is ideal for mediating such protease-dependent responses to airborne allergens, particularly suppression of contractility in the underlying smooth muscle.

Prostaglandin E2 and Asthma

Although the potentially beneficial effects of $PGE_2$ as a relaxant agent, modulator of immune responses and regulator of tissue response to injury have been appreciated for some time, it has not proven possible to deliver $PGE_2$ or mimetics safely to the airways (Nizankowska et al, 1985; Daniell et al., 1994 and Melillo et al, 1994). The major limitation to exploiting the benefits of $PGE_2$ has been that exogenous $PGE_2$:

(i) potently activates sensory nerves in the airways, causing severe coughing (Costello et al, 1985; Stone et al, 1992; and (ii) dysregulates airway mucosal blood flow (Laitinen et al, 1987).

Regardless of these limitations for exogenously applied $PGE_2$, $PGE_2$ has several actions likely to be of considerable benefit in asthma. $PGE_2$ suppresses cholinergic bronchoconstriction reflexes at the level of acetylcholine release. $PGE_2$ potently inhibits activation of macrophages and lymphocytes, both of which are implicated in the pathogenesis of chronic human asthma. $PGE_2$ also suppresses the formation of new tissue matrix by inhibiting activation of mesenchymal cells such as airway fibroblasts. It is of considerable interest that asthmatics may die from catastrophic bronchospasm if cyclooxygenase is inhibited. There is also a large body of evidence that $PGE_2$ can be generated by the normal epithelium of airways, as well as by macrophages and airways cartilage. $PGE_2$ administered by aerosol protects asthmatics from exercise-induced asthma and from induced mediator-induced bronchospasm (eg with methacholine), although it is tolerated very poorly.

Therefore, the present invention represents a novel method to harness the therapeutic potential of $PGE_2$ by causing its endogenous release within tissues.

In conclusion, and without wishing to be bound by any proposed mechanisms for the observed advantages, it appears that PARs mediate powerful epithelium dependent brochodilatation, most likely via $PGE_2$, which offers scope for new and effective therapies for airway inflammatory diseases like asthma and bronchitis. Also, individuals susceptible to inappropriate loss or down-regulation of the PAR2 protective defence would be more likely to develop disease or diseases of increased severity; this finding provides the basis for new diagnostic and prognostic methods.

Table 3 provides a summary of some of the characteristics of PAR1–PAR4 the four cloned PARs. The schema shown FIG. 1 depicts a common PAR weaving in and out of the plasma membrane of a cell. Cell signalling is initiated following G-protein coupling. Note that the chromosomal location given in Table 3 is for human PARs.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Glusa, E. and Markwardt, F. Biomed. Biochem. Acta, 47: 623–630, 1988.
Grubb, B R & Boucher, R C. Physiol. Rev., 79 (suppl. 7): S193–S214, 1999.
Gruber, A D, Schreur, K D, Ji, H-L, Fuller, C M & Pauli, B U. Am. J. Physiol., 276: C1261–C1270, 1999.
Hamilton, J. R. et al. Circ. Res. 82: 1306–1311, 1998.

TABLE 3

|  | PAR1 | PAR2 | PAR3 | PAR4 |
| --- | --- | --- | --- | --- |
| Selective enzyme activator | Thrombin | Trypsin | Thrombin | Thrombin and trypsin |
| Chromosome | 5q13 | 5q13 | 5q13 | 19p12 |
| Other enzyme activators | Trypsin Mast cell tryptase | Mast cell tryptase |  |  |
| Cleavage site (human) | -Arg$^{41}$-Ser$^{42}$- | -Arg$^{34}$-Ser$^{35}$- | -Lys$^{38}$-Thr$^{39}$- | -Arg$^{47}$-Gly$^{48}$- |
| Hirudin-like alignment site | Yes | No | Yes | No |
| Tethered ligand sequences | SFLLRN(h) (SEQ ID NO:1) TFRIFD(x) (SEQ ID NO:9) SFFLRN (m, r) (SEQ ID NO:10) | SLIGRL(m, r) (SEQ ID NO:2) SLIGKV(h) (SEQ ID NO:3) | TFRGAP(h) (SEQ ID NO:11) SFNGGP(m) (SEQ ID NO:12) | GYPGKF(m) (SEQ ID NO:6) GYPGQV(h) (SEQ ID NO:13) |
| Activity of synthetic tethered ligand sequences G-protein coupling | G$\alpha_{q/11}$ G$_i$ G$\alpha_o$ G$\alpha_{12}$ G$\alpha_{13}$ | G$\alpha_q$ G$\alpha_o$ | Unknown | Unknown |

Key: h, human; m, mouse; r, rat; x, *Xenopus*.

BIBLIOGRAPHY

Atkinson, J. B., et a/. *Hum. Pathol.* 25: 154–159, 1994.
Barnes, P. J, et al, *Fur. Respir. J.* 9: 636–642, 1996a.
Barnes, P. J, *Br. J. Clin. Pharmacol.* 42: 3–10, 1996b.
Barnes, P. J, et al, *Am. J. Respir. Crit. Care. Med.* 153: 23–25, 1996c.
Blackhart, B. D, et al. *J. Bid/. Chem.* 271: 16466–16471, 1996.
Bohm, S. K, et al, *Biochem. J.* 314: 1009–1016, 1996a.
Bohm, S. K, et al, *J. Biol. Chem.* 271: 22003–22016, 1996b.
Boucher, R C *J. Physiol.*, 516: 631–638, 1999.
Caughey, G. H., *Am. J. Respir. Mol. Biol.* 16: 621–628, 1997.
Caughey, G. H., *Am. J. Respir. Crit. Care Med.* 150: 138–142, 1994.
Chester, A. H., O'neil, G. S., Tadjkarimi, S., Palmer, R. M. J., Moncada, S. and Y acoub, M. H. *Int. J. Cardiol.* 29: 305–309, 1990.
Costello, J. F., Dunlop, L. S. and Gardiner, P. J. *Br-J-Clin-Pharmacol.*, 20: 355–9, 1985.
Coughlin, S. R., et al, *J. Clin. Invest.* 89: 351–355, 1992.
Daniel, E. E., Abela, A. P., Janssen, L. J. and O'Byme, P. M. *Can-J-Physiol-Pharmacol.* 70: 624–34, 1992.
De Caterina, R., et al, *Pharmacol. Res.* 27: 1–19, 1993.
Dennington, P. M., et al. *Clin. Exp. Pharmacol. Physiol.* 21: 349–358, 1994.
Dery, O., et al. *Am. J. Physiol.* 274: 1429–1452, 1998.
Drummond, G. R. and Cocks T. M. Br. J. Pharmacol., L17: 1035–1040, 1996.
Fager G., *Circ. Res.* 77: 645–650, 1995.
Garland, C. J. et al, *Trends Pharmacol. Sci.* 16: 23–30, 1995.
Hoxie, J. A. et al, *J. Biol. Chem.* 268:13756–13763, 1993.
Hwa, J. J. et al, *Circ. Res.* 78: 581–588, 1996.
Ishihara, H., et al, *Nature* 386: 502–506, 1997.
Kemp, B. K. and Cocks, T.: d. Br. J. Pharmacol., 920: 757–762, 1997.
Kahn, M. L. et al, *Nature* 394: 690–694, 1998.
Kemp, B. K. et al. Br. J. Pharmacol. 720: 757–762, 1997.
Koshikawa, N., et al, *FEES Letters* 409: 442–448, 1997.
Kovanen, P. T. et al, Circulation 92: 1084–1088, 1995.
Kruse, H. J. et al, *Am. J. Physiol.* 268: 36–44, 1995.
Laitinen, L. A., Laitinen, A. and Widdicombe, J. Am-Rev-Respir-Dis., 735: 567–70, 1987.
Liu, L. W., Vu, T.-K. H., Es mon, C. T. and Coughlin, S. R. J. Biol. Chem., 266: 16977, 16980, 1991.
Mari, B., et al, FASEB J. 70: 309–316, 1995.
Molino M., et al, The Journal of Biological Chemistry 272: 4043–4049, 1997.
Moncada, S., et al, Pharmacol. Rev. 4: 109–142, 1991.
Muramatsu, I., et al, Can. J. Physiol., Pharmacol. 70: 996–1003, 1992.
Nelken, N. A., et al, J. Clin. Invest 90: 1614–1621, 1992.
Nizankowska, E., Sheridan, A. Q., Maile, M H., Cross, J., Nizankowski, R., Prochowsk a, K. and Szczeklik, A. Prostaglandins, 29: 349–62, 1985.
Ngaiza, J. R., et al, *Biochem. Biophys. Res. Comm.* 179: 1656–1661, 1991.
Nystedt, S., et al, *Proc. Natl. Acad. Sci. USA* 91: 9208–9212, 1994.
Nystedt, S., et al. *Proc. Nato Acad. Sci. USA* 91: 9208–9212, 1994.
Olivier, K N, Bennet, W D, Hohneker, K I N, Zeman, K L, Edwards, L J, Boucher, R C, Knowles, M R. *Am. J. Respir. Crit. Care Med.*, 154: 217–223, 1996.
Saifeddine, M., et al. *Br. J. Pharmacol.* 118: 521–530, 1996.
Schwarze, S. R. et al. *Nature* 285: 1569–1572, 1999.

Stork, A. P. and Cocks, T. M. *Br. J. Pharmacol.*, L13: 1099–1104, 1994b

Stork, A. P, and Cocks, T.] 1. *Br. J. Pharmacol.*, L13: 1093–1098, 1994a.

Stork, A. P. and Cocks, T.] d. *Br. J. Pharmacol.*, L13: 1099–1104, 1994b.

Scarborough, R. M., Naughtc tn, M. A., Teng, W., Hung, D. T., Rose, J., Vu, T.-K. H., Wheaton, V. I., Turek., C. W. and Coughlin, S. R. *J. Biol. Chem.*, 267: 3146–13149, 1992.

Schultz, B D, Singh, A K, Devor, D C & Bridges, R J. Physiol. *Rev.*, 79 (suppl. 1): S109–S144, 1999

Tesfamariam, B., et al, *Am. J'. Physiol.* 265: 1744–1749, 1993.

Tesfamariam, B. Am. J. Physiol., 1994 267H1962–H1967.

Vassallo, R. R. J., Kieber-Emmons, T., Cichowski, K. and Brass, L. F. *J. Biol. Chem,* 267 6081–6085, 1992.

Vu, T-K. H. et al, *Cell* 646: 1057–1068, 1991.

White, R. P., Shimazaki, Y. and Robertson, J. T. *Blood Vessels,* 21: 12–22, 1984.

Xu et al, Proc. Natl. Acad. Sci. USA 95: 6642–6646, 1998.

Yamada, T., et al. Surgery 119: 494–497, 1996.

Yasuoka, S., et al. Am. J. Respir. Cell Mol. Biol. 16: 300–308, 1997.

---

What is claimed is:

1. A method for mediating relaxation of an airway of an animal, said method comprising administering to said animal, an amount of a peptide effective for mediating relaxation of said airway, said peptide having a sequence comprising SLIGRL (SEQ ID NO:2) or a peptide analog thereof in which an amino acid is replaced with a non-natural amino acid, wherein said peptide is capable of activating an airway epithelium protease activated receptor-2 (PAR2) under conditions sufficient for activation of said PAR2 to occur, thereby mediating relaxation of said airway.

2. The method according to claim 1 wherein the relaxation of the airway is caused by a disease condition selected from the group consisting of asthma, bronchitis, hayfever, alveolitis, ciliary dyskinesis and pulmonary inflammation.

3. The method according to claim 1 wherein the peptide comprises the sequence of SEQ ID NO.2.

4. The method according to claim 3 wherein the peptide is modified to permit entry across an epithelial and/or subcutaneous layer.

5. The method according to claim 4 wherein the peptide is fused to penetratin.

6. The method according to claim 4 wherein the peptide is fused to TAT.

7. A method of identifying an agent for treatment or prophylaxis of inflammation of an airway of an animal, comprising:

exposing PAR2 to the agent; and measuring the ability of the agent to activate the PAR2, wherein the agent is identified as capable of being useful for said treatment or prophylaxis of inflammation of an airway of an animal if it does have the ability to activate PAR2; and further testing the peptide for treatment or prophylaxis of inflammation of an airway of an animal if it is identified as being useful.

8. The method of claim 1, wherein said peptide incorporates a non-natural amino acid.

9. The method of claim 1, wherein said peptide incorporates a non-natural amino acid listed in the following table:

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |

-continued

| Non-conventional amino acid | Code |
|---|---|
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylaianine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-a-methylserine | Mser |
| L-α-methyltryptophan | Mtrp |
| L-α-methylvaline | Mval |
| N-(N-(2,2-diphenylethyl) carbamyimethyl)glycine | Nnbhm |
| 1-carboxy-1-(2,2-diphenyl-ethylamino)cyclopropane | Nmbc |
| L-N-methylalanine | Nmala |

-continued

| Non-conventional amino acid | Code |
|---|---|
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisoleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methyinorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylaianine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylaianine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylaianine | Mhphe |
| N-(2-methylthioethyl)glycine | Nmet |
| L-α-methyllysine | Mlys |

-continued

| Non-conventional amino acid | Code |
|---|---|
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

10. A method for treatment of inflammation of an airway of an animal, said method comprising administering to said animal, an amount of a peptide effective for treatment of inflammation, said peptide having a sequence comprising SLIGRL (SEQ ID NO:2) or a peptide analog thereof in which an amino acid is replaced with a non-natural amino acid, wherein said peptide is capable of activating an airway epithelium protease activated receptor-2 (PAR2) under conditions sufficient for activation of said PAR2 to occur, thereby providing said treatment of inflammation.

11. The method according to claim 10 wherein the inflammation of the airway is caused by a disease condition selected from the group consisting of asthma, bronchitis, hayfever, alveolitis, ciliary dyskinesis and pulmonary inflammation.

12. The method according to claim 10 wherein the peptide comprises the sequence of SEQ ID NO.2.

13. The method according to claim 12 wherein the peptide is modified to permit entry across an epithelial and/or subcutaneous layer.

14. The method according to claim 12 wherein the peptide is fused to penetratin.

15. The method according to claim 12 wherein the peptide is fused to TAT.

16. The method of claim 10, wherein said peptide incorporates a non-natural amino acid listed in the following table:

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |

-continued

| Non-conventional amino acid | Code |
|---|---|
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-a-methylserine | Mser |
| L-α-methyltryptophan | Mtrp |
| L-α-methylvaline | Mval |
| N-(N-(2,2-diphenylethyl) carbamyimethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisoleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |

| Non-conventional amino acid | Code |
|---|---|
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylaianine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylaianine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylaianine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylaianine | Nmhphe |
| N-(N-(3,3-diphenylpropyl) carbamylmethyl)glycine | Nnbhe |

* * * * *